United States Patent
Nadal et al.

(10) Patent No.: US 12,016,356 B2
(45) Date of Patent: Jun. 25, 2024

(54) SWEET PROTEIN FROM TRUFFLE

(71) Applicant: Myco Technology, Inc., Aurora, CO (US)

(72) Inventors: Marina Nadal, Aurora, CO (US); Anthony J. Clark, Aurora, OH (US); Zheyuan Guo, Aurora, CO (US); Stephen A. Gravina, Aurora, CO (US); Anthony Westgate, Aurora, CO (US); Bassam Alkotaini, Aurora, CO (US); Ashley Han, Aurora, CO (US); Brendan Sharkey, Aurora, CO (US); Evan Strassburger, Aurora, CO (US); Joseph Meilen, Aurora, CO (US); Hyung Chang, Aurora, CO (US); Alan D. Hahn, Aurora, CO (US)

(73) Assignee: MYCOTECNOLOGY, INC., Aurora, CO (US)

( * ) Notice: Subject to any disclaimer, the term of this patent is extended or adjusted under 35 U.S.C. 154(b) by 0 days.

(21) Appl. No.: 17/680,818

(22) Filed: Feb. 25, 2022

(65) Prior Publication Data

US 2022/0183333 A1    Jun. 16, 2022

Related U.S. Application Data

(63) Continuation of application No. 17/359,048, filed on Jun. 25, 2021, now Pat. No. 11,297,861.

(60) Provisional application No. 63/044,245, filed on Jun. 25, 2020.

(51) Int. Cl.
| | |
|---|---|
| C07K 14/00 | (2006.01) |
| A23L 27/30 | (2016.01) |
| C07K 1/20 | (2006.01) |
| C07K 14/37 | (2006.01) |

(52) U.S. Cl.
CPC ............. *A23L 27/31* (2016.08); *C07K 1/20* (2013.01); *C07K 14/37* (2013.01)

(58) Field of Classification Search
CPC ............ A23L 27/31; C07K 1/20; C07K 14/37
See application file for complete search history.

(56) References Cited

U.S. PATENT DOCUMENTS

| | | | |
|---|---|---|---|
| 8,569,581 B2 | 10/2013 | Maiyuran et al. | |
| 9,273,320 B2 | 3/2016 | Vind et al. | |
| 9,637,807 B1 | 5/2017 | Awad et al. | |
| 10,010,103 B2 | 7/2018 | Soni et al. | |
| 11,297,861 B2 | 4/2022 | Nadal et al. | |
| 2011/0067148 A1 | 3/2011 | Maiyuran et al. | |
| 2012/0107873 A1 | 5/2012 | Vind et al. | |
| 2012/0180167 A1 | 7/2012 | Usami | |
| 2012/0189167 A1 | 7/2012 | Usami | |
| 2013/0191943 A1* | 7/2013 | Apuya | C12N 15/8261 800/278 |
| 2013/0224368 A1 | 8/2013 | Guan | |
| 2016/0015064 A1 | 1/2016 | Luo et al. | |
| 2017/0295837 A1 | 10/2017 | Soni et al. | |
| 2020/0104523 A1 | 4/2020 | Theimer et al. | |
| 2021/0401013 A1 | 12/2021 | Nadal et al. | |
| 2022/0183333 A1 | 6/2022 | Nadal et al. | |
| 2023/0210154 A1 | 7/2023 | Nadal et al. | |

FOREIGN PATENT DOCUMENTS

| | | |
|---|---|---|
| CN | 1333213 A | 1/2002 |
| CN | 1343681 A | 4/2002 |
| CN | 1543474 A | 11/2004 |
| CN | 102498126 A | 6/2012 |
| CN | 109627307 A | 4/2019 |
| JP | 2005218342 A | 8/2005 |
| WO | WO 2011015633 A1 | 2/2011 |
| WO | 2014/020215 A1 | 2/2014 |
| WO | WO 2014020215 A1 | 2/2014 |
| WO | 2019/173541 A1 | 9/2019 |
| WO | 2020/146650 A1 | 7/2020 |
| WO | WO 2020146650 A1 | 7/2020 |
| WO | WO 2021263158 A1 | 12/2021 |
| WO | 2023/129938 A2 | 7/2023 |

OTHER PUBLICATIONS

U.S. Appl. No. 17/421,612, filed Jul. 8, 2021.
Assyov et al. (2016) "First Bulgarian collections of *Mattirolomyces terfezioides* (*Pezizaceae*), a potentially valuable hypogeous fungus" *Phytologia Balcanica*, Sofia, 22(3): 303-307.
Bratek et al. (1996) "Mycorrhizae between black locust (*Robinia pseudoacacia*) and *Terfezia terfezioides*" *Mycorrhiza* 6: 271-274.
De Simone et al. (2006) "Toward the Understanding of MNEI Sweetness from Hydration Map Surfaces" *Biophysical Journal* 90:3052-3061.
Diez et al. (2002) "Molecular Phylogeny of the Mycorrhizal Desert Truffles (*Terfezia* and *Tirmania*), Host Specificity and Edaphic Tolerance" *Mycologia* 94(2):247-259.
Esposito et al. (2006) "The Importance of Electrostatic Potential in the Interaction of Sweet Proteins with the Sweet Taste Receptor" *J. Mol. Biol.* 360: 448-456, doi:10.1016/j.jmb.2006.05.020.
Esposito et al. (2010) "Aggregation Mechanisms of Cystatins: A Comparative Study of Monellin and Oryzacystatin" *Biochemistry* 49: 2805-2810, DOI: 10.1021/bi902039s.
Faus, I. (2000), "Recent developments in the characterization and biotechnological production of sweet-tasting proteins", Appl. Microbiol. Biotechnol. 53(2):145-151.
Rodriguez (2008) The Hungarian Sweet Truffle (*Mattirolomyces terfezioides*) retrieved from https://www.trufamania.com/Mattirolomyces-truffles.htm on Jul. 2, 2021.

(Continued)

*Primary Examiner* — Jeanette M Lieb
(74) *Attorney, Agent, or Firm* — Leydig, Voit & Mayer, Ltd.

(57) ABSTRACT

Newly identified fungal sweet-taste modifying proteins, and the cDNA encoding said proteins are described. Specifically, Myd proteins active in sweet taste activation, and the cDNA encoding the same, are described, along with methods for isolating such cDNA and for isolating and expressing such proteins. Also disclosed is use of a sweetening composition which includes the proteins of the invention, and methods to provide improved flavor to a product for oral administration.

29 Claims, 10 Drawing Sheets

Specification includes a Sequence Listing.

(56) References Cited

OTHER PUBLICATIONS

Saritha et al. (2016) "Mushrooms and Truffles: Role in the Diet" *Encyclopedia of Food and Health*, 1-8, dx.doi.org/10.1016/B978-0-12-384947-2.00473-6.

Schulz et al. (2013) "MTSA—A Matlab program to fit thermal shift data" *Analytical Biochemistry* 433(1): 43-47 (abstract only).

Spadaccini et al. (2001) "Solution Structure of a Sweet Protein: NMR Study of MNEI, a Single Chain Monellin" *J. Mol. Biol.* 305: 505-514.

Spadaccini et al. (2003) "The Mechanism of Interaction of Sweet Proteins with the T1R2-T1R3 Recepto: Evidence from the Solution Structure of G16A-MNEI" *J. Mol. Biol.* 328: 683-692.

Tancredi et al. (1992) "Structural determination of the active site of a sweet protein: A HNMR investigation of pMNEI" *FEBS Letters* 310(1): 27-30.

Tancredi et al. (2004) "Interaction of sweet proteins with their receptor: A conformational study of peptides corresponding to loops of brazzein, monellin and thaumatic" *Eur. J. Biochem.* 271: 2231-2240, doi: 10.1111/j.1432-1033.2004.04154.x.

Temussi, Piero Andrea (2002) "Why are sweet proteins sweet? Interaction of brazzein, monellin and thaumatic with the T1R2-T1R3 receptor" *FEBS Letter* 526 1-4.

Trappe, J. M. (1971) "A Synopsis of the Carbomycetaceae and Terfeziaceae (Tuberales)" *Trans. Br. Mycol. Soc.* 57(1):85-92.

Wang et al. "Molecular and morphological data confirmed the presence of the rare species *Mattirolomyces terfezioides* in China" *Plant Diversity* 39: 89-93.

Gógán-Csorbainé et al. (2009) "*Choiromyces Meandriformis* and *Mattirolomyces terfezioides*: peculiar truffles with new perspectives" *Micol Ital*, 8 pp.

International Preliminary Report on Patentability mailed Jul. 22, 2021 in PCT/US2020/012955.

International Search Report and Written Opinion mailed Apr. 24, 2021 in PCT/US2020/012955.

International Search Report and Written Opinion mailed Oct. 25, 2021 in PCT/US2021/039176.

Kagan-Zur et al. (ed) (2014) "Desert Truffles: Phylogeny, Physiology, Distribution and Domestication" Soil Biology vol. 38 Springer, Switzerland (entire book) DOI 10.1007/978-3-642-40096-4.

Konstantinidis et al. (2014) "*Hydnotrya tulasnei* and *Mattirolomyces terfezioides* (*Pezizales*) two hypogeous fungi that rarely appear in Greece" Ascomycete.org 6(1): 4 pp.

Korz et al. (1995) "Simple fed-batch technique for high cell density cultivation of *Escherichia coli*" *Journal of Biotechnology* 39: 59-65.

Kovács et al. (2007) "Identification of host plants and description of sclerotia of the truffle *Mattirolomyces terfezioides*" *Mycol Progress* 6: 19-26.

Kovács et al. (2009) "First record of *Mattirolomyces terfezioides* from the Iberian Peninsula: its souther—and westernmost locality" *Mycotaxon* 110: 325-330.

Kovács et al. (2011) "*Terfezia* disappears from the American truffle mycota as two new genera and *Mattrolomyces* species emerge" *Mycologia* 103(4): 10 pp. DOI: 10.3852/10-273.

Leone et al. (2016) "Sweeter and stronger: enhancing sweetness and stability of the single chain monellin MNEI through molecular design" *Scientific Reports* 6: 34045, 10 pp.

Masuda et al. (2016) "A Hypersweet Protein: Removal of the Specific Negative Charge at Asp21 Enhances Thaumatin Sweetness" *Scientific Reports* 6: 20255, 9 pp.

Masuda et al. (2019) "Subatomic structure of hyper-sweet thaumatin D21N mutant reveals the importance of flexible conformations for enhanced sweetness" *Biochimie* 157: 57-63 (abstract only).

Morini et al. (2005) "From Small Sweeteneers to Sweet Proteins: Anatomy of the Binding Sites of the Human T1R2_T1R3" *J. Med. Chem* 48:5520-5529.

Niccolai et al. (2001) "Probing the surface of a sweet protein: NMR study of MNEI with a paramagnetic probe" *Protein Science* 10: 1498-1507.

Norsyahida et al. (2009) "Effects of feeding and induction strategy on the production of BmR1 antigen in recombinant *E. coli*" *Letters in Applied Microbiology* 49: 544-550, doi:10.1111/j.1472-765X.2009.02694.x.

Patel et al. (2017) "Potential health benefits of natural products derived from truffles: A review" *Trends in Food Science & Technology* 70: 1-8, doi.org/10.1016/j.tifs.2017.09.009.

International Preliminary Report on Patentability mailed Jul. 22, 2021 in PCT/US2020/012955 Applicant MycoTechnology, Inc.

International Search Report and Written Opinion mailed Apr. 24, 2020 in PCT/US 2020/012955 Applicant MycoTechnology, Inc.

International Preliminary Report on Patentability mailed Jan. 5, 2023 in PCT/US2021/039176 Applicant MycoTechnology, Inc.

International Search Report and Written Opinion mailed Jun. 15, 2023 in PCT/US2022/082443 Applicant MycoTechnology, Inc.

Johnson M. (2012) "Protein/Peptide Tags," Mater Methods, 2:116, DOI//dx.doi.org/10.13070/mm.en.2.116 obtained from web site labome.com/method/Protein-peptide-Tags.html printed Jan. 30, 2024.

UniProtKB Accession No. A0A0C3NAN6 "Full-Uncharacterized protein", Feb. 26, 2020.

UniProtKB Accession No. A0A0C3IMI1 Full-Uncharacterized protein, Feb. 26, 2020.

\* cited by examiner

His-tagged mycodulcein

E.coli

FIG. 3

SWEET PROTEIN FROM TRUFFLE

CROSS-REFERENCE TO RELATED APPLICATIONS

This patent application is a continuation of U.S. application Ser. No. 17/359,048, filed Jun. 25, 2021, which in turn claims the benefit of U.S. Provisional Patent Application No. 63/044,245, filed Jun. 25, 2020. Each of these applications is incorporated by reference herein in its entirety.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 86,721 Bytes ASCII (Text) file named "339159_0640_30B_US_ST25.TXT," created on Feb. 22, 2022.

BACKGROUND OF THE INVENTION

Excess intake of nutritive sweeteners has long been associated with diet-related health issues, such as obesity, heart disease, metabolic disorders and dental problems. Accordingly, consumers are increasingly looking for ways to decrease the amount of nutritive sweeteners in their diets. Manufacturers are responding to this demand by seeking to develop replacements for nutritive sweeteners that are better able to mimic the desirable taste and functional properties of the nutritive sweeteners.

Zero or low-calorie sweeteners derived from, preferably, natural sources are desired to limit the negative effects of high sugar consumption (e.g., diabetes and obesity, among others). Commonly-known zero or low-calorie sweeteners include aspartame, acesulfame potassium, luo han guo (monk) fruit extract, neotame, saccharin, stevia and sucralose. However, these sweeteners have taste defects such as bitterness.

A truffle is the subterranean fruiting body of some ascomycete fungi including genera which belong to the class Pezizomycetes order Pezizales. Truffles are ectomycorrhizal fungi and are therefore usually found in close association with tree roots.

So far there are seven known sweet and taste-modifying proteins, namely brazzein, thaumatin, monellin, curculin, mabinlin, miraculin and pentadin. The key residues on the protein surface responsible for biological activity have not yet been identified with certainty for any of these proteins. Monellin was found to be 100,000 times sweeter than sucrose on a molar basis, followed by brazzein and thaumatin which are 500 times and 3000 times sweeter than sucrose, respectively, on a gram basis. All of these proteins have been isolated from plants that grow in tropical rainforests. Although most of them share no sequence homology or structural similarity, thaumatin shares extensive similarity at the protein sequence level with certain non-sweet proteins found in other plants. No sweet-taste modifying proteins are known from fungi.

There remains a need in the art to produce new low or zero calorie sweeteners with improved tastes from natural sources. There remains a need in the art to economically produce such sweetening compositions from potential sources of the same, particularly from ascomycetes fungal species.

SUMMARY OF THE INVENTION

The invention relates to newly identified fungally-derived sweet proteins, and to the genes and cDNA encoding said proteins, also called MYD/Myd herein. More particularly, the invention relates to newly identified sweet-tasting proteins, to the genes and cDNA encoding said proteins, and to methods of using such proteins, genes, and cDNA in the modulation of the taste of foods. The invention provides in particular a DNA sequence encoding a novel sweet protein identified herein as MYD1 and the corresponding polypeptide Myd1 (also referred to as mycodulcein). Myd1 is the first sweet-tasting protein identified from fungi. Myd1 reduces the sourness, bitterness or astringency of foods and drinks and additionally Myd1 has an activity to enhance the taste of foods and drinks, namely a taste-modifying activity.

The invention provides a polynucleotide (e.g., isolated polynucleotide) encoding a polypeptide having sweet-taste modulation activity, wherein the polynucleotide sequence encodes a polypeptide selected from the group consisting of (a) a polypeptide sequence selected from the group consisting of SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:71, SEQ ID NO:72, SEQ ID NO:73, SEQ ID NO:74, and SEQ ID NO:75; (b) a polypeptide having at least 80% sequence identity to the polypeptide sequence selected from the group consisting of SEQ ID NO:3, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, and SEQ ID NO:17; and (c) a polypeptide sequence modified from the polypeptide sequence selected from the group consisting of SEQ ID NO:3, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, and SEQ ID NO:17 by deletion, insertion, substitution, or addition of no more than 24 amino acids, wherein the polypeptide encoding a polypeptide having sweet-taste modulation activity is not the polypeptide of SEQ ID NO:3.

The invention also provides a polynucleotide (e.g., isolated polynucleotide) selected from the group consisting of: (a) a polynucleotide comprising the nucleic acid sequence set forth in SEQ ID NO:2 with at least one substitution modification; (b) a polynucleotide comprising a nucleic acid sequence having at least 90% sequence identity to the nucleic acid sequence set forth in SEQ ID NO:2, wherein the polynucleotide is not the polynucleotide of SEQ ID NO:2, and (c) a polynucleotide comprising (i) the nucleic acid sequence set forth in SEQ ID NO:2 and (ii) a nucleotide sequence encoding a histidine tag, wherein the polynucleotide encodes a polypeptide having sweet-taste modulation activity.

In one aspect, the polypeptide sequence of the polypeptide having sweet-taste modulation activity comprises SEQ ID NO:71, SEQ ID NO:72, SEQ ID NO:73, SEQ ID NO:74, or SEQ ID NO:75. In particular, the polypeptide sequence of the polypeptide having sweet-taste modulation activity comprises SEQ ID NO:24, SEQ ID NO:26, SEQ ID NO:30, SEQ ID NO:38, SEQ ID NO:42, SEQ ID NO:44, SEQ ID NO:46, SEQ ID NO:50, SEQ ID NO:52, SEQ ID NO:54, SEQ ID NO:58, SEQ ID NO:60, SEQ ID NO:62, SEQ ID NO:64, SEQ ID NO:66, or SEQ ID NO:68.

In a particular aspect, the polynucleotide comprises the nucleic acid sequence of SEQ ID NO:23, SEQ ID NO:25, SEQ ID NO:29, SEQ ID NO:37, SEQ ID NO:41, SEQ ID NO:43, SEQ ID NO:45, SEQ ID NO:49, SEQ ID NO:51, SEQ ID NO:53, SEQ ID NO:57, SEQ ID NO:59, SEQ ID NO:61, SEQ ID NO:63, SEQ ID NO:65, or SEQ ID NO:67.

The polynucleotide encoding the polypeptide having sweet-taste modulation activity is optionally operably linked to a heterologous regulatory element. Additionally or alternatively, the polynucleotide sequence further encodes a protein tag or label. The protein tag is optionally an affinity tag. The protein is optionally a histidine tag.

In one aspect, the polynucleotide comprises SEQ ID NO:20, which corresponds to the coding sequence for His tagged mycodulcein in *E. coli* (wherein residues 364-381 correspond to an optional His tag sequence). SEQ ID NO:20 is codon-optimized for expression in *E. coli*. In another aspect, the polynucleotide comprises SEQ ID NO:22, which corresponds to the coding sequence for His tagged mycodulcein in *S. cerevisiae* (wherein residues 364-381 correspond to an optional His tag sequence). SEQ ID NO:22 is codon-optimized for expression in *S. cerevisiae*. The corresponding polypeptide of SEQ ID NO:21 corresponds to the His-tagged mycodulcein protein (wherein residues 122-127 correspond to the optional His tag sequence), which polypeptide sequence is the same for expression in *E. coli* and *S. cerevisiae*.

An expression cassette comprising the polynucleotide and a vector comprising the polynucleotide, as well as a host cell transformed with the vector is provided. A method of producing a protein having sweet-taste modulation activity, comprising culturing the host cell in a medium under conditions that result in producing the protein having sweet-taste modulation activity also is provided.

The invention includes a polypeptide (e.g., isolated polypeptide) comprising a polypeptide sequence having at least 80% sequence identity to a polypeptide sequence selected from the group consisting of SEQ ID NO:3, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, and SEQ ID NO:17; (a) wherein the polypeptide contains at least one substitution or modification relative to the polypeptide sequence selected from the group consisting of SEQ ID NO:3, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, and SEQ ID NO:17, wherein the polypeptide is not the polypeptide of SEQ ID NO:3, or (b) wherein the polypeptide further comprises a protein tag, particularly a histidine tag, and wherein the polypeptide has sweet-taste modulation activity.

In one aspect, the polypeptide (e.g., isolated polypeptide) comprises a polypeptide sequence selected from the group consisting of SEQ ID NO:71, SEQ ID NO:72, SEQ ID NO:73, SEQ ID NO:74, and SEQ ID NO:75, wherein the polypeptide optionally is not SEQ ID NO:3. In particular, the polypeptide comprises the amino acid sequence of SEQ ID NO:24, SEQ ID NO:26, SEQ ID NO:30, SEQ ID NO:38, SEQ ID NO:42, SEQ ID NO:44, SEQ ID NO:46, SEQ ID NO:50, SEQ ID NO:52, SEQ ID NO:54, SEQ ID NO:58, SEQ ID NO:60, SEQ ID NO:62, SEQ ID NO:64, SEQ ID NO:66, or SEQ ID NO:68.

The invention provides a composition, comprising a combination of (a) a product for oral administration, wherein the product is not *Mattirolomyces terfezioides* truffle, and (b) a sweetening composition comprising the polypeptide, wherein the combination has enhanced sweet taste compared to the product for oral administration. In one aspect, the polypeptide comprises an amino acid sequence having at least 80% sequence identity to a polypeptide selected from the group consisting of SEQ ID NO:3, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, and SEQ ID NO:17. In another aspect, the polypeptide has a polypeptide sequence having at least 80% sequence identity to a polypeptide sequence selected from the group consisting of SEQ ID NO:3, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, and SEQ ID NO:17; (a) wherein the polypeptide contains at least one substitution modification relative to the polypeptide sequence selected from the group consisting of SEQ ID NO:3, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, and SEQ ID NO:17, wherein the polypeptide is not the polypeptide of SEQ ID NO:3, or (b) wherein the polypeptide further comprises a histidine tag, wherein the polypeptide has sweet-taste modulation activity. For example, the polypeptide in the sweetening composition comprises the amino acid sequence of SEQ ID NO:71, SEQ ID NO:72, SEQ ID NO:73, SEQ ID NO:74, or SEQ ID NO:75 and optionally does not consist of SEQ ID NO:3. In particular, the polypeptide comprises the amino acid sequence of SEQ ID NO:24, SEQ ID NO:26, SEQ ID NO:30, SEQ ID NO:38, SEQ ID NO:42, SEQ ID NO:44, SEQ ID NO:46, SEQ ID NO:50, SEQ ID NO:52, SEQ ID NO:54, SEQ ID NO:58, SEQ ID NO:60, SEQ ID NO:62, SEQ ID NO:64, SEQ ID NO:66, or SEQ ID NO:68.

In one aspect, the invention provides a sweetening composition comprising a polypeptide comprises an amino acid sequence having at least 80% sequence identity to a polypeptide selected from the group consisting of SEQ ID NO:3, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, and SEQ ID NO:17, wherein the polypeptide is a polypeptide other than the polypeptide of the amino acid sequence of SEQ ID NO:3.

The invention provides a method for modulating the taste of a product for oral administration, comprising combining the product for oral administration with an effective amount of a sweetening composition comprising the polypeptide, wherein the product for oral administration is not *Mattirolomyces terfezioides* truffle, and wherein the combination has enhanced sweet taste compared to the product for oral administration. In one aspect, the polypeptide comprises an amino acid sequence having at least 80% sequence identity to a polypeptide selected from the group consisting of SEQ ID NO:3, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, and SEQ ID NO:17. In another aspect, the polypeptide has a polypeptide sequence having at least 80% sequence identity to a polypeptide sequence selected from the group consisting of SEQ ID NO:3, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, and SEQ ID NO:17; (a) wherein the polypeptide contains at least one substitution modification relative to the polypeptide sequence selected from the group consisting of SEQ ID NO:3, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, and SEQ ID NO:17, wherein the polypeptide is not the polypeptide of SEQ ID NO:3, or (b) wherein the polypeptide further comprises a histidine tag, wherein the polypeptide has sweet-taste modulation activity. For example, the polypeptide in the sweetening composition comprises the amino acid sequence of SEQ ID NO:71, SEQ ID NO:72, SEQ ID NO:73, SEQ ID NO:74, or SEQ ID NO:75 and optionally does not consist of SEQ ID NO:3. In particular, the polypeptide comprises the amino acid sequence of SEQ ID NO:24, SEQ ID NO:26, SEQ ID NO:30, SEQ ID NO:38, SEQ ID NO:42, SEQ ID NO:44, SEQ ID NO:46, SEQ ID NO:50, SEQ ID NO:52, SEQ ID NO:54, SEQ ID NO:58, SEQ ID NO:60, SEQ ID NO:62, SEQ ID NO:64, SEQ ID NO:66, or SEQ ID NO:68.

The product for oral administration can be a food, a beverage, a dietary supplement composition, or a pharmaceutical composition. Examples of food products include, but are not limited to, baked goods; sweet bakery products, pre-made sweet bakery mixes for preparing sweet bakery products; pie fillings and other sweet fillings, gelatins and puddings; frozen desserts; yogurts; snack bars; bread products; pre-made bread mixes for preparing bread products; sauces, syrups and dressings; sweet spreads; confectionary products; and sweetened breakfast cereals. Examples of beverage product include but are not limited to carbonated beverages; non-carbonated beverages; and beverage concentrates.

The invention also provides a method of purifying a polypeptide having sweet-taste modulation activity comprising (a) obtaining a composition comprising the polypeptide, and (b) purifying the composition via hydrophobic interaction chromatography (HIC) followed by size exclusion chromatography (SEC). In one aspect, the polypeptide comprises an amino acid sequence having at least 80% sequence identity to a polypeptide selected from the group consisting of SEQ ID NO:3, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, and SEQ ID NO:17. In another aspect, the polypeptide has a polypeptide sequence having at least 80% sequence identity to a polypeptide sequence selected from the group consisting of SEQ ID NO:3, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, and SEQ ID NO:17; (a) wherein the polypeptide contains at least one substitution modification relative to the polypeptide sequence selected from the group consisting of SEQ ID NO:3, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, and SEQ ID NO:17, wherein the polypeptide is not the polypeptide of SEQ ID NO:3, or (b) wherein the polypeptide further comprises a histidine tag, wherein the polypeptide has sweet-taste modulation activity. For example, the polypeptide comprises the amino acid sequence of SEQ ID NO:71, SEQ ID NO:72, SEQ ID NO:73, SEQ ID NO:74, or SEQ ID NO:75 and optionally does not consist of SEQ ID NO:3. In particular, the polypeptide comprises the amino acid sequence of SEQ ID NO:24, SEQ ID NO:26, SEQ ID NO:30, SEQ ID NO:38, SEQ ID NO:42, SEQ ID NO:44, SEQ ID NO:46, SEQ ID NO:50, SEQ ID NO:52, SEQ ID NO:54, SEQ ID NO:58, SEQ ID NO:60, SEQ ID NO:62, SEQ ID NO:64, SEQ ID NO:66, or SEQ ID NO:68.

Other aspects and embodiments of the invention will be apparent on review of the figures, detailed description and non-limiting examples herein.

BRIEF DESCRIPTION OF THE FIGURES

FIG. 3 shows a SDS-PAGE gel, Coomassie stained, of purification steps of SEQ ID NO:21 expressed in *E. coli*. lane 1: molecular weight standards; lane 3, crude lysate; lane 4, flow through fraction from HisPur™ Ni-NTA; lane 5, wash 1; lane 6, wash 2; lane 7, wash 3; lane 8, elution fraction.

DETAILED DESCRIPTION OF THE INVENTION

Figure 1:
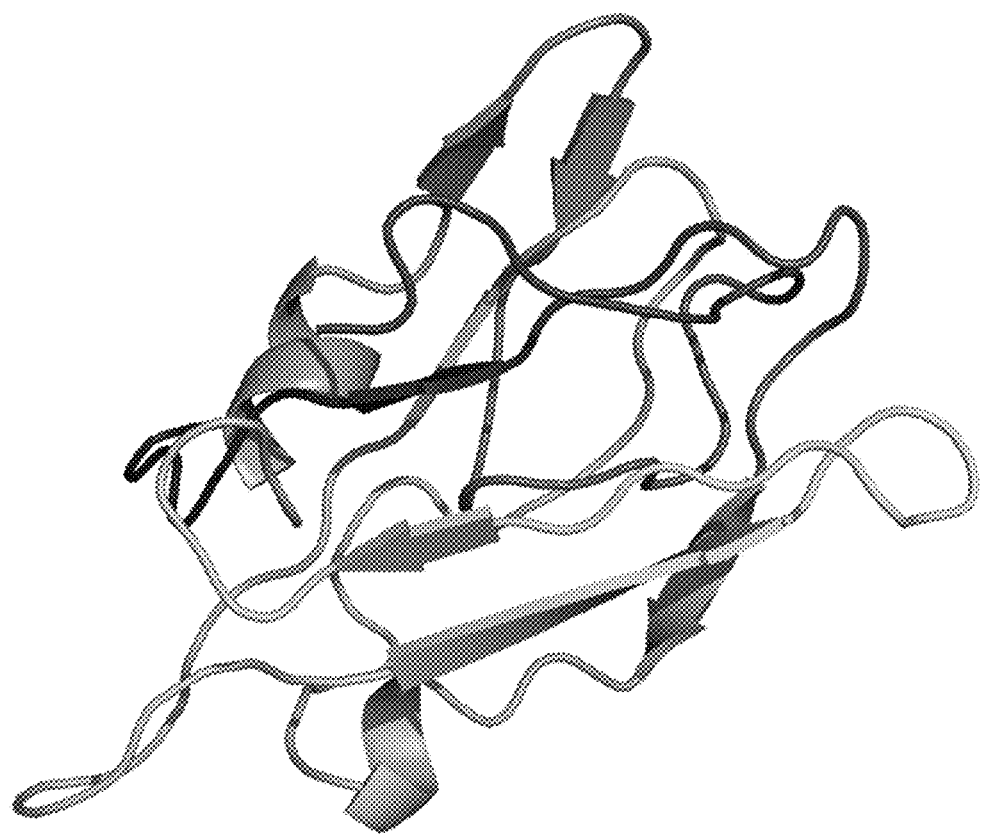
FIG. 1 shows a predicted three dimensional structure of Myd1 based on sequence data using the PHYRE2.0 protein folding prediction tool.

The invention thus provides isolated nucleic acid molecules encoding proteins which are capable of modulating sweet taste, and the polypeptides they encode. As described herein, the polypeptides of the invention mediate sweet taste perception, either alone, or in combination with food, beverage, dietary supplement, or pharmaceuticals. The invention also provides isolated polypeptides that are capable of modifying sweet taste, and compositions of same together with foods, beverages, dietary supplements, or pharmaceutical compositions, with the resultant combinations having a sweet taste. The present invention also provides methods for modifying the sweet taste of foods, beverages, dietary supplements, or pharmaceutical compositions by using the isolated polynucleotides and polypeptides of the invention.

In one aspect of the invention, provided is a newly identified fungal sweet protein termed Myd1 herein. The term "Myd polypeptides" is used herein to identify any of the polypeptides according to the present invention which e.g. have at least 80% sequence identity to SEQ ID NO:3 and also have sweet-taste modifying activity. Myd polypeptides also include peptides SEQ ID NO:8 through SEQ ID NO:17 with sweet-taste modifying activity. A sweet-tasting partially purified extract of *M. terfezioides* gleba was subjected to de novo amino acid sequencing to identify a 20-mer N-terminal sequence (SEQ ID NO:4). The Myd1 coding sequence (putatively derived from the MYD1 gene) was identified after the whole transcriptome of the *M. terfeziodes* gleba was de novo assembled using RNAseq reads. Screening the *M. terfeziodes* whole transcriptome using the 20-mer N-terminus sequences identified a transcript predicted to encode a protein with 100% identity at the N-terminus. The identified transcript is predicted to encode a 121 amino acid protein. This method identified SEQ ID NO:1. Start and stop codons were identified in the transcript to identify putative coding sequence SEQ ID NO:2. SEQ ID NO:3 is the putative protein, a 121 amino acid protein. Identity between the predicted protein SEQ ID NO:3, and other protein sequences in GENBANK were 31% or less. The coding sequences for native mycodulcein, which have been codon-optimized for expression in *E. coli* and *Saccharomyces cerevisiae* correspond to the nucleic acid sequences of SEQ ID NO:20 and SEQ ID NO:22, respectively (which encode the amino acid sequence of SEQ ID NO:3 with an optional 6 residue histidine tag, i.e., the amino acid sequence of SEQ ID NO:21).

In an aspect, the "Myd polypeptides" herein have sweet-taste modifying activity of at least 10% or higher (e.g., 15%, 20%, 25%, 30%, 35%, 40%, 45%, 50%, 55%, 60%, 65%, 70%, 75%, 80%, 85%. 90%, 95%, or higher) compared to the naturally occurring Myd polypeptide isolated from *M. terfeziodes* gleba by extraction. In other aspects, the "Myd polypeptides" herein have sweet-taste modifying activity of at least 50% or higher compared to the naturally occurring Myd polypeptide isolated from *M. terfeziodes* gleba by extraction. In an aspect, the "Myd polypeptides" herein have sweet-taste modifying activity of at least 80% or higher compared to the naturally occurring Myd polypeptide isolated from *M. terfeziodes* gleba by extraction. Sweet-taste modifying activity can be measured by any comparative method known in the art and in particular by any method as described in the examples herein and more specifically employing a method using a sensory panel as described herein.

While not wishing to be bound to any particular theory, Myd1 is believed to be involved in sweet taste activation e.g., is an agonist of taste 1 receptor member 2 (T1R2) and/or taste 1 receptor member 3 (T1R3). However, Myd1 may agonize other taste receptors, such as bitter, umami, sour and salty. Isolated or purified Myd polypeptides can then be used in the food and pharmaceutical industries to customize taste, e.g., to modulate the sweet tastes of foods or drugs.

In a first aspect, the present invention comprises a polynucleotide (e.g., isolated polynucleotide) encoding a polypeptide having sweet-taste modulation activity, wherein the polypeptide sequence comprises, consists essentially of, or consists of a polypeptide selected from the group consisting of: (a) the amino acid sequence set forth in SEQ ID NO:3, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17; (b) an amino acid sequence having at least 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%) sequence identity to the amino acid sequence set forth in SEQ ID NO:3, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17; and (c) an amino acid sequence modified from the amino acid sequence set forth in SEQ ID NO:3, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17 by deletion, insertion, substitution, or addition of no more than 24 (e.g., 1, 2, 3, 4, 5, 6, 7, 8, 9, 10, 11, 12, 13, 14, 15, 16, 17, 18, 19, 20, 21, 22, 23, 24, and any ranges thereof) amino acids. In some embodiments, the amino acid sequence of the polypeptide having sweet-taste modulation activity is the amino acid sequence set forth in SEQ ID NO:3, an amino acid sequence having at least 80% sequence identity to SEQ ID NO:3, or an amino acid modified from the amino acid sequence SEQ ID NO:3 by deletion, insertion, substitution, or addition of no more than 24 amino acids.

In a particular aspect, the invention provides a polynucleotide (e.g., isolated polynucleotide) encoding a polypeptide having sweet-taste modulation activity, wherein the polynucleotide sequence encodes a polypeptide selected from the group consisting of: (a) a polypeptide sequence selected from the group consisting of SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, and SEQ ID NO:17; (b) a polypeptide having at least 80% sequence identity to the polypeptide sequence selected from the group consisting of SEQ ID NO:3, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, and SEQ ID NO:17; and (c) a polypeptide sequence modified from the polypeptide sequence selected from the group consisting of SEQ ID NO:3, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, and SEQ ID NO:17 by deletion, insertion, substitution, or addition of no more than 24 amino acids, wherein the isolated polypeptide encoding a polypeptide having sweet-taste modulation activity is not the polypeptide of SEQ ID NO:3.

In another aspect, the present invention includes a polynucleotide (e.g., isolated polynucleotide) wherein the polynucleotide is selected from the group consisting of: (a) a polynucleotide comprising the nucleic acid sequence set forth in SEQ ID NO:2, optionally containing at least one (e.g., 2, 3, 4, 5, 6, 7, 8, 9, 10, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, and ranges of any of these values) modification (e.g., deletion, insertion, substitution, or addition; and (b) a polynucleotide comprising a nucleic acid sequence having at least 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%) sequence identity to the nucleic acid sequence set forth in SEQ ID NO:2, optionally wherein the polynucleotide is not the polynucleotide of SEQ ID NO:2. In an embodiment, the polynucleotide encodes a polypeptide having sweet-taste modulation activity. In an embodiment, the amino acid sequence of the polypeptide having sweet-taste modulation activity is the amino acid sequence set forth in SEQ ID NO:3.

In one aspect, the invention provides a polynucleotide (e.g., isolated polynucleotide) wherein the polynucleotide sequence comprises, consists essentially of, or consists of a polynucleotide selected from the group consisting of: (a) a polynucleotide comprising the nucleic acid sequence set forth in SEQ ID NO:2 with at least one (e.g., 2, 3, 4, 5, 6, 7, 8, 9, 10, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, and ranges of any of these values) substitution modification; (b) a polynucleotide comprising a nucleic acid sequence having at least 90% (at least 91%, at least 92%, at least 93%, at least 94%, at least 95%, at least 96%, at least 97%, at least 98%, or at least 99%) sequence identity to the nucleic acid sequence set forth in SEQ ID NO:2, wherein the polynucleotide optionally is not the polynucleotide of SEQ ID NO:2, and (c) a polynucleotide comprising (i) the nucleic acid sequence set forth in SEQ ID NO:2 and (ii) a nucleotide sequence encoding a histidine tag, wherein the polynucleotide encodes a polypeptide having sweet-taste modulation activity.

The polynucleotide encoding the Myd of the present invention can be in the form of a single-stranded or double-stranded DNA, RNA or an artificial nucleic acid, or can be a cDNA or a chemically synthesized DNA which does not comprise any intron.

The term "nucleic acid" or "nucleic acid sequence" refers to a deoxy-ribonucleotide or ribonucleotide oligonucleotide in either single- or double-stranded form. The term encompasses nucleic acids, i.e., oligonucleotides, containing known analogs of natural nucleotides. The term also encompasses nucleic-acid-like structures with synthetic backbones (see e.g., Oligonucleotides and Analogues, a Practical Approach, ed. F. Eckstein, Oxford Univ. Press (1991); Antisense Strategies, Annals of the N.Y. Academy of Sciences, Vol. 600, Eds. Baserga et al. (NYAS 1992); Milligan J. Med. Chem. 36:1923-1937 (1993); Antisense Research and Applications (1993, CRC Press), WO 97/03211; WO 96/39154; Mata, Toxicol. Appl. Pharmacol. 144:189-197 (1997); Strauss-Soukup, Biochemistry 36:8692-8698 (1997); Samstag, Antisense Nucleic Acid Drug Dev, 6:153-156 (1996)).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating, e.g., sequences in which the third position of one or more selected codons is substituted with mixed-base and/or deoxyinosine residues (Batzer et al., Nucleic Acid Res., 19:5081 (1991); Ohtsuka et al., J. Biol. Chem., 260:2605-2608 (1985); Rossolini et al., Mol. Cell. Probes, 8:91-98 (1994)). The term nucleic acid is used interchangeably with gene, cDNA, mRNA, oligonucleotide, and polynucleotide.

The invention also provides an expression cassette comprising the polynucleotide encoding a Myd polypeptide and a host cell transformed with the vector.

In another aspect, the invention provides a polypeptide (e.g., an isolated polypeptide) comprising, consisting essentially of, or consisting of a polypeptide sequence having at least 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%) sequence identity to a polypeptide sequence selected from the group consisting of SEQ ID NO:3, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, and SEQ ID NO:17, wherein the polypeptide optionally contains at least one (e.g., 2, 3, 4, 5, 6, 7, 8, 9, 10, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, and ranges of any of these values) modification (e.g., deletion, insertion, substitution, or addition), wherein the polypeptide optionally further comprises a histidine tag, and wherein the polypeptide has sweet-taste modulation activity. The term "consisting essentially of" allows for the inclusion of components that are not essential to the function or activity of the product and do not materially affect the function or activity, such an anti-caking agent, filler, stabilizer (e.g., thermal stabilizer), and bulking agent (e.g., maltodextrose, gum acacia and the like).

The polypeptide comprises SEQ ID NO:3 or at least 80% sequence identity to SEQ ID NO:3. The polypeptide comprises SEQ ID NO:8 or at least 80% sequence identity to SEQ ID NO:8. The polypeptide comprises SEQ ID NO:9 or at least 80% sequence identity to SEQ ID NO:9. The polypeptide comprises SEQ ID NO:10 or at least 80% sequence identity to SEQ ID NO:10. The polypeptide comprises SEQ ID NO:11 or at least 80% sequence identity to SEQ ID NO:11. The polypeptide comprises SEQ ID NO:12 or at least 80% sequence identity to SEQ ID NO:12. The polypeptide comprises SEQ ID NO:13 or at least 80% sequence identity to SEQ ID NO:13. The polypeptide comprises SEQ ID NO:14 or at least 80% sequence identity to SEQ ID NO:14. The polypeptide comprises SEQ ID NO:15 or at least 80% sequence identity to SEQ ID NO:5. The polypeptide comprises SEQ ID NO:16 or at least 80% sequence identity to SEQ ID NO:16. The polypeptide comprises SEQ ID NO:17 or at least 80% sequence identity to SEQ ID NO:17.

In one embodiment, the polypeptide sequence is selected from the group consisting of SEQ ID NO:3, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, and SEQ ID NO:17. In one embodiment, the polypeptide is not the polypeptide of SEQ ID NO:3.

In one aspect, the polypeptide comprises amino acid residues 1-11, 17-32, 39, 40, 45-67, 73-100, and 110-121 of SEQ ID NO:3. In one aspect, the polypeptide comprises amino acid residues 1-11, 17-32, 39, 40, 45-67, 73-100, and 110-121 of SEQ ID NO:3, but the polypeptide is not the polypeptide having the amino acid sequence of SEQ ID NO:3.

In another aspect, the polypeptide comprises amino acid residues 1-121 of SEQ ID NO:3, wherein in amino acid residues 12-16, 33-38, 41-44, 68-72, or 101-109 of the polypeptide sequence there is at least 1 (e.g., 1, 2, 3, 4, 5, 6, 7, 8, 9, 10, 11, 12, 13, 14, 15, 16, 17, 18, 19, 20, 21, 22, 23, 24, or any range of values thereof) amino acid substitution, addition, insertion, or deletion compared to SEQ ID NO:3 in the listed residues. In another aspect, the polypeptide sequence of the polypeptide having sweet-taste modulation activity encoded by the polynucleotide is a polypeptide comprising amino acid residues 1-121 of SEQ ID NO:3, wherein in amino acid residues 12-16, 33-38, 41-44, 68-72, or 101-109 of the polypeptide sequence there is at least 1 amino acid substitution, addition, insertion, or deletion compared to SEQ ID NO:3 in the listed residues and wherein the polypeptide has at least 80% sequence identity with SEQ ID NO:3.

In another aspect, the present invention includes a recombinant polypeptide having sweet modulation activity comprising, consisting essentially of, or consisting of an amino acid sequence having at least 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%) sequence identity to SEQ ID NO:3, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17 fused to a heterologous signal peptide or transit peptide. The term "consisting essentially of" allows for the inclusion of components that are not essential to the function or activity of the product and do not materially affect the function or activity, such an anti-caking agent, filler, stabilizer (e.g., thermal stabilizer), and bulking agent (e.g., maltodextrose, gum acacia and the like).

In another aspect, the present invention includes a polypeptide having sweet modulation activity comprising, consisting essentially of, or consisting of an amino acid having at least 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%) sequence identity to SEQ ID NO:3 (or, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17), and containing at least one substitution modification relative to SEQ ID NO:3 (or, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17). In some aspects, a polypeptide of the invention comprises 1 to 24 amino acid substitutions at position 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 42, 44, 45, 46, 47, 48, 49, 50, 51, 52, 53, 54, 56, 57, 58, 59, 60, 62, 63, 64, 65, 66, 67, 68, 69, 70, 71, 72, 73, 74, 75, 76, 77, 78, 79, 80, 81, 82, 83, 84, 85 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, or 121, compared to the corresponding amino acid of SEQ ID NO:3. The term "consisting essentially of" allows for the inclusion of components that are not essential to the function or activity of the product and do not materially affect the function or activity, such an anti-caking agent, filler, stabilizer (e.g., thermal stabilizer), and bulking agent (e.g., maltodextrose, gum acacia and the like).

In a particular aspect, the polypeptide sequence of the polypeptide having sweet-taste modulation activity that is encoded by the polynucleotide comprises the amino acid sequence of SEQ ID NO:71, SEQ ID NO:72, SEQ ID NO:73, SEQ ID NO:74, or SEQ ID NO:75.

SEQ ID NO:71 (consensus sequence 1) corresponds to SEQ ID NO:3 except that positions 3, 11-16, 26, 33, 34, 36-38, 41-43, 51, 57, 66, 68-72, 85, 86, 89, 97, 101-110, 117, and 120 are any amino acid. The invention provides a polypeptide comprising the amino acid sequence of SEQ ID NO:71.

SEQ ID NO:72 (consensus sequence 2) corresponds to SEQ ID NO:3 except that positions 3, 11-16, 26, 33, 37, 38, 41, 43, 51, 57, 66, 68-70, 72, 85, 86, 89, 97, 101-103, 105-110, 117, and 120 are any amino acid (i.e., the prolines at positions 34, 36, 42, 71, and 104 of SEQ ID NO:3 are maintained). The invention provides a polypeptide comprising the amino acid sequence of SEQ ID NO:72.

SEQ ID NO:73 (consensus sequence 3) and SEQ ID NO:74 (consensus sequence 4) correspond to SEQ ID NO:3 except that positions 3, 11-16, 26, 33, 37, 38, 41, 43, 51, 57, 66, 68-70, 72, 85, 86, 89, 97, 101-103, 105-110, 117, and 120 can include conservative modifications as described herein. The invention provides a polypeptide comprising the amino acid sequence of SEQ ID NO:73. The invention provides a polypeptide comprising the amino acid sequence of SEQ ID NO:74.

SEQ ID NO:75 (consensus sequence 5) corresponds to SEQ ID NO:3 except that positions 3, 11, 26, 51, 57, 66, 69, 85, 86, 89, 97, 103, 106, 110, 117, and 120 can include conservative modifications as described herein. The invention provides a polypeptide comprising the amino acid sequence of SEQ ID NO:75.

In particular aspect, the polypeptide sequence of the polypeptide having sweet-taste modulation activity comprises SEQ ID NO:3 with one or more modifications (e.g., 1, 2, 3, 4, 5, 6, 7, 8, 9, 10, 11, 12, 13, 14, 15, and 16) at residues 3, 11, 26, 51, 57, 66, 69, 85, 86, 89, 97, 103, 106, 110, 117, and 120 of SEQ ID NO:3. Exemplary modifications relative to SEQ ID NO:3 (for the polypeptide) are set forth herein (see Example 8; Table 3). For example, the polypeptide sequence of the polypeptide having sweet-taste modulation activity comprises SEQ ID NO:24, SEQ ID NO:26, SEQ ID NO:30, SEQ ID NO:38, SEQ ID NO:42, SEQ ID NO:44, SEQ ID NO:46, SEQ ID NO:50, SEQ ID NO:52, SEQ ID NO:54, SEQ ID NO:58, SEQ ID NO:60, SEQ ID NO:62, SEQ ID NO:64, SEQ ID NO:66, or SEQ ID NO:68 or an amino acid sequence with at least 80% (e.g., 81%, 82%, 83%, 84%, 85%, 86%, 87%, 88%, 89%, 90%, 91%, 92%, 93%, 94%, 95%, 96%, 97%, 98%, or 99%) sequence identity to SEQ ID NO:24, SEQ ID NO:26, SEQ ID NO:30, SEQ ID NO:38, SEQ ID NO:42, SEQ ID NO:44, SEQ ID NO:46, SEQ ID NO:50, SEQ ID NO:52, SEQ ID NO:54, SEQ ID NO:58, SEQ ID NO:60, SEQ ID NO:62, SEQ ID NO:64, SEQ ID NO:66, or SEQ ID NO:68.

The polypeptide sequence of the polypeptide having sweet-taste modulation activity comprises SEQ ID NO:24 (D3E) or at least 80% sequence identity to SEQ ID NO:24. The polypeptide sequence of the polypeptide having sweet-taste modulation activity comprises SEQ ID NO:26 (K11R) or at least 80% sequence identity to SEQ ID NO:26. The polypeptide sequence of the polypeptide having sweet-taste modulation activity comprises SEQ ID NO:30 (K26R) or at least 80% sequence identity to SEQ ID NO:30. The polypeptide sequence of the polypeptide having sweet-taste modulation activity comprises SEQ ID NO:38 (K51R) or at least 80% sequence identity to SEQ ID NO:38. The polypeptide sequence of the polypeptide having sweet-taste modulation activity comprises SEQ ID NO:42 (R57K) or at least 80% sequence identity to SEQ ID NO:42. The polypeptide sequence of the polypeptide having sweet-taste modulation activity comprises SEQ ID NO:44 (R66K) or at least 80% sequence identity to SEQ ID NO:44. The polypeptide sequence of the polypeptide having sweet-taste modulation activity comprises SEQ ID NO:46 (D69E) or at least 80% sequence identity to SEQ ID NO:46. The polypeptide sequence of the polypeptide having sweet-taste modulation activity comprises SEQ ID NO:50 (D85E) or at least 80% sequence identity to SEQ ID NO:50. The polypeptide sequence of the polypeptide having sweet-taste modulation activity comprises SEQ ID NO:52 (E86D) or at least 80% sequence identity to SEQ ID NO:52. The polypeptide sequence of the polypeptide having sweet-taste modulation activity comprises SEQ ID NO:54 (E89D) or at least 80% sequence identity to SEQ ID NO:54. The polypeptide sequence of the polypeptide having sweet-taste modulation activity comprises SEQ ID NO:58 (D97E) or at least 80% sequence identity to SEQ ID NO:58. The polypeptide sequence of the polypeptide having sweet-taste modulation activity comprises SEQ ID NO:60 (K103R) or at least 80% sequence identity to SEQ ID NO:60. The polypeptide sequence of the polypeptide having sweet-taste modulation activity comprises SEQ ID NO:62 (R106K) or at least 80% sequence identity to SEQ ID NO:62. The polypeptide sequence of the polypeptide having sweet-taste modulation activity comprises SEQ ID NO:64 (R110K) or at least 80% sequence identity to SEQ ID NO:64. The polypeptide sequence of the polypeptide having sweet-taste modulation activity comprises SEQ ID NO:66 (E117D) or at least 80% sequence identity to SEQ ID NO:66. The polypeptide sequence of the polypeptide having sweet-taste modulation activity comprises SEQ ID NO:68 (K120R) or at least 80% sequence identity to SEQ ID NO:68.

In another aspect, the polynucleotide encoding the polypeptide having sweet-taste modulation activity comprises SEQ ID NO:23, SEQ ID NO:25, SEQ ID NO:29, SEQ ID NO:37, SEQ ID NO:41, SEQ ID NO:43, SEQ ID NO:45, SEQ ID NO:49, SEQ ID NO:51, SEQ ID NO:53, SEQ ID NO:57, SEQ ID NO:59, SEQ ID NO:61, SEQ ID NO:63, SEQ ID NO:65, or SEQ ID NO:67 or an nucleic acid sequence with at least 80% (e.g., 81%, 82%, 83%, 84%, 85%, 86%, 87%, 88%, 89%, 90%, 91%, 92%, 93%, 94%, 95%, 96%, 97%, 98%, or 99%) sequence identity to SEQ ID NO:23, SEQ ID NO:25, SEQ ID NO:29, SEQ ID NO:37, SEQ ID NO:41, SEQ ID NO:43, SEQ ID NO:45, SEQ ID NO:49, SEQ ID NO:51, SEQ ID NO:53, SEQ ID NO:57, SEQ ID NO:59, SEQ ID NO:61, SEQ ID NO:63, SEQ ID NO:65, or SEQ ID NO:67.

The polynucleotide comprises SEQ ID NO:23 (corresponding to D3E) or at least 80% sequence identity to SEQ ID NO:23. The polynucleotide comprises SEQ ID NO:25 (corresponding to K11R) or at least 80% sequence identity to SEQ ID NO:25. The polynucleotide comprises SEQ ID NO:29 (corresponding to K26R) or at least 80% sequence identity to SEQ ID NO:29. The polynucleotide comprises SEQ ID NO:37 (corresponding to K51R) or at least 80% sequence identity to SEQ ID NO:37. The polynucleotide comprises SEQ ID NO:41 (corresponding to R57K) or at least 80% sequence identity to SEQ ID NO:41. The polynucleotide comprises SEQ ID NO:43 (corresponding to R66K) or at least 80% sequence identity to SEQ ID NO:43. The polynucleotide comprises SEQ ID NO:45 (corresponding to D69E) or at least 80% sequence identity to SEQ ID NO:45. The polynucleotide comprises SEQ ID NO:49 (D85E) or at least 80% sequence identity to SEQ ID NO:49. The polynucleotide comprises SEQ ID NO:51 (corresponding to E86D) or at least 80% sequence identity to SEQ ID NO:51. The polynucleotide comprises SEQ ID NO:53 (corresponding to E89D) or at least 80% sequence identity to SEQ ID NO:53. The polynucleotide comprises SEQ ID NO:57 (corresponding to D97E) or at least 80% sequence identity to SEQ ID NO:57. The polynucleotide comprises SEQ ID NO:59 (corresponding to K103R) or at least 80% sequence identity to SEQ ID NO:59. The polynucleotide comprises SEQ ID NO:61 (corresponding to R106K) or at least 80% sequence identity to SEQ ID NO:61. The polynucleotide comprises SEQ ID NO:63 (R110K) or at least 80% sequence identity to SEQ ID NO:63. The polynucleotide comprises SEQ ID NO:65 (E117D) or at least 80% sequence identity to SEQ ID NO:65. The polynucleotide comprises SEQ ID NO:67 (K120R) or at least 80% sequence identity to SEQ ID NO:67.

In one aspect, the polynucleotide comprises SEQ ID NO:20, which corresponds to the coding sequence for His tagged mycodulcein in *E. coli* (wherein residues 364-381 correspond to an optional His tag sequence). SEQ ID NO:20 is codon-optimized for expression in *E. coli*. In another aspect, the polynucleotide comprises SEQ ID NO:22, which corresponds to the coding sequence for His tagged mycodulcein in *S. cerevisiae* (wherein residues 364-381 correspond to an optional His tag sequence). SEQ ID NO:22 is codon-optimized for expression in *S. cerevisiae*. The corresponding polypeptide of SEQ ID NO:21 corresponds to the His-tagged mycodulcein protein (wherein residues 122-127 correspond to the optional His tag sequence), which polypeptide sequence is the same for expression in *E. coli* and *S. cerevisiae*. Therefore, the invention also provides a polypeptide comprising the amino acid sequence of SEQ ID NO:21.

The invention also provides a polypeptide comprising the amino acid sequence of SEQ ID NO:28, SEQ ID NO:32, SEQ ID NO:34, SEQ ID NO:36, SEQ ID NO:40, SEQ ID NO:48, or SEQ ID NO:56 or an amino acid sequence with at least 80% (e.g., 81%, 82%, 83%, 84%, 85%, 86%, 87%, 88%, 89%, 90%, 91%, 92%, 93%, 94%, 95%, 96%, 97%, 98%, or 99%) sequence identity to SEQ ID NO:28, SEQ ID NO:32, SEQ ID NO:34, SEQ ID NO:36, SEQ ID NO:40, SEQ ID NO:48, or SEQ ID NO:56.

The polypeptide comprises SEQ ID NO:28 (R20K) or at least 80% sequence identity to SEQ ID NO:28. The polypeptide comprises SEQ ID NO:32 (E35D) or at least 80% sequence identity to SEQ ID NO:32. The polypeptide comprises SEQ ID NO:34 (K44R) or at least 80% sequence identity to SEQ ID NO:34. The polypeptide comprises SEQ ID NO:36 (D46E) or at least 80% sequence identity to SEQ ID NO:36. The polypeptide comprises SEQ ID NO:40 (D52E) or at least 80% sequence identity to SEQ ID NO:40. The polypeptide comprises SEQ ID NO:48 (R75K) or at least 80% sequence identity to SEQ ID NO:48. The polypeptide comprises SEQ ID NO:56 (D94E) or at least 80% sequence identity to SEQ ID NO:56.

In another aspect, the polynucleotide comprises SEQ ID NO:27, SEQ ID NO:31, SEQ ID NO:33, SEQ ID NO:35, SEQ ID NO:39, SEQ ID NO:47, or SEQ ID NO:55 or a nucleic acid sequence with at least 80% (e.g., 81%, 82%, 83%, 84%, 85%, 86%, 87%, 88%, 89%, 90%, 91%, 92%, 93%, 94%, 95%, 96%, 97%, 98%, or 99%) sequence identity to SEQ ID NO:27, SEQ ID NO:31, SEQ ID NO:33, SEQ ID NO:35, SEQ ID NO:39, SEQ ID NO:47, or SEQ ID NO:55.

The polynucleotide comprises SEQ ID NO:27 (corresponding to R20K) or at least 80% sequence identity to SEQ ID NO:27. The polynucleotide comprises SEQ ID NO:31 (corresponding to E35D) or at least 80% sequence identity to SEQ ID NO:31. The polynucleotide comprises SEQ ID NO:33 (corresponding to K44R) or at least 80% sequence identity to SEQ ID NO:33. The polynucleotide comprises SEQ ID NO:35 (corresponding to D46E) or at least 80% sequence identity to SEQ ID NO:35. The polynucleotide comprises SEQ ID NO:39 (corresponding to D52E) or at least 80% sequence identity to SEQ ID NO:39. The polynucleotide comprises SEQ ID NO:47 (corresponding to R75K) or at least 80% sequence identity to SEQ ID NO:47. The polynucleotide comprises SEQ ID NO:55 (corresponding to D94E) or at least 80% sequence identity to SEQ ID NO:55.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The polynucleotide or polypeptide can be naturally occurring or non-naturally occurring (e.g., synthetic, recombinant, modified, and/or variant products). In one aspect, the naturally occurring or non-naturally occurring products are isolated or purified.

In one aspect, the term "isolated" encompasses products that have been removed from a biological environment (e.g., a cell, tissue, culture medium, body fluid, etc.), or otherwise increased in purity to any degree (e.g., isolated from a synthesis medium). Isolated products, thus, can be synthetic or naturally produced.

As used herein, the term "isolated," when referring to a nucleic acid or polypeptide refers to a state of purification or concentration different than that which occurs naturally. Any degree of purification or concentration greater than that which occurs naturally, including (1) the purification from other naturally occurring associated structures or compounds, or (2) the association with structures or compounds to which it is not normally associated in the body are within the meaning of "isolated" as used herein. The nucleic acids or polypeptides described herein may be isolated or otherwise associated with structures or compounds to which they are not normally associated in nature, according to a variety of methods and processed known to those of skill in the art. In one embodiment, the polypeptides described herein contain at most 5% (e.g., at most 4%, at most 3%, at most 2% at most 1%) by weight of other fungal proteins.

As used herein, "recombinant" refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide. "Recombinant means" also encompass the ligation of nucleic acids having various coding regions or domains or promoter sequences from different sources into an expression cassette or vector for expression of, e.g., inducible or constitutive expression of a fusion protein comprising a translocation domain of the invention and a nucleic acid sequence amplified using a primer of the invention.

"Modified" or "variant" products refer to products (e.g., polynucleotides or polypeptides) that have been altered from the original (e.g., naturally occurring) structure. As described herein, variants encompass polynucleotides or polypeptides with one or more changes to the nucleic acid or amino acid sequences, respectively. Changes includes modifications to the nucleic acid or amino acid sequence, including additions, deletions, insertions, and substitutions. Modified or variant products also can encompass disulfide bond formation, glycosylation, lipidation, acetylation, phosphorylation, or any other manipulation, such as conjugation with a labeling component, relative to the original structure.

As used herein, the terms "amplifying" and "amplification" refer to the use of any suitable amplification methodology for generating or detecting recombinant or naturally expressed nucleic acid, as described in detail, below. For example, the invention provides methods and reagents (e.g., specific degenerate oligonucleotide primer pairs) for amplifying (e.g., by polymerase chain reaction, PCR) naturally expressed (e.g., genomic or mRNA) or recombinant (e.g., cDNA) nucleic acids of the invention (e.g., taste stimulus-binding sequences of the invention) in vivo or in vitro.

The term "library" means a preparation that is a mixture of different nucleic acid or polypeptide molecules, such as the library of recombinantly generated Myd associated polynucleotides generated by amplification of nucleic acid with degenerate primer pairs, or an isolated collection of vectors that incorporate the amplified ligand-binding domains, or a mixture of cells each randomly transfected with at least one vector encoding a MYD.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are optionally directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "promoter" is defined as an array of nucleic acid sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "MYD family" can refer to polymorphic variants, including natural alleles, mutants, alleles, and interspecies homologs that encode polypeptides that: (1) have at least about 35 to 50% amino acid sequence identity, optionally about 60, 75, 80, 85, 90, 95, 96, 97, 98, or 99% amino acid sequence identity to SEQ ID NO:3 over a window of about 25 amino acids, optionally 50-100 amino acids.

The term "expression vector" or "expression cassette" refers to any recombinant expression system for the purpose of expressing a nucleic acid sequence of the invention in vitro or in vivo, constitutively or inducibly, in any cell, including prokaryotic, yeast, fungal, plant, insect or mammalian cell. The term includes linear or circular expression systems. The term includes expression systems that remain episomal or integrate into the host cell genome. The expression systems can have the ability to self-replicate or not, i.e., drive only transient expression in a cell. The term includes recombinant expression "cassettes which contain only the minimum elements needed for transcription of the recombinant nucleic acid.

By "host cell" is meant a cell that contains an expression vector and supports the replication or expression of the expression vector. Host cells may be prokaryotic cells such as *E. coli*, or eukaryotic cells such as yeast, insect, amphibian, or mammalian cells such as CHO, HeLa, HEK-293, and the like, e.g., cultured cells, explants, and cells in vivo.

In one embodiment, the host cell is selected from the group consisting of *Escherichia coli, Klebsiella oxytoca, Anaerobiospirillum succiniciproducens, Actinobacillus succinogenes, Mannheimia succiniciproducens, Agrobacterium tumefaciens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens, Pseudomonas putida, Saccharomyces cerevisiae, Schizosaccharomyces pombe, Kluyveromyces lactis, Kluyveromyces marxianus, Aspergillus terreus, Aspergillus niger, Pichia pastoris, Rhizopus arrhizus, Rhizopus oryzae, Yarrowia lipolytica, Candida albicans, Issatchenkia orientalis, Scheffersomyces stipitis, Yarrowia lipolytica, Ogataea polymorpha, Phaffia rhodozyma, Candida utilis, Arxula adeninivorans, Debaryomyces hansenii, Debaryomyces polymorphus*, and *Schwanniomyces occidentalis*.

In another aspect, the host cell is selected from the group consisting of gram-positive no-spore forming bacteria, gram-positive spore forming bacteria, gram negative bacteria, yeast, and protists/algae.

Non-limiting examples of gram-positive no-spore forming bacteria include *Bifidobacterium adolescentis, Bifidobacterium animalis, Bifidobacterium bifidum, Bifidobacterium breve, Bifidobacterium longum, Carnobacterium divergens, Corynebacterium ammoniagenes, Corynebacterium glutamicum, Lactobacillus acidophilus, Lactobacillus amylolyticus, Lactobacillus amylovorus, Lactobacillus animalis, Lactobacillus alimentarius, Lactobacillus aviaries, Lactobacillus brevis, Lactobacillus buchneri, Lactobacillus casei, Lactobacillus cellobiosus, Lactobacillus collinoides, Lactobacillus coryniformis, Lactobacillus crispatus, Lactobacillus curvatus, Lactobacillus delbrueckii, Lactobacillus dextrinicus, Lactobacillus diolivorans, Lactobacillus farciminis, Lactobacillus fermentum, Lactobacillus gallinarum, Lactobacillus gasseri, Lactobacillus helveticus, Lactobacillus hilgardii, Lactobacillus johnsonii, Lactobacillus kefiranofaciens, Lactobacillus kefiri, Lactobacillus mucosae, Lactobacillus panis, Lactobacillus paracasei, Lactobacillus parafarraginis, Lactobacillus paraplantarum, Lactobacillus pentosus, Lactobacillus plantarum, Lactobacillus pontis, Lactobacillus reuteri, Lactobacillus rhamnosus, Lactobacillus sakei, Lactobacillus salivarius, Lactobacillus sanfranciscensis, Lactococcus lactis, Leuconostoc citreum, Leuconostoc lactis, Leuconostoc mesenteroides, Leuconostoc pseudomesenteroides, Microbacterium imperial, Oenococcus oeni, Pasteuria nishizawae, Pediococcus acidilactic, Pediococcus parvulus, Pediococcus pentosaceus, Propionibacterium acidipropioni, Propionibacterium freudenreichii*, and *Streptococcus thermophiles*.

Non-limiting examples of gram-positive spore forming bacteria include *Bacillus amyloliquefaciens, Bacillus atrophaeus, Bacillus circulans, Bacillus clausii, Bacillus coagulans, Bacillus flexus, Bacillus fusiformis, Bacillus lentils, Bacillus licheniformis, Bacillus megaterium, Bacillus mojavensis, Bacillus pumilus, Bacillus smithii, Bacillus subtilis, Bacillus vallismortis, Bacillus velezensis, Geobacillus stearothermophilus, Paenibacillus illinoisensis*, and *Parageobacillus thermoglucosidasius*. Non-limiting examples of gram negative bacteria include *Cupriavidus necator, Gluconobacter oxydans, Komagataeibacter sucrofermentans*, and *Xanthomonas campestris*.

Non-limiting examples of yeast include *Candida cylindracea, Debaryomyces hansenii, Hanseniaspora uvarum, Kluyveromyces lactis, Kluyveromyces marxianus, Komagataella pastoris, Komagataella phaffi, Lindnera jadinii, Ogataea angusta, Saccharomyces bayanus, Saccharomyces cerevisiae, Saccharomyces pastorianus, Schizosaccharomyces pombe, Wickerhamomyces anomalus, Xanthophyllomyces dendrorhous, Yarrowia lipolytica*, and *Zygosaccharomyces rouxii*.

Non-limiting examples of protists/algae include *Aurantiochytrium limacinum, Euglena gracilis*, and *Tetraselmis chuii*.

The Myd proteins described herein also include "analogs," or "conservative variants" and "mimetics" ("peptidomimetics") with structures and activity that substantially correspond to the exemplary sequences. Thus, the terms "conservative variant" or "analog" or "mimetic" refer to a polypeptide which has a modified amino acid sequence, such that the change(s) do not substantially alter the polypeptide's (the conservative variant's) structure and/or activity, as defined herein. These include conservatively modified variations of an amino acid sequence, i.e., amino acid substitutions, additions or deletions of those residues that are not critical for protein activity, or substitution of amino acids with residues having similar properties (e.g., acidic, basic, positively or negatively charged, polar or non-polar, etc.) such that the substitutions of even critical amino acids does not substantially alter structure and/or activity.

More particularly, "conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein.

For instance, the codons GCA, GCC, GCG and GCU all encode the amino acid alanine. Thus, at every position where an alanine is specified by a codon, the codon can be altered to any of the corresponding codons described without altering the encoded polypeptide.

Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

Conservative substitution tables providing functionally similar amino acids are well known in the art. For example, one exemplary guideline to select conservative substitutions includes (original residue followed by exemplary substitution): ala/gly or ser; arg/lys; asn/gln or his; asp/glu; cys/ser; gln/asn; gly/asp; gly/ala or pro; his/asn or gln; ile/leu or val; leu/ile or val; lys/arg or gln or glu; met/leu or tyr or ile; phe/met or leu or tyr; ser/thr; thr/ser; trp/tyr; tyr/trp or phe; val/ile or leu. An alternative exemplary guideline uses the following six groups, each containing amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (I); 5) Isoleucine (I), Leucine (L), Methionine (M), Valine (V); and 6) Phenylalanine (F), Tyrosine (Y), Tryptophan (W); (see also, e.g., Creighton, Proteins, W.H. Freeman and Company (1984); Schultz and Schimer, Principles of Protein Structure, Springer-Verlag (1979)). Another alternative exemplary guidelines uses the following six groups, where proline is unique: 1) Gly (G), Ala (A), Val (V), Leu (L), Ile (I); 2) Ser (S), Cys (C), Thr (T), Met (M); 3) Pro (P); 4) Phe (F), Tyr (Y), Try (W); 5) His (H), Lys (K), Arg (R); and 6) Asp (D), Glu (E), Gln (N). One of skill in the art will appreciate that the above-identified substitutions are not the only possible conservative substitutions. For example, for some purposes, one may regard all charged amino acids as conservative substitutions for each other whether they are positive or negative. In addition, individual substitutions, deletions or additions that alter, add or delete a single amino acid or a small percentage of amino acids in an encoded sequence can also be considered "conservatively modified variations." One of skill in the art would be familiar with codon selection in a given host that is expressing the protein of interest.

The terms "mimetic" and "peptidomimetic" refer to a synthetic chemical compound that has substantially the same structural and/or functional characteristics of the polypeptides, e.g., translocation domains, ligand-binding domains, or chimeric receptors of the invention. The mimetic can be either entirely composed of synthetic, non-natural analogs of amino acids, or may be a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity.

As with polypeptides of the invention which are conservative variants, routine experimentation will determine whether a mimetic is within the scope of the invention, i.e., that its structure and/or function is not substantially altered. Polypeptide mimetic compositions can contain any combination of non-natural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. A polypeptide can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(O)—CH$_2$— for —C(O)—NH—), aminomethylene (CH$_2$—NH), ethylene, olefin (CH=CH), ether (CH$_2$—O), thioether (CH—S), tetrazole (CN$_4$), thiazole, retroamide, thioamide, or ester (see, e.g., Spatola, Chemistry and Biochemistry of Amino Acids, Peptides and Proteins, Vol. 7, pp 267-357, "Peptide Backbone Modifications," Marcell Dekker, NY (1983)). A polypeptide can also be characterized as a mimetic by containing all or some non-natural residues in place of naturally occurring amino acid residues; non-natural residues are well described in the scientific and patent literature. Phyre2 is a suite of tools available on the web to predict and analyze protein structure, function and mutations.

A protein folding analysis is performed using tools including PHYRE Protein Homology/analogY Recognition Engine V 2.0 and JPred, a Protein Secondary Structure Prediction server. These tools reveal that SEQ ID NO:3 predicts a β sheet-dominated globular-type protein with significant sections of β-sheet and some short sections of α-helix. Specifically, the Jpred tool predicts putative β sheet from about residues 5-11, 16-19, 28-29, 39-40, 61-67, 71-77, and 98-101; and α-helix from about residues 20-25, 45-55, 111-119 of SEQ ID NO:3; the PHYRE tool predicts β sheet from about residue 5 to 12, 17-32, 38-40, 45-57, 62-66, 73-81, 98-104, and 112-116 and α-helix from about residue 84 to 89 and 116-118 of SEQ ID NO:3. See FIG. 1.

Examples of conservatively modified variations of Myd1 protein structure may be derived using homology-modelling algorithms: SWISS-MODEL, PHYRE2.0, and Jpred to identify a sequence-based consensus loop regions, as known in the art, see, e.g., Pechmann, S. & Frydman, J. Interplay between Chaperones and Protein Disorder Promotes the Evolution of Protein Networks. PLoS Computational Biology 10, e1003674 (2014).

Alternative protein sequences with putative similar structure and function to Myd1 are provided herein as SEQ ID NO:8 through SEQ ID NO:17. To derive SEQ ID NO:8 to SEQ ID NO:17, the consensus loop region was chosen as sites of mutation as most insertions and deletions are usually found in regions between secondary structure elements, where they can be accommodated easier without major distortions in the overall fold of the protein. The core of this protein has a higher degree of sequence conservation as was found within 4JOX.

Out of the 29 possible amino acid locations within the consensus loop region, 12 amino acids were substituted using conservative replacements. If selected for mutation, the wild type amino acid was given an equal probability among the conservative amino acid residues. (Gly can be replaced with Ala, Cys, Asp, Glu, or Arg with an equal 20% probability).

Specific regions of the MYD/Myd nucleotide and amino acid sequences may be used to identify polymorphic variants, interspecies homologs, and alleles of Myd family members. This identification can be made in vitro, e.g., under stringent hybridization conditions or PCR (e.g., using primers encoding the Myd sequences identified herein), or by using the sequence information in a computer system for comparison with other nucleotide sequences. Different alleles of MYD genes within a single species population will also be useful in determining whether differences in allelic sequences correlate to differences in taste perception between members of the population. Classical PCR-type amplification and cloning techniques are useful for isolating orthologs, for example, where degenerate primers are sufficient for detecting related genes across species.

For instance, primers designed using the sequences disclosed herein can be used can be used to amplify and clone MYD-related genes from different fungal genomes. In contrast, genes within a single species that are related to MYD are best identified using sequence pattern recognition software to look for related sequences. Typically, identification of polymorphic variants and alleles of MYD family members can be made by comparing an amino acid sequence of about 25 amino acids or more, e.g., 50-100 amino acids. Amino acid identity of approximately at least 35 to 50%, and optionally 60%, 70%, 75%, 80%, 85%, 90%, 95-99%, or above typically demonstrates that a protein is a polymorphic variant, interspecies homolog, or allele of a MYD family member. Sequence comparison can be performed using any of the sequence comparison algorithms discussed below. Antibodies that bind specifically to Myd polypeptides or a conserved region thereof can also be used to identify alleles, interspecies homologs, and polymorphic variants.

Nucleotide and amino acid sequence information for MYD family members may also be used to construct models of sweet modulating polypeptides in a computer system and how they interact with sweet receptors and computer system models of same. Sweet taste receptors are composed of a heterodimer of taste 1 receptor member 2 (T1R2) and taste 1 receptor member 3 (T1R3). These models can be subsequently used to identify variants and mutations of Myd that can increase activation of sweet receptors and identify more active versions of Myd.

Various conservative mutations and substitutions are envisioned to be within the scope of the invention. For instance, it would be within the level of skill in the art to perform amino acid substitutions using known protocols of recombinant gene technology including PCR, gene cloning, site-directed mutagenesis of cDNA, transfection of host cells, and in-vitro transcription. The variants could then be screened for taste receptor agonist functional activity.

In one embodiment, hybrid protein-coding sequences comprising nucleic acids encoding Myds fusion proteins may be constructed. These nucleic acid sequences can be operably linked to transcriptional or translational control elements, e.g., transcription and translation initiation sequences, promoters and enhancers, transcription and translation terminators, polyadenylation sequences, and other sequences useful for transcribing DNA into RNA. Fusion proteins may include C-terminal or N-terminal translocation sequences. Further, fusion proteins can comprise additional elements, e.g., for protein detection, purification, or other applications. Detection and purification facilitating domains include, e.g., metal chelating peptides such as polyhistidine tracts, histidine-tryptophan modules, or other domains that allow purification on immobilized metals; maltose binding protein; protein A domains that allow purification on immobilized immunoglobulin; or the domain utilized in the FLAGS extension/affinity purification system (Immunex Corp, Seattle Wash.).

In one embodiment, the fusion protein comprises a peptide or protein tag (e.g., for protein purification or detection). Peptide/protein tags are known in the art, such as those described in Johnson, "Protein/Peptide Tags," DOI//dx-.doi.org/10.13070/mm.en.2.116 including but not limited to green fluorescent protein (GFP), FLAG, Myc epitope, polyhistidine, glutathione-S-transferase (GST), HA, V5, ABDz1-tag, Adenylate kinase (AK-tag), BC2-tag, Calmodulin-binding peptide, CusF, Fc, Fhb, Halo tag, Heparin binding peptide (HB-tag), Ketosteroid isomerase (KSI), maltose-binding protein (MBP), thioredoxin, PA(NZ-1), Poly-Arg, Poly-Lys, S-tag, SBP/Streptavidin-Binding Peptide, SNAP, Strep-II (Twin-Strep), and SUMO/SUMO2.

Affinity tags are a type of protein tag that is appended to proteins so that they can be purified from their crude biological source using an affinity technique. Affinity tags are known in the art, such as those described in Kimple et al. Curr Protoc Protein Sci.; 73: Unit-9.9. doi:10.1002/0471140864.ps0909s73. These include polyhistidine, GST, MBP, Calmodulin-binding peptide, intein-chitin binding domain, Streptavidin/Biotin-based tags, and His-Patch Thio-Fusion (thioredoxin). Affinity tags include small (e.g., 20 or less amino acid residues) or large affinity tags. Examples of small affinity tags include His, FLAG, Strep II, and S-peptide, and examples of large affinity tags include MBP, GST, cellulose binding domains, calmodulin binding peptide, and His-patch thioredoxin.

Affinity tags include epitope tags and reporter tags. Reporter tags serve as reporters of protein expression and protein-protein interaction. Reporter tags include, but are not limited to, enzymes such as β-galactosidase (β-gal), alkaline phosphatase (AP), chloramphenicol acetyl transferase (CAT), and horseradish peroxidase (HRP).

Epitope tags include FLAG, hemagglutinin (HA), c-myc, T7, and Glu-Glu, which are used for the detection of fusion proteins in vitro and in cell culture. Their short, linear recognition motifs rarely affect the properties of the protein of interest and are usually very specific for their respective primary antibodies. If the anti-myc antibody is used, specificity can be increased by using an enzyme-linked secondary antibody to detect a conjugated anti-myc primary antibody instead of using an HRP- or AP-anti-myc conjugate alone.

Tags can be at either end of the target protein. Some epitope tags, such as FLAG, are often used in tandem to increase their desired features, or in combination with another tag, such as in the construct of His-Myc and His-V5.

Tandem affinity purification (TAP) is a dual-affinity purification method based on the fusion of two affinity tags to a protein of interest, which allows purification of a tagged protein and isolation of protein complexes interacting with the protein of interest. The use of TAP is encompassed within the present invention.

In one embodiment, the fusion protein comprises a histidine tag that comprises 2-10 (e.g., 2, 3, 4, 5, 6, 7, 8, 9, or 10) histidine residues. For example, the histidine tag can comprise 6 histidine residues.

The inclusion of a cleavable linker sequences such as Factor Xa (see, e.g., Ottavi, Biochimie 80:289-293 (1998)), subtilisin protease recognition motif (see, e.g., Polyak, Protein Eng. 10:615-619 (1997)); enterokinase (Invitrogen, San Diego, Calif.), and the like, between the translocation domain (for efficient plasma membrane expression) and the rest of the newly translated polypeptide may be useful to facilitate purification. For example, one construct can include a polypeptide encoding a nucleic acid sequence linked to six histidine residues followed by a thioredoxin, an enterokinase cleavage site (see, e.g., Williams, Biochemistry 34:1787-1797 (1995)), and an C-terminal translocation domain. The histidine residues facilitate detection and purification while the enterokinase cleavage site provides a means for purifying the desired protein(s) from the remainder of the fusion protein. Technology pertaining to vectors encoding fusion proteins and application of fusion proteins are well described in the scientific and patent literature, see, e.g., Kroll, DNA Cell. Biol. 12:441-53 (1993).

The fusion protein can contain one or more linkers (e.g., flexible linkers, rigid linkers, and in vivo cleavable linkers). Besides the basic role in linking the functional domains together (as in flexible and rigid linkers) or releasing free functional domain in vivo (as in in vivo cleavable linkers), linkers offer many other advantages for the production of fusion proteins, such as improving biological activity, increasing expression yield, and achieving desirable pharmacokinetic profiles. Linkers are known in the art (see, e.g., Chen et al., Adv Drug Deliv Rev. 65(10): 1357-1369 (2013)).

Flexible linkers are used when the joined domains require a certain degree of movement or interaction. They are generally composed of small, non-polar (e.g. Gly) or polar (e.g. Ser or Thr) amino acids. The small size of these amino acids provides flexibility, and allows for mobility of the connecting functional domains. The incorporation of Ser or Thr can maintain the stability of the linker in aqueous solutions by forming hydrogen bonds with the water molecules, and therefore reduces the unfavorable interaction between the linker and the protein moieties.

The most commonly used flexible linkers have sequences consisting primarily of stretches of Gly and Ser residues ("GS" linker). An example of the most widely used flexible linker has the sequence of (Gly-Gly-Gly-Gly-Ser)$_n$ (SEQ ID NO:69). By adjusting the copy number "n", the length of this GS linker can be optimized to achieve appropriate separation of the functional domains, or to maintain necessary inter-domain interactions. Besides the GS linkers, many other flexible linkers have been designed for recombinant fusion proteins. These flexible linkers are also rich in small or polar amino acids such as Gly and Ser, but can contain additional amino acids such as Thr and Ala to maintain flexibility, as well as polar amino acids such as Lys and Glu to improve solubility.

Rigid linkers keep a fixed distance between the domains and to maintain their independent functions. Examples of rigid linkers include alpha helix-forming linkers with the sequence of (EAAAK)$_n$ (SEQ ID NO:70) and linkers with a Pro-rich sequence, (XP)$_n$, with X designating any amino acid, preferably Ala, Lys, or Glu.

The polypeptide of the present invention also can contain a signal peptide (i.e., a signal sequence, targeting signal, localization signal, localization sequence, transit peptide, leader sequence, or leader peptide), which is a short peptide present at the N-terminus or occasionally C-terminus of most newly synthesized proteins that are destined toward the secretory pathway. These proteins include those that reside either inside certain organelles (the endoplasmic reticulum, Golgi or endosomes), secreted from the cell, or inserted into most cellular membranes. Exemplary signal peptides are known in the art and a person of ordinary sill in the art would recognize how to select a particular signal peptide for use in the invention.

As used herein, "at least 80% identity" with reference to an amino acid sequence or a nucleotide sequence refers to 80%, 81%, 82%, 83%, 84%, 85%, 86%, 87%, 88%, 89%, 90%, 91%, 92%, 93%, 94%, 95%, 96%, 97%, 98%, or 99% or more identity.

As used herein, examples of "an amino acid sequence modified by deletion, insertion, substitution, or addition of one or more amino acids" include an amino acid sequence modified by deletion, insertion, substitution, or addition of 1 or more to 30 or less, preferably 20 or less, more preferably 10 or less, and further preferably 5 or less amino acids (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or any ranges thereof). As used herein, examples of "a nucleotide sequence modified by deletion, insertion, substitution, or addition of one or more nucleotides" include a nucleotide sequence modified by deletion, insertion, substitution, or addition of 1 or more to 90 or less, preferably 60 or less, more preferably 30 or less, further preferably 15 or less, and further more preferably 10 or less nucleotides (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, or any ranges thereof).

For example, in sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, as described below for the BLASTN and BLASTP programs, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J Mol. Biol. 48:443 (1970), by the search for similarity method of Pearson & Lipman, Proc. Natl. Acad Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

A preferred example of an algorithm that is suitable for determining percent sequence identity and sequence similarity are the BLAST and BLAST 2.0 algorithms, which are described in Altschul at al., Nuc. Acids Res. 25:3389-3402 (1977) and Altschul et al., J Mol. Biol. 215:403-410 (1990), respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., Altschul et al., Nuc. Acids Res. 25:3389-3402 (1977) and Altschul et al., J Mol. Biol. 215:403-410 (1990)). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad Sci. USA 89:10915 (1989)) alignments (B) of 50, expectation (E) of 10, M=5, N=−4, and a comparison of both strands.

Another example of a useful algorithm is PILEUP. PILEUP creates a multiple sequence alignment from a group of related sequences using progressive, pairwise alignments to show relationship and percent sequence identity. It also plots a so-called "tree" or "dendogram" showing the clustering relationships used to create the alignment (see, e.g., FIG. 2). PILEUP uses a simplification of the progressive alignment method of Feng & Doolittle, J Mol. Evol. 35:351-360 (1987). The method used is similar to the method described by Higgins & Sharp, CABIOS 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., Nuc. Acids Res. 12:387-395 (1984) encoded by the genes were derived by conceptual translation of the corresponding open reading frames.

The polynucleotides encoding the polypeptides of the present invention can be synthesized chemically or by genetic engineering based on the amino acid sequence of a Myd. For example, the polynucleotide can be synthesized chemically based on the amino acid sequence of the polypeptides of the present invention or preprotein thereof. A contract synthesis service of nucleic acid (provided from, for example, Medical & Biological Laboratories Co., Ltd., Genscript, etc.) can be used for the chemical synthesis of the polynucleotide. Further, the synthesized polynucleotide can be amplified by PCR and cloning, etc.

The polypeptides of the present invention can be produced, for example, by expressing a gene encoding a Myd polypeptide of the present invention. Preferably, a Myd polypeptide of the present invention can be produced from a transformant in which the polynucleotide encoding a Myd polypeptide of the present invention is introduced. For example, a Myd polypeptide of the present invention is produced from a polynucleotide encoding a Myd polypeptide of the present invention introduced in a transformant after a polynucleotide encoding a Myd polypeptide of the present invention or a vector comprising it is introduced into a host to obtain a transformant and the transformant is cultured in an appropriate medium. The proteins of the present invention can be obtained by isolating or purifying the produced Myd polypeptide from the culture.

Therefore, the present invention further provides a polynucleotide encoding a Myd polypeptide of the present invention and a vector comprising it. The present invention further provides a method of manufacturing a transformant, comprising introducing a polynucleotide encoding a Myd polypeptide of the present invention or a vector comprising it into a host. The present invention further provides a transformant comprising a polynucleotide encoding a Myd polypeptide of the present invention or a vector comprising it introduced from the outside of a cell. The present invention further provides a method of manufacturing a Myd polypeptide of the present invention, comprising culturing the transformant.

The present invention also includes the polynucleotides of the invention, operably linked to a heterologous regulatory element. The invention may include an expression cassette or vector comprising the polynucleotides of the present invention, and a host cell transformed with a vector of the invention.

Alternatively, the polynucleotide encoding a Myd polypeptide of the present invention can be produced by introducing a mutation into the polynucleotide synthesized according to the procedure with known mutagenesis methods such as the ultraviolet irradiation and site-directed mutagenesis. For example, the polynucleotide encoding the polypeptides of the present invention can be obtained by introducing a mutation into the polynucleotide of SEQ ID NO:1 or SEQ ID NO:2 with a known method, expressing the obtained polynucleotide, investigating the expressed protein's sweet-modification activity, and selecting a polynucleotide encoding the protein having desired sweet modification activity.

Site-directed mutagenesis of a polynucleotide can be performed with any methods such as, for example, inverse PCR and annealing (Muramatsu et al. edit., "Revised 4th edition New genetic engineering handbook", YODOSHA, p. 82-88). A variety of commercially available kits for site-directed mutagenesis such as QuickChange II Site-Directed Mutagenesis Kit from Stratagene and QuickChange Multi Site-Directed Mutagenesis Kit can be used as needed.

Examples of the type of a vector comprising the polynucleotide encoding the polypeptides of the present invention include, without limitation, a vector usually used for gene cloning, for example, a plasmid, a cosmid, a phage, a virus, a YAC and a BAC. Examples of vectors include plasmids (e.g., DNA plasmids), yeast (e.g., *Saccharomyces*), and viral vectors, such as poxvirus, retrovirus, adenovirus, adeno-associated virus, herpes virus, polio virus, alphavirus, baculovirus, Sindbis virus, plant viruses (e.g., Alphaflexiviridae or Potyviridae), and insect viruses (e.g., Baculoviridae).

Among these, a plasmid vector is preferred and for example a commercially available plasmid vector for protein expression, for example, pUC19, pUC118, pUC119, pBR322 etc. (all of which are from TAKARA BIO INC.) can be used.

The vector can comprise a DNA region comprising a replication initiation region or a replication origin of DNA. Alternatively, a regulatory sequence such as a promoter region for initiating transcription of the gene, a terminator region or a secretory signal region for secreting an expressed protein to the outside of a cell can be operably liked to the upstream of the polynucleotide encoding the proteins of the present invention (i.e. the MYD gene of the present invention) in the vector. As used herein, a gene and a regulatory sequence being "operably liked" refers to a condition in which the gene and the regulatory region are positioned so that the gene can be expressed under the regulation by the regulatory region.

The type of the regulatory sequence of a promoter region, a terminator, and a secretory signal region etc. is not specifically limited, and a promoter and a secretory signal sequence usually used can be selected to use as appropriate depending on the host into which the sequence is introduced. For example, preferred examples of the regulatory sequence which can be incorporated to the vector of the present invention include the cbh1 promoter sequence derived from *Trichoderma reesei* (Curr, Genet, 1995, 28 (1): 71-79).

Alternatively, a marker gene to select a host into which the vector is appropriately introduced (for example, a resistance gene to an agent such as ampicillin, neomycin, kanamycin and chloramphenicol) can be further incorporated into the vector of the present invention. Alternatively, a gene encoding a synthase of a required nutrient can be incorporated into the vector as a marker gene, when an auxotrophic strain is used as a host. Alternatively, a related gene of the metabolism can be incorporated into the vector as a marker gene, when a selective medium requiring specific metabolism for growth is used. Examples of such a metabolism related gene include an acetamidase gene for using acetamide as a nitrogen source.

Ligation between the polynucleotide encoding a Myd polypeptide of the present invention and a regulatory sequence and a marker gene can be performed by a known method in the art such as SOE (splicing by overlap extension)—PCR (Gene, 1989, 77: 61-68). The procedure for introducing a ligated fragment into a vector is known in the art.

Examples of a host of a transformant into which the vector is introduced include a microorganism such as a bacterium and filamentous fungus. Examples of the bacterium include *Escherichia coli* and a bacterium belonging to *Staphylococcus, Enterococcus, Listeria* and *Bacillus*, of which *Escherichia coli* and *Bacillus* bacteria (for example, *Bacillus subtilis* or a mutant thereof) are preferred. Examples of the *Bacillus subtilis* mutant can include protease 9 double deficient strain KA8AX described in J. Biosci. Bioeng., 2007, 104 (2): 135-143 and a DBPA strain, a mutant from protease 8 double deficient strain described in Biotechnol. Lett., 2011, 33 (9): 1847-1852, of which protein folding efficiency is improved. Examples of the filamentous fungus include *Trichoderma, Aspergillus* and *Rhizopus*. Also, for example, *Pichia pastoris, Saccharomyces cerevisiae, Hansenula polymorpha, Yarrowia lipolytica, Schizosaccharomyces pombe, Kluyveromyces lactis* are appropriate expression hosts. In yet another aspect, the invention includes a host cell comprising one or more of the expression cassettes described herein operably linked to control elements compatible with expression in the cell. The cell can be, for example, a mammalian cell (e.g., BHK, VERO, HT1080, 293, RD, COS-7, or CHO cells), an insect cell (e.g., *Trichoplusia ni* (Tn5) or Sf9), a bacterial cell, a plant cell, or a yeast cell.

The recombinantly expressed polypeptides from Myd-encoding expression cassettes are typically isolated from lysed cells or culture media. Purification can be carried out by methods known in the art including salt fractionation, ion exchange chromatography, gel filtration, size-exclusion chromatography, size-fractionation, and affinity chromatography. Immunoaffinity chromatography can be employed using antibodies generated based on, for example, Gag antigens.

The invention provides a method of purifying a polypeptide having sweet-taste modulation activity comprising (a) obtaining a composition comprising the polypeptide, and (b) purifying the composition via hydrophobic interaction chromatography (HIC) followed by size exclusion chromatography (SEC). In one aspect, the polypeptide comprises an amino acid sequence having at least 80% sequence identity to a polypeptide selected from the group consisting of SEQ ID NO:3, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, and SEQ ID NO:17. In another aspect, the polypeptide has a polypeptide sequence having at least 80% sequence identity to a polypeptide sequence selected from the group consisting of SEQ ID NO:3, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, and SEQ ID NO:17; (a) wherein the polypeptide contains at least one substitution modification relative to the polypeptide sequence selected from the group consisting of SEQ ID NO:3, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, and SEQ ID NO:17, wherein the polypeptide is not the polypeptide of SEQ ID NO:3, or (b) wherein the polypeptide further comprises a histidine tag, wherein the polypeptide has sweet-taste modulation activity.

One of skill in the art is familiar with the purification techniques of hydrophobic interaction chromatography (HIC) and size exclusion chromatography (SEC), including the selection of appropriate columns, buffers, and eluting solutions. Exemplary HIC and SEC purification techniques are described herein in Example 11. In an exemplary aspect, the purify of the polypeptide following purification by HIC and SEC is at least 90%, at least 91%, at least 92%, at least 93%, at least 94%, at least 95%, at least 96%, at least 97%, at least 98%, at least 99%, or any ranges of values thereof.

The invention also contemplates a transgenic plant comprising a heterologous polynucleotide and/or heterologous polypeptide of the invention as described herein. The plant has an altered phenotype due to the expression of the heterologous nucleic acid sequence. The altered phenotype may include a phenotype with increased sweetness in any plant part, including fruits. The transgenic plant may contain an expression cassette as defined herein as a part of the plant, the cassette having been introduced by transformation of a plant with a vector of this invention. Such expression cassettes include regulatory sequences for expression of heterologous coding sequences in plants, including plant-expressible promoters and terminators. A transgenic plant can be any type of plant which can express the heterologous nucleic acid sequences described herein. The term "plant" includes whole plants, plant organs (e.g., leaves, stems, roots, etc.), seeds and plant cells and progeny of same. The class of plants which can be used in the method of the invention is generally as broad as the class of higher plants amenable to transformation techniques, including both monocotyledonous (monocots) and dicotyledonous (dicots) plants. It includes plants of a variety of ploidy levels, including polyploid, diploid and haploid. For example, the transgenic plant can be an apple or strawberry.

Techniques for transforming a wide variety of plant species are well known in the art and described in the technical and scientific literature. See, for example, Weising et al. (1988) *Ann. Rev. Genet.*, 22:421-477 and Joung et al. (2015) "Plant Transformation Methods and Applications," in Current Technology in Plant Molecular Breeding, (Koh et al., eds) Springer Dordrecht Heidelberg New York London, Chapter 9, pages 297-344. Any method known in the art for transformation of plant cells, including plant protoplasts, or plant tissue can be employed for plant transformation. Specific methods for plant transformation include among others, bolistic methods (gene guns), electroporation, micro-injection, protoplast fusion and *Agrobacterium*-mediated transformation. *Agrobacterium*-mediated transformation can, for example, employ binary vectors that replicate in *Escherichia coli* and *Agrobacterium tumefaciens* or other *Agrobacterium* strains. A variety of such binary vectors are known in the art and can be employed to introduce heterologous polynucleotides into plant cells and plant tissue. Plant expression vectors which include regulatory sequences for expression of heterologous coding sequences, including plant-expressible promoter sequences and other plant regulatory sequences, in plant cells and plant tissue are known in the art and can be employed to transform plants to express polypeptides as described herein.

A variety of plant-expressible promoters are known in the art and are available for use in heterologous constructs, vectors and transformed plant materials herein which contain polynucleotides encoding protein having sweet-taste modulation activity. Plant-expressible promoters can derive from natural plant sources, plant virus sources and from bacteria, such as *Agrobacterium* strains, having promoters that are plant-expressible. Plant-expressible promoters include, among others, Cauliflower Mosaic Virus promoter (CaMV 35S), octopine and nopaline synthase promoters (e.g., nos promoter), plant ubiquitin promoter (Ubi), rice actin promoter (Act-1), and maize alcohol dehydrogenase (Adh-1). Plant-expressible promoters include constitutive promoters, inducible promoters, tissue-specific promoters, developmental stage-specific promoters and examples of each type of promoter are known in the art. Tissue-specific promoters include, among others, those that direct expression in plant roots, plant leaves, fruit, flowers, pollen or cells engaged in active photosynthesis (e.g., phosphoenolpyruvate promoters (PEP)). Development stage-specific promoters include those that direct expression during fruit ripening, flowering or seed set. Synthetic plant promoters are also known in the art and are useful in heterologous constructs, vectors and transformed plant materials (see, e.g., Ali S. & Kim W-C (2019) Frontiers in Plant Science, 10, article 1433).

Techniques for regeneration of plants from transformed protoplasts, plant cells, callus, or other plant tissue are well known in the art and can be employed to regenerated whole plants and plant parts from such transformed plant material. Regeneration methods include organogenesis and embryogenesis. See: *Handbook of plant cell culture. Volume 1: Techniques for propagation and breeding* (1983) Edited by D. A. Evans et al., Macmillan (New York); R. H. Smith, *Plant Tissue Culture: Techniques and Experiments*, 3$^{rd}$ Edition (2012) Academic Press (New York); M. R. Davey & P. Anthony, Plant Cell Culture: Essential Methods (2010) John Wiley & Sons (New York), particularly Chapters 3 and 9.

A method usually used in the field such as protoplast method and electroporation can be used as a method of introducing a vector into a host. A transformant of interest can be obtained by selecting a strain in which a vector is appropriately introduced using an index such as the expression of a marker gene and/or auxotrophy.

Alternatively, a fragment in which the polynucleotide encoding a Myd polypeptide of the present invention, a regulatory sequence and a marker gene are ligated can be directly introduced into the genome of a host. For example, the polynucleotide encoding a Myd polypeptide of the present invention is introduced into the genome of a host by constructing a DNA fragment added with a sequence complementary to the genome of the host at both ends of the ligated fragment, introducing the fragment into the host and inducing homologous recombination between the host genome and the DNA fragment by SOE-PCR.

Culturing the thus obtained transformant, in which the polynucleotide encoding a Myd polypeptide of the present invention or a vector comprising it is introduced, in an appropriate medium results in the expression of the MYD cDNA on the vector, and then the production of a Myd polypeptide of the present invention. The medium used for the culture of such transformant can be selected depending on the type of the microorganism of such transformant by those skilled in the art as appropriate.

Alternatively, a Myd polypeptide of the present invention can be expressed from the polynucleotide encoding a Myd polypeptide of the present invention or a transcription product thereof using a cell-free translation system. "Cell-free translation system" refers to an in vitro transcription-translation system or an in vitro translation system constructed by adding reagents such as amino acids required for the translation of a protein into a suspension obtained by mechanically destructing cells to be a host.

A Myd polypeptide of the present invention produced in the culture or cell-free translation system can be isolated or purified by using a general method used for the purification of a protein, for example, centrifugation, ammonium sulfate precipitation, gel chromatography, ion-exchange chromatography and affinity chromatography etc. alone or in combination as appropriate. Here, when the gene encoding a Myd polypeptide of the present invention and the secretory signal sequence are operably liked on the vector within the transformant, the produced Myd polypeptide can be collected more easily from the culture because the Myd polypeptide is secreted to the outside of a cell. The Myd polypeptide collected from the culture can be further purified with known means.

The present invention also includes a method for producing a protein having sweet-taste modulation activity, comprising culturing the host cells of the invention in a medium under conditions that result in producing the protein having sweet-taste modulation activity, similar to a known sweet flavoring agent or compound.

As used herein, a "sweet flavoring agent," "sweet compound" or "sweet receptor activating compound" refers to a composition that elicits a detectable sweet flavor in a subject, e.g., sucrose, fructose, glucose, and other known natural saccharide-based sweeteners, or known artificial sweeteners such as saccharine, cyclamate, aspartame, and the like as is further discussed herein, or a material that activates a T1R2/T1R3 receptor in vitro. The subject may be a human or an animal.

A sweet flavoring agent or sweetening composition may be used in an effective amount, which refers to an amount of a sweetening composition of the invention that is sufficient to induce sweet taste in a subject when present in a product for oral administration.

In an embodiment, the instant sweet proteins are capable of sweet-taste modulation activity. Myd polypeptides of the invention may have e.g., functional, physical and chemical effects at taste receptors, such as sweet taste receptors. "Sweet-taste modulation activity" may refer to inhibitory, activating, e.g., agonist or antagonist properties of a polypeptide of the invention, identified using in vitro and in vivo assays for taste transduction. Proteins with inhibitory activity may bind to, partially or totally block stimulation, decrease, prevent, delay activation, inactivate, desensitize, or down regulate taste transduction, e.g., antagonists. Activating polypeptides may bind to, stimulate, increase, open, activate, facilitate, enhance activation, sensitize, or up regulate taste transduction, e.g., agonists. Activating polypeptides are preferred.

Sweet taste modulation also refers to enhancing the taste, such as a sweet taste, of a particular product for oral administration when administered as a combination.

Sweet-taste modulation activity may be detected by methods known in the art, e.g., in vitro methods, or in vivo by animal or human sensory testing. While not wishing to be bound to any particular theory, Myd is involved in sweet taste activation e.g., is an agonist of taste 1 receptor member 2 (T1R2) and/or taste 1 receptor member 3 (T1R3). However, Myd agonizes other taste receptors, such as bitter, umami, sour and salty. Such functional effects can be measured by any means known to those skilled in the art, e.g., measurement of binding to taste receptors T1Rs via changes in spectroscopic characteristics (e.g., fluorescence, absorbance, refractive index), hydrodynamic (e.g., shape), chromatographic, or solubility properties, patch clamping, voltage-sensitive dyes, whole cell currents, radioisotope efflux, inducible markers, transcriptional activation of T1R genes; ligand-binding assays; voltage, membrane potential and conductance changes; ion flux assays; changes in intracellular second messengers such as cAMP, cGMP, and inositol triphosphate (IP3); changes in intracellular calcium levels; neurotransmitter release, and the like.

Sensory testing (human or animal) may also be employed to determine whether a Myd candidate polypeptide has sweet-taste modulation activity. Sensory evaluation is a scientific discipline that analyses and measures human responses to the composition of food and drink, e.g. appearance, touch, odor, texture, temperature and taste. Measurements using people as the instruments are sometimes necessary. Selection of an appropriate method to determine sweetening can be determined by one of skill in the art, and includes, e.g., discrimination tests or difference tests, designed to measure the likelihood that two products are perceptibly different. Responses from the evaluators are tallied for correctness, and statistically analyzed to see if there are more correct than would be expected due to chance alone.

Sensory evaluation is a scientific discipline that analyses and measures human responses to the composition of food and drink, e.g. appearance, touch, odor, texture, temperature and taste. Measurements using people as the instruments are sometimes necessary. The food industry had the first need to develop this measurement tool as the sensory characteristics of flavor and texture were obvious attributes that cannot be measured easily by instruments. Selection of an appropriate method to determine the organoleptic qualities, e.g., sweetness of proteins disclosed in the instant invention can be determined by one of skill in the art, and includes, e.g., discrimination tests or difference tests, designed to measure the likelihood that two products are perceptibly different. For sweetness perception, for example, samples of, for example, one or more of 5% sucrose, 6% sucrose, 7% sucrose, 8% sucrose, 9% sucrose, 10% sucrose, and a test sample can be ranked by trained panelists in order of sweet taste intensity from low sweet to high sweet. In the instant invention, it should be understood that there are any number of ways one of skill in the art could measure the sensory differences.

Brix measurement (or Brix scale) is a well-known application in the food and beverage industry that determines pure sucrose content in water: 1 degree Brix (°Bx)=1 g of sucrose/100 g of solution and represents the strength of the solution as percentage by mass. 8°Bx is equivalent to approximately an 8% sugar solution. As described in the Examples, purified polypeptide corresponding to SEQ ID NO:21 was tasted at 0.03 mg/ml by a trained sensory scientist (0.2 mL aliquot) and found to have a sweetness equivalent to 8° Bx (approximately 8% sugar solution) (see Examples 4, 5, 9, and 10).

In some embodiments, the Myd polypeptides of the invention include polypeptides that are at least as sweet as sugar (on a w/w basis) (e.g., 1×), or alternatively, are 2×, 5×, 10×, 50×, 100×, 200×, 400×, 600×, 800×, 1000×, 1500×, 2000×, 3000×, 5000×, 10,000×, 20,000× or more sweeter than sugar, as measured by any of the methods described above or known in the art. In other embodiments, the Myd polypeptides are at least 1% (at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%) as sweet as sugar.

Foods, Beverages, Supplements, Medicinal Products

In one embodiment, the present invention includes a composition comprising, consisting essentially of, or consisting of a combination of a product for oral administration and a sweetening composition comprising an isolated Myd polypeptide according to the invention, as described herein. In one aspect, the combination has enhanced sweet taste compared to a product for oral administration lacking the Myd polypeptide (control). In one embodiment, the product for oral administration is not *Mattirolomyces terfezioides* truffle. The term "consisting essentially of" allows for the inclusion of components that are not essential to the function or activity of the product and do not materially affect the function or activity, such an anti-caking agent, filler, stabilizer (e.g., thermal stabilizer), and bulking agent (e.g., maltodextrose, gum acacia and the like).

In one embodiment, compositions comprising an isolated Myd protein of the invention may include a formulation that provides enhanced functionality to the isolated Myd protein. For example, a composition may include a formulation that stabilizes the Myd protein against thermal, osmotic, pH, or other types of degradation. In one embodiment, the formulation stabilizes the Myd protein against thermal degradation. Exemplary compounds for stabilizing the Myd protein includes, for example, L-arginine glycine, L-proline, L-histidine, β-alanine, L-serine, L-arginine ethyl ester dihydrochloride, L-argininamide dihydrochloride, 6-aminohexanoic acid, gly-gly, gly-gly-gly, tryptone, betaine monohydrate, D-(+)-trehalose dihydrate, xylitol, D-sorbitol, sucrose, hydroxyectoine, trimethylamine n-oxide dihydrate, methyl-α-d-glucopyranoside, triethylene glycol, spermine tetrahydrochloride, spermidine, 5-aminovaleric acid, glutaric acid, adipic acid, ethylenediamine dihydrochloride, guanidine hydrochloride, urea, N-methylurea, N-ethylurea, N-methylformamide, hypotaurine, TCEP hydrochloride, GSH (1-glutathione reduced), benzamidine hydrochloride, ethylenediaminetetraacetic acid disodium salt dihydrate, magnesium chloride hexahydrate, cadmium chloride hydrate, non detergent sulfobetaine 195 (ndsb-195), non detergent sulfobetaine 201 (NDSB-201), non detergent sulfobetaine 211 (NDSB-211), non detergent sulfobetaine 221 (NDSB-221), non detergent sulfobetaine 256 (NDSB-256), taurine, acetamide, oxalic acid dihydrate, sodium malonate pH 7.0, succinic acid pH 7.0, tacsimate pH 7.0, tetraethylammonium bromide, choline acetate, 1-ethyl-3-methylimidazolium acetate, 1-butyl-3-methylimidazolium chloride, ethylammonium nitrate, ammonium sulfate, ammonium chloride, magnesium sulfate hydrate, potassium thiocyanate, gadolinium (III) chloride hexahydrate, cesium chloride, 4-aminobutyric acid (GABA), lithium nitrate, DL-malic acid pH 7.0, lithium citrate tribasic tetrahydrate, ammonium acetate, sodium benzenesulfonate, sodium p-toluenesulfonate, sodium chloride, potassium chloride, sodium phosphate monobasic monohydrate, sodium sulfate decahydrate, lithium chloride, sodium bromide, glycerol, ethylene glycol, polyethylene glycol 200, polyethylene glycol monomethyl ether 550, polyethylene glycol monomethyl ether 750, formamide, polyethylene glycol 400, pentaerythritol ethoxylate (15/4 EO/OH), 1,2-propanediol, polyethylene glycol monomethyl ether 1,900, polyethylene glycol 3,350, polyethylene glycol 8,000, polyvinylpyrrolidone k15, polyethylene glycol 20,000, (2-hydroxypropyl)-β-cyclodextrin, α-cyclodextrin, β-cyclodextrin, methyl-β-cyclodextrin.

In one aspect, the Myd polypeptide of the sweeting composition can comprise an amino acid sequence having at least 80% sequence identity to SEQ ID NO:3 (or, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17). In another aspect, the Myd polypeptide has a polypeptide sequence having at least 80% sequence identity to a polypeptide sequence selected from the group consisting of SEQ ID NO:3, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, and SEQ ID NO:17; (a) wherein the polypeptide contains at least one substitution modification relative to the polypeptide sequence selected from the group consisting of SEQ ID NO:3, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, and SEQ ID NO:17, wherein the polypeptide is not the polypeptide of SEQ ID NO:3, or (b) wherein the polypeptide further comprises a histidine tag, wherein the polypeptide has sweet-taste modulation activity. For example, the polypeptide comprises the amino acid sequence of SEQ ID NO:71, SEQ ID NO:72, SEQ ID NO:73, SEQ ID NO:74, or SEQ ID NO:75 and does not consist of SEQ ID NO:3. In a particular aspect, the polypeptide comprises the amino acid sequence of SEQ ID NO:24, SEQ ID NO:26, SEQ ID NO:30, SEQ ID NO:38, SEQ ID NO:42, SEQ ID NO:44, SEQ ID NO:46, SEQ ID NO:50, SEQ ID NO:52, SEQ ID NO:54, SEQ ID NO:58, SEQ ID NO:60, SEQ ID NO:62, SEQ ID NO:64, SEQ ID NO:66, or SEQ ID NO:68.

The present invention also includes a method for modulating the taste of a product for oral administration, comprising combining the product for oral administration with an effective amount of an isolated Myd polypeptide, as described herein. In one aspect, the combination has enhanced sweet taste compared to a product for oral administration lacking the Myd polypeptide (control). In one embodiment, the product for oral administration is not *Mattirolomyces terfezioides* truffle.

In one aspect, the Myd polypeptide of the sweeting composition can comprise an amino acid sequence having at least 80% sequence identity to SEQ ID NO:3 (or, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17). In another aspect, the Myd polypeptide has a polypeptide sequence having at least 80% sequence identity to a polypeptide sequence selected from the group consisting of SEQ ID NO:3, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, and SEQ ID NO:17; (a) wherein the polypeptide contains at least one substitution modification relative to the polypeptide sequence selected from the group consisting of SEQ ID NO:3, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, and SEQ ID NO:17, wherein the polypeptide is not the polypeptide of SEQ ID NO:3, or (b) wherein the polypeptide further comprises a histidine tag, wherein the polypeptide has sweet-taste modulation activity.

The product for oral administration may be a food, a beverage, a dietary supplement composition, or a pharmaceutical composition.

The term "product for oral administration" may refer to a comestible product such as a food product, a beverage product; a medicinal (pharmaceutical) product, or a dietary supplement product such as an herbal supplement. As used herein, the term "medicinal product" includes both solids and liquid compositions which are ingestible non-toxic materials which have medicinal value or comprise medicinally active agents such as cough syrups, cough drops, aspirin and chewable medicinal tablets. An oral hygiene product is also a product for oral administration and includes solids and liquids such as toothpaste or mouthwash.

In general terms, the present invention contemplates that food or beverage products may include an isolated sweet protein of the invention in an effective amount, e.g., in an amount of up to about 99% by weight relative to the total weight of the food or beverage product, for example in an amount from about 0.01% by weight to about 99% by weight. All intermediate weights (i.e., 0.01%, 0.05%, 0.1%, 0.5%, 1%, 2%, 3%, 4%, . . . 90%, 95%, 99%) by weight relative to the total weight of the food or beverage products are contemplated, as are all intermediate ranges based on these amounts.

The compositions of the invention may include a "comestibly, biologically or medicinally acceptable carrier or excipient" which can include a solid or liquid medium and/or composition that is used to prepare a desired dosage form of a Myd polypeptide, in order to administer a Myd polypeptide in a dispersed/diluted form, so that the biological effectiveness of a Myd polypeptide is maximized. A comestibly, biologically or medicinally acceptable carrier includes many common food ingredients, such as water at neutral, acidic, or basic pH, fruit or vegetable juices, vinegar, marinades, beer, wine, natural water/fat emulsions such as milk or condensed milk, edible oils and shortenings, fatty acids, low molecular weight oligomers of propylene glycol, glyceryl esters of fatty acids, and dispersions or emulsions of such hydrophobic substances in aqueous media, salts such as sodium chloride, wheat flours, solvents such as ethanol, solid edible diluents such as vegetable powders or flours, or other liquid vehicles, dispersion or suspension aids, surface active agents, isotonic agents; thickening or emulsifying agents, preservatives, solid binders, lubricants and the like.

Food or beverage products that may be contemplated in the context of the present invention include baked goods; sweet bakery products, (including, but not limited to, rolls, cakes, pies, pastries, and cookies); pre-made sweet bakery mixes for preparing sweet bakery products; pie fillings and other sweet fillings (including, but not limited to, fruit pie fillings and nut pie fillings such as pecan pie filling, as well as fillings for cookies, cakes, pastries, confectionary products and the like, such as fat-based cream fillings); desserts, gelatins and puddings; frozen desserts (including, but not limited to, frozen dairy desserts such as ice cream—including regular ice cream, soft serve ice cream and all other types of ice cream—and frozen non-dairy desserts such as non-dairy ice cream, sorbet and the like); carbonated beverages (including, but not limited to, soft carbonated beverages); non-carbonated beverages (including, but not limited to, soft non-carbonated beverages such as flavored waters and sweet tea or coffee based beverages); beverage concentrates (including, but not limited to, liquid concentrates and syrups as well as non-liquid concentrates, such as freeze-dried and/or powder preparations); yogurts (including, but not limited to, full fat, reduced fat and fat-free dairy yogurts, as well non-dairy and lactose-free yogurts and frozen equivalents of all of these); snack bars (including, but not limited to, cereal, nut, seed and/or fruit bars); bread products (including, but not limited to, leavened and unleavened breads, yeasted and un-yeasted breads such as soda breads, breads comprising any type of wheat flour, breads comprising any type of non-wheat flour (such as potato, rice and rye flours), gluten-free breads); pre-made bread mixes for preparing bread products; sauces, syrups and dressings; sweet spreads (including, but not limited to, jellies, jams, butters, nut spreads and other spreadable preserves, conserves and the like); confectionary products (including, but not limited to, jelly candies, soft candies, hard candies, chocolates and gums); sweetened breakfast cereals (including, but not limited to, extruded (kix type) breakfast cereals, flaked breakfast cereals and puffed breakfast cereals); and cereal coating compositions for use in preparing sweetened breakfast cereals. Other types of food and beverage product not mentioned here but which conventionally include one or more nutritive sweetener may also be contemplated in the context of the present invention.

As a consequence of the complete or partial replacement of nutritive sweeteners in the food or beverage products of the present invention, the food or beverage products of the present invention may be useful as low calorie or dietetic products, medical foods/products (including pills and tablets), and sports nutrition products, and may be particularly suitable for food or beverage products requiring a lower sweetness at a given soluble solids level.

In some embodiments, the sweetening composition of the invention can be supplemented with other nutritional or non-nutritional sweeteners to form a sweetener system. The sweetener system may comprise the sweetening composition of the invention, a bulking agent such as maltodextrose, gum acacia and the like, and at least one high intensity sweetener. The composition may be provided as liquid composition or a dried blend.

In an embodiment, the present invention includes a process for enhancing the sweet taste of a product for oral administration, comprising the addition of a Myd polypeptide of the invention.

In another embodiment, the methods of the invention include a method for improving the sweet flavor of a product for oral administration, comprising adding to the product for oral administration a sweetening composition made by the methods of the invention. Amounts to add can be determined by methods known in the art, e.g., using sensory testing as a guide.

The following examples further illustrate the invention but, of course, should not be construed as in any way limiting its scope.

EXAMPLES

Example 1

Fresh *Mattirolomyces terfezioides* truffles were obtained in situ using appropriate procedures and permissions in their natural range. Fresh samples (29 in total) were shipped to MycoTechnology, Inc. facilities and were gently washed in RO water, then frozen in liquid nitrogen and stored at −80° C. The average moisture content of the truffles was 83.6% plus or minus 4.6%.

Aqueous extraction of the truffles was performed as follows. Eight different samples of truffle were pestled in liquid nitrogen to grind into a powder, then 5:1 v/w truffle of 4° C. water was added and allowed to incubate at 30 minutes at 4° C. The extracted material was then subjected to low-speed brief centrifugation and the filtrate was tasted "neat." The sweetness intensity was rated between 0 for no sweetness and 10 for extremely sweet. Of the samples, the sweetness was rated as follows:

TABLE 1

Sweetness of various truffle samples.

| sample | Sweetness intensity | Notes |
|---|---|---|
| 1 | 5 | Sweet taste at end |
| 2 | 8 | Sweet taste is upfront and intensifies at mid-end and lingers |
| 3 | 7 | Sweetness is upfront and intensifies at mid-end and lingers. |
| 4 | 5 | Sweet upfront, low sweet linger |
| 5 | 4 | Sweetness less strong |
| 6 | 3 | Low sweetness |
| 7 | 6 | A mild and clean sweet taste |

Aqueous extract was stored at 4° C. at pH 7 and pH 2 in sodium phosphate buffer, and little to no change in sweetness was observed over an 8-day period.

Example 2

Figure 2:
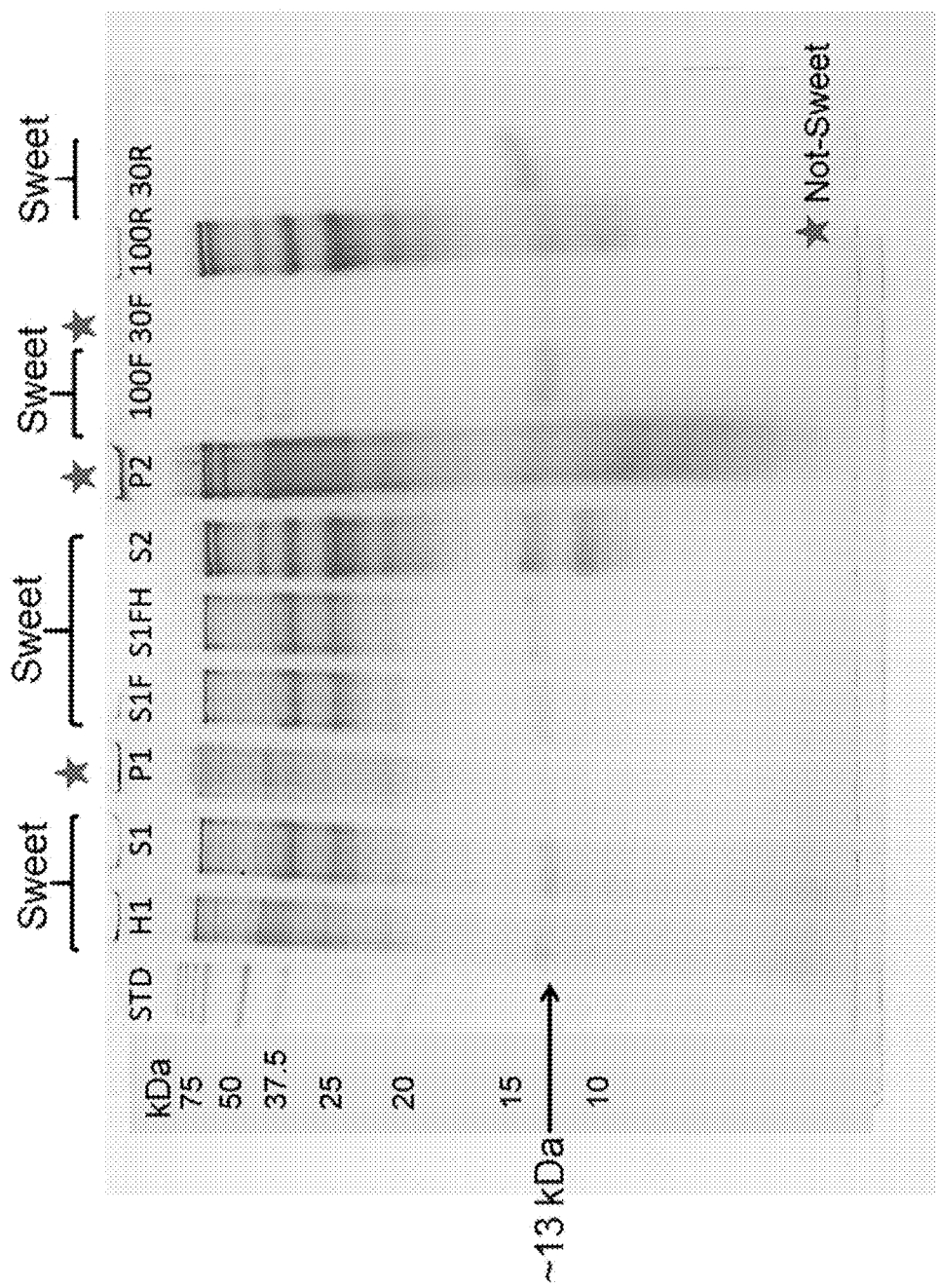
FIG. 2 shows a Coomassie-stained SDS-PAGE gel of proteins obtained from fractions of partially purified *M. terfezioides* gleba.

Purification of sweet protein Myd from *M. terfezioides*. Fresh *Mattirolomyces terfezioides* truffles were obtained in situ using appropriate procedures and permissions in their natural range and stored at −80° C. 16.3 g sample was removed from the freezer, and was ground with a mortar and pestle (white ceramic) in liquid nitrogen. Grinding proceeded for 15 minutes to fully pulverize tissue and obtain a fine frozen powder. Powder was added to 50 mL Falcon tubes and 20 mL RO—H₂O was added, and vortexed to mix tissue, until no ice crystals were observed. A Rotor-Stator at a setting of 20 for 2×1 minutes at 4° C. was used to breakup fragment and make a homogenous solution (H1). The volume of slurry was adjusted to 53 mL with RO—H₂O and centrifuged at 7500×G for 30 minutes at 4° C. The supernatant (S1) from this step was collected into 2 mL Eppendorf tubes and centrifuged in a 5417 R and Eppendorf centrifuge at 20,000×G for 15 minutes at 4° C. The pellet (P1) was discarded. The sweet taste (via human sensory) was perceived in the supernatant. Supernatant from this step was collected and pooled. The supernatant was then filtered through a 0.45 micron syringe filter (Cellulose, VWR International), 25 mm, and called S1+0.22 um Filtration. The filtrate was then washed with hexane (38 mL to 50 mL hexane 2 times, and the water phase was collected. S1FH is S1F+hexane wash. The hexane phase was saved and dried. The water phase was then precipitated with acetone (50 mL at −20° C. was added to 33 ml of fraction S1FH and set for 30 minutes at −20° C.). The sample was centrifuged at 3,000×g and the precipitate was collected. The precipitate was resuspended in 10 mM sodium phosphate pH 6, with the supernatant from this step called S2, and the precipitate called P2. The supernatant S2 was first applied to an AMICON centrifugal filter units with a molecular weight cutoff of 100 kD, obtaining a filtrate (flow-through) portion (called 100F) and a retentate (called 100R); followed by applying the 100F to a unit with a molecular weight cutoff of 30 kD, resulting in a filtrate (30F) and a retentate (30R). The sweet taste fraction flowed through the 100 kD column and appeared in 100F, and was retained on the 30 kD column (30R). A band was observed at approximately 13 kDa on the SDS-PAGE of FIG. 2, shown by the arrow, and this band was cut out and subjected to N-terminal sequence analysis by Edman degradation using standard methods of detection e.g. liquid chromatography and mass spectrometry to identify the residues for each cycle. A polypeptide was detected, SEQ ID NO:4.

Example 3 (Identification of RNA)

Sample Collection

Fresh *Mattirolomyces terfezioides* truffles were obtained in situ using appropriate procedures and permissions in their natural range. A wild isolate (BDP2_18) of *Mattirolomyces terfezioides* truffle (gleba) was sourced from a natural environment. BDP2_18 was the largest wild truffle scavenged and the truffle had a sweetness characteristic of "sweet upfront, more fungal and earthy, low sweet linger."

Sample Identification

The wild isolates of gleba were shipped frozen to GeneWiz for Internal Transcribed Spacer (ITS) Sequencing. The genome loci sequenced are the ITS 1 & 2 region. The resulting sanger sequencing reads were then aligned and trimmed of low-quality bases. Each sequence was then subjected to an individual Basic Local Alignment Search Tool (BLAST) (Altschul, Gish, Miller, Myers, & Lipman, 1990) search to verify identity. BLASTn search was employed using nucleotide collection (nr/nt) with unpublished samples sequences excluded. The entry with the highest percent identity to the wild isolate is *Mattirolomyces terfezioides* strain rib02.

Sample Preparation

The wild isolate, BPD2_18, was superficially washed with sterile water and cut into cubes weighing ~100 mg and flash frozen in liquid N2 to be stored at −80° C. Shipment was carried out on dry ice for GeneWiz.

RNA Sequencing

The following samples were submitted through GeneWiz for Standard RNASeq going through Illumina HiSeq, 2×150 bp, single index, per lane with ~350M raw paired-end reads per lane. This RNASeq study involved polyA+ selection for transcriptome profiling.

GeneWiz extracted RNA using the Qiagen RNeasy Plus Universal mini kit following manufacturer's instructions. RNA Library prep was done using the NEBNext Ultra RNA Library Prep Kit for Illumina. The Illumina adapter sequences are outlined below.

```
                                             (SEQ ID NO: 18)
5'-AATGATACGGCGACCACCGAGATCTACACTCTTTCCCTACAC

GACGCTCTTCCGATCT -3'
```

```
                                             (SEQ ID NO: 19)
5'- GATCGGAAGAGCACACGTCTGAACTCCAGTCAC[i7barcode]

ATCTCGTATGCCGTCTTCTGCTTG -3'
```

Fastq sequence files from the RNA-seq study on two strains of *Mattirolomyces terfezioides* (three replicates each) were trimmed and cleaned with HTStream to remove the following contaminants: PhiX (common contaminant from sequencing), rRNA reads, sequencing adapters, low quality and "N" bases, poly-a tracts, primers and reads <50 bp. rnaSPAdes (Bushmanova E, Antipov D, Lapidus A, Prjibelski A D. rnaSPAdes: a de novo transcriptome assembler and its application to RNA-Seq data. Gigascience. 2019; 8(9): giz100. doi:10.1093/gigascience/giz100) was then used for the de novo assembly of the transcriptome for each strain of *M. terfezioides* from the cleaned files. Bandage (a Bioinformatics Application for Navigating De novo Assembly Graphs Easily) (Ryan R. Wick, Mark B. Schultz, Justin Zobel, Kathryn E. Holt, Bandage: interactive visualization of de novo genome assemblies, Bioinformatics, Volume 31, Issue 20, 15 Oct. 2015, Pages 3350-3352) was used to visualize and search the assembly for the target peptide using a tBLASTn search (Gertz E M, Yu Y K, Agarwala R, Schiffer AA, Altschul S F. Composition-based statistics and translated nucleotide searches: improving the TBLASTN module of BLAST. BMC Biol. 2006; 4:41. Published 2006 Dec. 7. doi:10.1186/1741-7007-4-41) that compares the protein query sequence (PDLSSFITIKNNSNHVFTRT, SEQ ID NO:4) against the assembled transcriptome sequence database dynamically translated in all six reading frames. Contigs that contained perfect matches to the query protein sequence were analyzed for open reading frames (ORFs) and eventually used to construct the full-length mRNA connected to the target peptide.

An RNA transcript was identified, and the DNA copy thereof has the sequence shown as SEQ ID NO:1, of which SEQ ID NO:2 is the predicted coding sequence based on the start and stop codons. A predicted protein, SEQ ID NO:3, is also provided, having 121 amino acids with an estimated size of 13.3 kD. Length: 122 aa, molecular weight: 13.381 kDa, predicted isoelectric point: 8.64, and predicted charge at pH 7: 1.01.

Blast analyses. Identity between the predicted protein SEQ ID NO:3, and other protein sequences in GENBANK were 31% or less. A hypothetical protein from *Pisolithus tincturius* was found (GenBank: KIN98154.1; SEQ ID NO:7) with approximately 31% homology to SEQ ID NO:3; called hypothetical protein M404DRAFT 1005519 [*Piso-*

*lithus tinctorius* Marx 270]. It is hypothesized that SEQ ID NO:7 may also have sweet modulating activity. The complete cDNA copy of the RNA transcript is SEQ ID NO:5 with the coding sequence given as SEQ ID NO:6.

Example 4 (Cloning and Heterologous Expression of Mycodulcein in *E. coli*; Confirmation of Sweet Taste)

Based on the nucleotide sequence identified as SEQ ID NO:3, three expression vectors to express SEQ ID NO:20 containing a histidine tag were synthesized and cloned by Atum, Inc. (Newark, Calif.) into three different Atum vector backbones: pD454-SR (plasmid pMy_3000), pD454-MR (plasmid pMy_3001), and pD454-WR (plasmid pMy_3002), all of which are *E. coli* IPTG-inducible T7 promoter expression vectors with ampicillin-r, lacI, Lac01, Ori_pUC, and medium (M), strong (S) and weak (W) ribosome binding sites on the plasmid. *E. coli* BL21 DE3 (Studier et al. (1986) J. Mol. Biol. 189:113-130) (New England Biolabs) was transformed with pMy_3000, pMy_3001, pMy_3002 using manufacturer protocols. In short, previously frozen competent cells were thawed and mixed with 1 pg-100 ng of plasmid DNA and held on ice for 30 minutes. A heat shock of 42° C. for 45 seconds was applied to this mixture. Immediately thereafter, the mixture was placed into an ice bath lasting for 10 minutes. 950 μL of pre-warmed LB media was added and then subjected to 1 hr of 225 rpm shaking at 37° C. Dilution of cells at 1:10 and 1:100 and plating 100 μL on the antibiotic plate was performed for each transformation reaction. An overnight growth at 37° C. allowed colonies to fully recover and become visible. To confirm successful transformation, csPCR (colony screen PCR) was performed to interrogate the cDNA region of the plasmid and expression was confirmed through lysate SDS-PAGE. Shake flask-scale induced expression was used to confirm heterologous expression in the *E. coli* host. This process yielded strains Z14CE, Z15CE, Z16CE containing the plasmids pMy_3000, pMy_3001, and pMy_3002 respectively. The three strains (Z14CE, Z15CE, Z16CE) were maintained on LB+ampicillin 100 ng/mL agar plates while the negative control (Eco_0001) was maintained on a LB agar plate. An overnight culture of was grown for each strain in 50 mL of LB liquid media in un-baffled 250 mL culture shake flask at 37° C. shaking 150 rpm overnight with appropriate antibiotics. Each overnight culture was subsequently seeded into 200 mL of TB liquid media the following day into baffled 1000 mL culture shake flask at 37° C. shaking at 200 rpm and adjusted to 0.1 OD600 with the appropriate antibiotic. Once the OD600 reached 0.8, supplement of IPTG was added into the media to a final concentration of 0.66 mM. Continued the shaking at 37° C. for an additional 5 hrs. After expression, the cells were centrifuged at 4000 g for 20 min. The supernatant was discarded, and pellet was suspended in ~20 mL of wash buffer (10 mM Sodium Phosphate Buffer pH 7.0). Suspended cells were disrupted in a high-pressure homogenizer (C3 Emulsiflex, Avestin, Inc., Ottawa, ON, Canada) operated at a max of 2,000 bar. Disrupted cells were centrifuged at 13,000 g (30 min), the supernatant was collected, and the pellet was discarded. The supernatant containing solubilized protein was filtered through a 0.22 μm PES membrane unit (Millipore, Burlington, Mass., USA). SDS PAGE was run and a 13.1 kD band (Coomassie stain) was observed to confirm expression.

Figure 3:
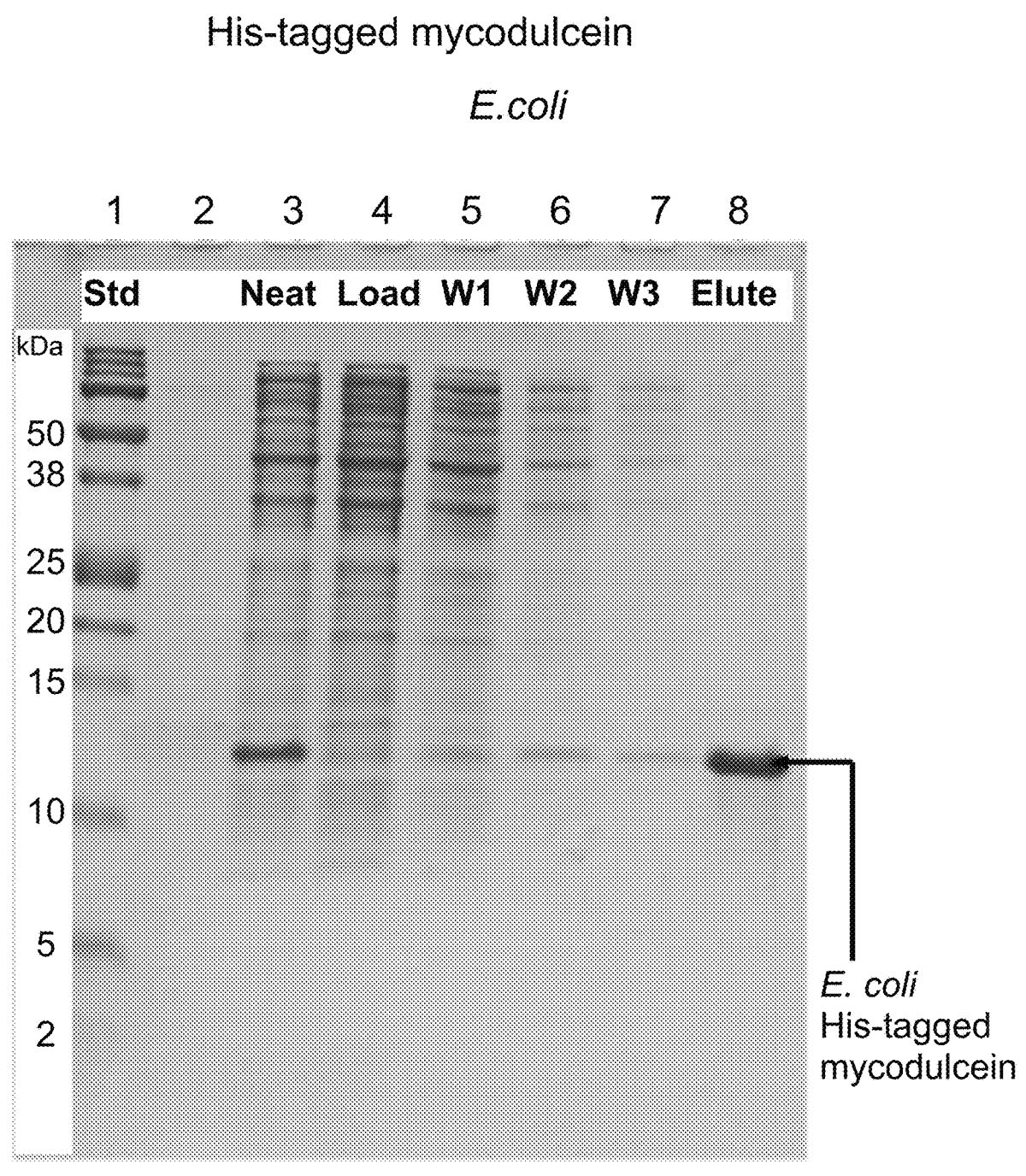

Thermo Scientific™ HisPur™ Ni-NTA resin was used to purify the his-tagged protein SEQ ID NO:20 using effective immobilized metal affinity chromatography (IMAC). SEQ ID NO:20 was purified using nickel-charged nitrilotriacetic acid (NTA) chelate immobilized onto 6% crosslinked agarose resin. Lysate was loaded onto prepared IMAC column, equilibrating to Binding Buffer: 20 mM sodium phosphate monobasic, 0.5M sodium chloride, 0.1M imidazole, pH 7.4, and eluted using Elution Buffer: 20 mM sodium phosphate monobasic, 0.5M sodium chloride, 0.5M imidazole. The column was washed three times with Binding Buffer followed by eluting his-tagged mycodulcein four times with elution buffer, followed by ultrafiltration of eluted fractions using a 30 kDa MWCO filter followed by filtering filtrate through 10 kD filters for 4000×G for 15 minutes. The retentate was diluted and spun again for a wash step, repeated three times. Purification steps analysis by SDS-PAGE is shown in FIG. 3.

The purified fraction (shown in Lane 8 from FIG. 3, containing highly purified SEQ ID NO:21) was tasted at 0.03 mg/ml by a trained sensory scientist (0.2 mL aliquot) and found to have a sweetness equivalent to 8° brix (approximately 8% sugar solution), confirming that mycodulcein isolated from *M. terfezioides* was responsible for the sweet taste activity observed in Examples 1 and 2. The sweet taste was very noticeably sweet, with a "clean" sweetness (sugar-like taste) with no other flavors, with a slightly delayed onset and a sweet aftertaste.

Example 5 (Pilot-Scale Production of Mycodulcein (His-Tag))

*E. coli* strain Z14CE prepared in Example 4 containing coding sequence SEQ ID NO:20 was tested for its performance during fermentation in a lab-scale bioreactor. Bioreactor cultures were performed in 10.0 L Bioflo 320 round bottomed stirred fermentor (BioFlo/CelliGen 310, New Brunswick Scientific, Edison, N.J., USA). The fermenter was fitted with pH and dissolved oxygen sensors (Mettler Toledo, Ohio, USA). Temperature was controlled via a water-filled stainless-steel base. Agitation was provided by two mounted six-bladed Rushton turbines spaced 47 mm apart with the lowermost impeller positioned just above the bottom of the shaft. Aeration occurred through a perforated pipe sparger ring. Dissolved oxygen (DO) was controlled at 20% of air saturation by using a sequential cascade of agitation between 500 and 800 rpm and aeration between 5 and 8 L/min with air sparged at high-cell densities. The pH was controlled at 7.0 using 5.0 M ammonium hydroxide. Antifoam 204 (Sigma, St Louis, Mo., USA) was added automatically to control the foaming. The latter was sensed using a conductivity probe mounted 10 cm above the culture level. The main fermentation medium contained (per liter) 24 g yeast extract, 12 g tryptone, 5.42 mL glycerol, 100 mL of phosphate buffer stock (0.17 M $KH_2PO_4$, 0.72 M $K_2HPO_4$) The medium was adjusted to pH 7.0 using 2 M HCl. When the original glucose supply was depleted (signaled by a rise in pH), a feed medium (per liter) consisting of 200 g glucose, 21.1 g $(NH_4)_2SO_4$ and 19.7 g $MgSO_4$ was pumped into the fermenter at an initial flow rate of 1.00 mL/min. Unless otherwise stated, the initial volume of the medium in the vessel was 4.0 L. Inoculum (200 ml) consisted of a culture that had been grown for 16 h in a 1 L baffled shake flask (37° C., 200 rpm) in LB started culture media. The fermenter temperature was 37° C. Fermentations were induced with 0.66 mM IPTG after optical density reached 10-20 and continued for thereafter for 24 hours. The broth was subsequently centrifuged at 4000 g for 20 min after the 24-hour induction period. The supernatant was discarded, and pellet was suspended in 1 L of wash buffer (10 mM sodium phosphate buffer pH 7.0). Suspended cells were disrupted in a high-pressure homogenizer (C3 Emulsiflex, Avestin, Inc., Ottawa, ON, Canada) operated up to a max of 1,500 bar. Disrupted cells were centrifuged at 13,000 g (30 min), the supernatant was collected, and the pellet was discarded. The supernatant containing solubilized protein was filtered through a 0.22 μm PES membrane unit (Millipore, Burlington, Mass., USA).

The purified supernatant prepared in this Example was tasted at 0.03 mg/ml by a trained sensory scientist (0.2 mL aliquot) and found to have a sweetness equivalent to 8° brix (approximately 8% sugar solution). The sweet taste was very noticeably sweet, with a "clean" sweetness (sugar-like taste) with no other flavors, with a slightly delayed onset and a sweet aftertaste.

Supernatant was stored in aliquots at −20° C. and used for further experiments.

Example 6 (Mycodulcein from *E. coli* ELISA Quantification)

A direct ELISA was developed to quantify his-tagged mycodulcein (SEQ ID NO:21) with a horseradish peroxidase (HRP) conjugated antibody to the 6×His-Tag sequence on the carboxy terminus of SEQ ID NO:21. The ELISA enables the measurement of mycodulcein concentration in complex lysates and purified protein. Recombinant 6×His-tagged *E. coli* mycodulcein has a molecular weight of 14.2 kDa and a molar extinction coefficient of 27,960 $M^{-1}$ $cm^{-1}$, calculated from the amino acid sequence by methods known in the art. Purity was assessed by SDS-PAGE as >98%. Mycodulcein protein concentration was determined by absorbance at 280 nm using Beer-Lambert's Law, then a standard curve was generated using known concentrations of mycodulcein (μg/ml) for the ELISA.

ELISA procedure: Protein was bound to the walls of a high-protein binding 96-well plate in 50 mM carbonate buffer pH 9.4 coating buffer for 30 minutes at room temperature. The plates were washed 3 times with phosphate buffered saline (PBS) pH 7.4 with 0.02% Tween-20. Non-specific binding sites on the microplate were blocked with 5% BSA in PBS pH 7.4 for 15 minutes at room temperature and washed three times with PBS 0.02% Tween-20. The primary antibody was diluted (1:1000) in blocking buffer and the microplates were incubated for 1 hour and washed 3 times in PBS 0.02% Tween-20. The colorimetric substrate, 3,3',5,5'-tetramethylbenzidine (TMB), was used to develop the HRP reaction for 8 minutes and stopped with 2N sulfuric Acid.

Example 7 (Quantitative Characterization of the Concentration-Dependence of Mycodulcein)

Figure 4:
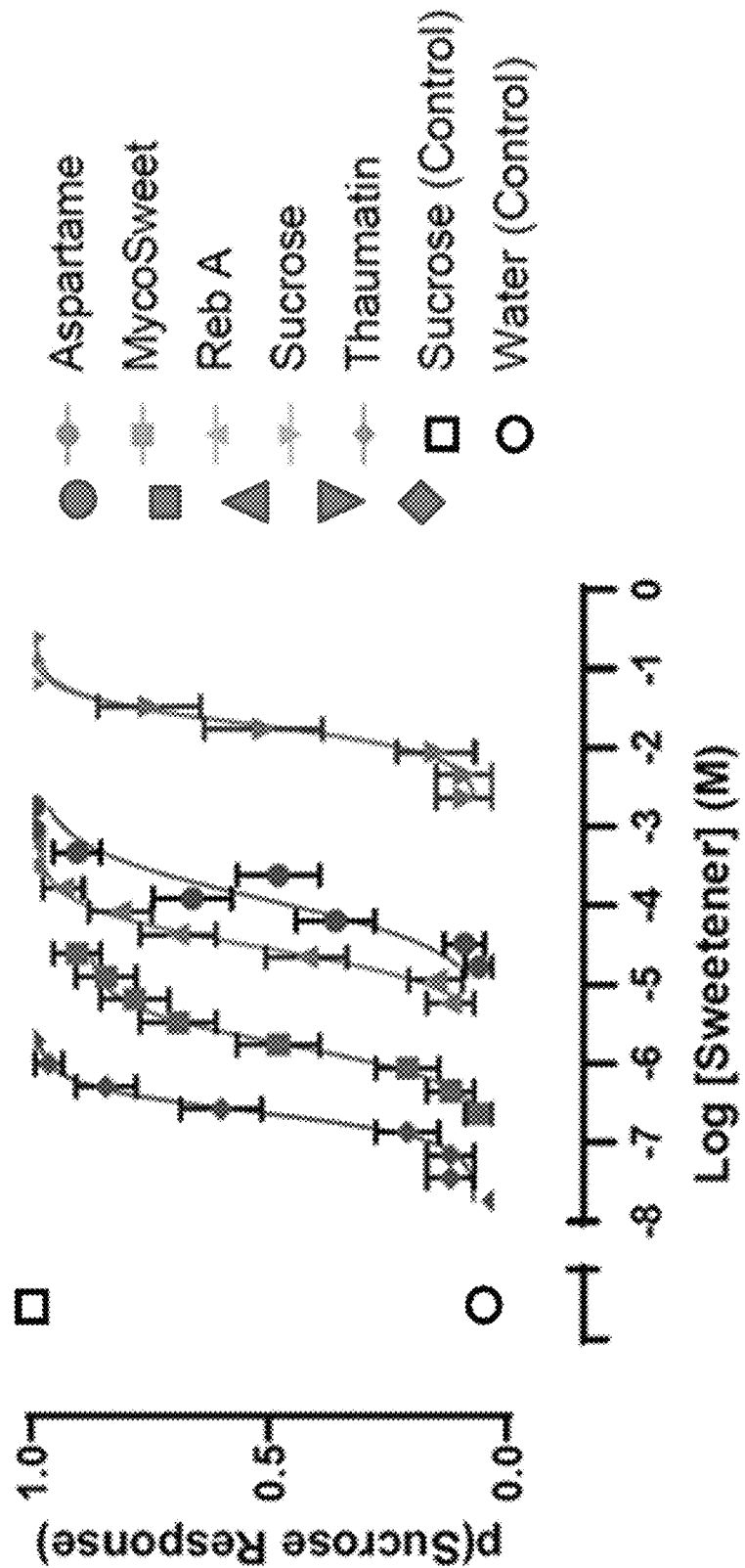
FIG. 4 shows the concentration-response functions for sweet taste for mycodulcein, aspartame, thaumatin, rebaudioside A. Data are plotted as the proportion (p) of responses occurring on the 200 mM sucrose-associated ("sweet") target. Each data point in the curves for mycodulcein, aspartame, thaumatin, rebaudioside A was calculated as the average across 32 replicates and averaged across 16 replicates for the sucrose curve; error bars are SEM. Points for water and sucrose controls were similarly calculated as the average across 128 and 64 replicates, respectively. Curves were fit by non-linear regression.

Opertech Bio (Philadelphia, Pa.) performed a quantitative characterization of the concentration-dependence of the taste properties of the purified his-tagged mycodulcein (SEQ ID NO:21) obtained from *E. coli* as described in Example 5 and purified as described in Example 4. The sweet-taste potency and relative efficacy of mycodulcein was compared with sucrose and with other sweeteners thaumatin, rebaudioside A, and aspartame. Control standards were solutions of 200 mM sucrose, 100 mM NaCl, 0.5 mM quinine, and 10 mM citric acid. FIG. 4 shows the concentration-response functions for sweet taste for mycodulcein, aspartame, thaumatin, rebaudioside A. Data are plotted as the proportion (p) of responses occurring on the 200 mM sucrose-associated ("sweet") target. Each data point in the curves for mycodulcein, aspartame, thaumatin, rebaudioside A was calculated as the average across 32 replicates and averaged across 16 replicates for the sucrose curve; error bars are SEM. Points for water and sucrose controls were similarly calculated as the average across 128 and 64 replicates, respectively. Curves were fit by non-linear regression.

The concentrations that elicit half-maximal sweet taste response (EC50s, or potencies) were derived from the non-linear regression. The EC50s (and 95% confidence intervals) for mycodulcein (MYC), sucrose (SUC), aspartame (ASP), rebaudioside A (REB), and thaumatin (THN) are given in Table 2. Also provided are the equivalencies to sucrose on a molar basis and on a weight basis.

TABLE 2

|  | EC50 (molar units) | CI 95% | EC50 (mg/ml) | Relative to Sucrose (mM) | Relative to Sucrose (mg/ml) |
|---|---|---|---|---|---|
| MYC | 2 μM | 2-3 μM | 0.0286 | 18000 | 431 |
| THN | 0.3 μM | 0.2-0.3 μM | 0.0066 | 120000 | 1865 |
| REB | 42 μM | 33-57 μM | 0.0411 | 857 | 300 |
| ASP | 182 μM | 142-254 μM | 0.0532 | 198 | 231 |
| SUC | 36 mM | 27-45 mM | 12.3120 | 1 | 1 |

Evaluation of thaumatin, sucrose, and SEQ ID NO:21 was carried out using a CATA (click all that apply) time intensity of the sweet sensation of named analytes in water at 0.045 mg/ml for proteins and 10% sucrose. Methodology: Time Intensity Technique; Data collection software: EyeQuestion, responses recorded every 2.57 seconds; Scaling Method: a 15-point sweet scale, e.g. score 5=5% sucrose, score 10=10% sucrose; Evaluation Protocol: small volume sip, tilt and spit test. There were 3-6 panelists and 2 replicates. All samples were blinded and presented with randomized 3-digit codes.

Training Strategies: An intense training on sweet scale over 6 weeks on 15-point sweet scale to confidently assign sweet values. Due to unique sweet behavioral patterns, it is necessary to train time intensity principles over 3 weeks. Samples were tasted with a stopwatch to note times and help reach a consensus. # of Panelists: 3-6, # of replications: 2. All samples were blinded and presented with randomized 3-digit codes. Statistical analysis: due to the small # of panelists, a statistical analysis cannot be performed.

The maximum intensity (Imax) of mycodulcein and thaumatin shows approximately 1 point higher on the 15 point scale at the amounts tested than sucrose. Thaumatin and mycodulcein have a flatter slope, indicating a longer peak time and more gradual/longer decline. Sucrose approaches threshold sweetness (Intensity <1) at 162 seconds, sooner than thaumatin and mycodulcein. When sucrose reaches threshold level, thaumatin and mycodulcein are recognizable at a low-moderate intensity. Mycodulcein and thaumatin appeared to be of similar potency in this experiment, which is on the order of 3000× sweeter than sucrose on a weight basis, or approximately 120,000× sweeter than sucrose on a molar basis. From these two experiments, mycodulcein is shown to be a high intensity sweet protein with a potency of between 400× sweeter than sucrose and 3000× sweeter than sucrose on a weight basis.

Example 8 (Production and Testing of Variants of Mycodulcein for Sweetness and Thermal Stability)

Figure 5A:
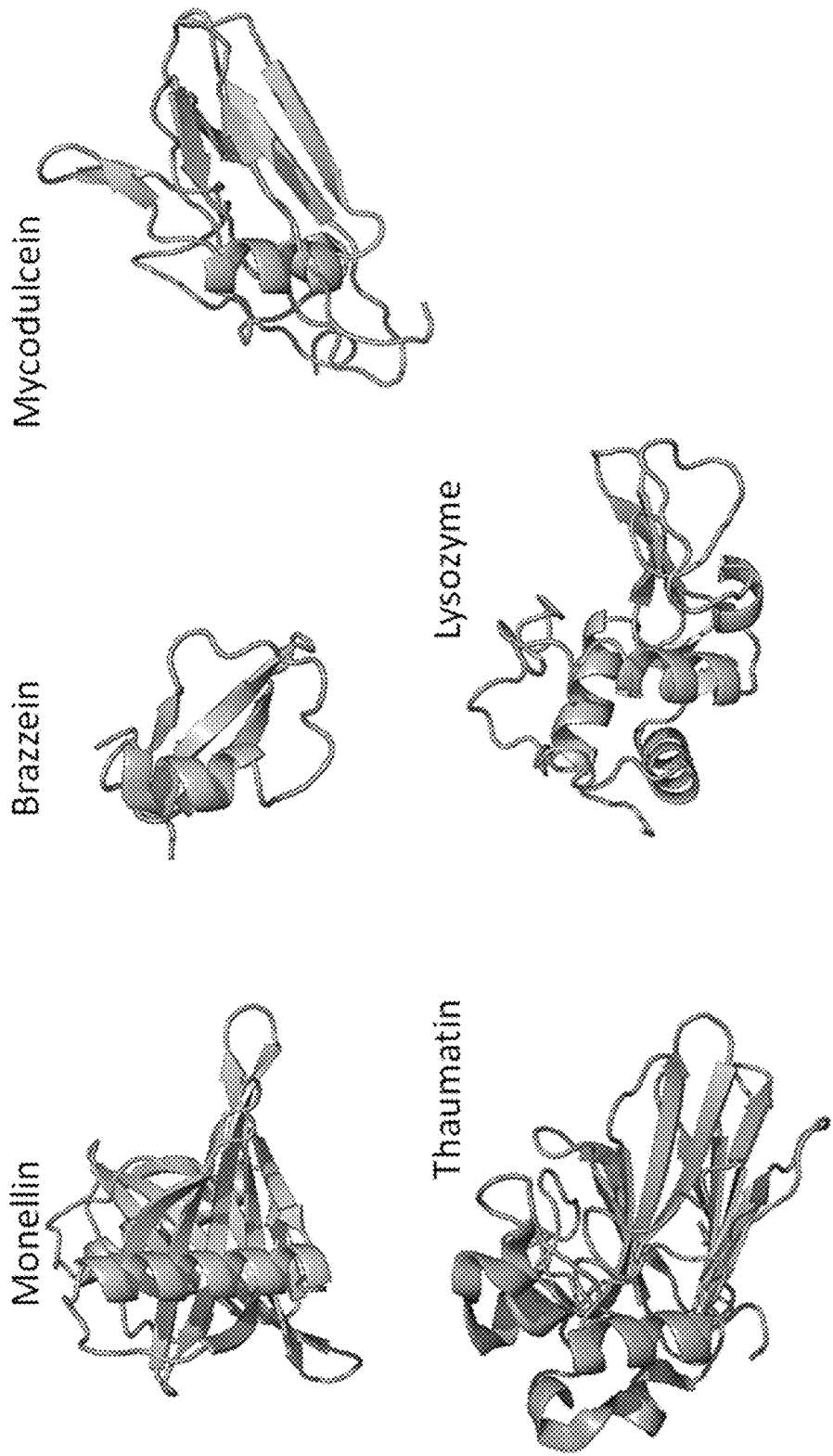
FIG. 5A shows a comparison of mycodulcein predicted tertiary structure to the known crystal structures of thaumatin (PDB: 1RQW), monellin (PDB: 2O9U), brazzein (PDB: 1BRZ), and chicken egg white lysozyme (PDB: 1LSN) (protein data base), showing that mycodulcein has predicted tertiary structure similarity to other known sweet proteins, all containing antiparallel beta-sheets with an alpha-helix parallel to the beta sheets.
Figure 5B:
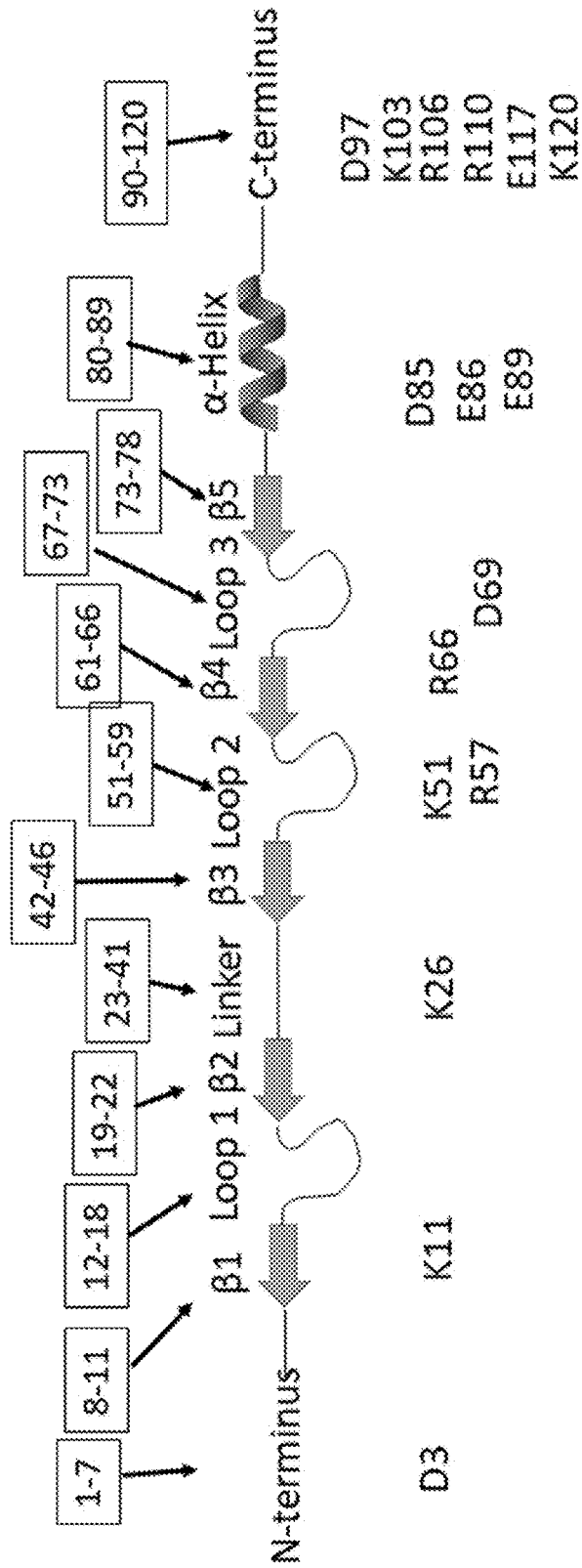
FIG. 5B shows a representation of SEQ ID NO:3 predicted secondary structure superimposed on putative secondary structure motifs and location of point mutations within each motif.
Figure 6:
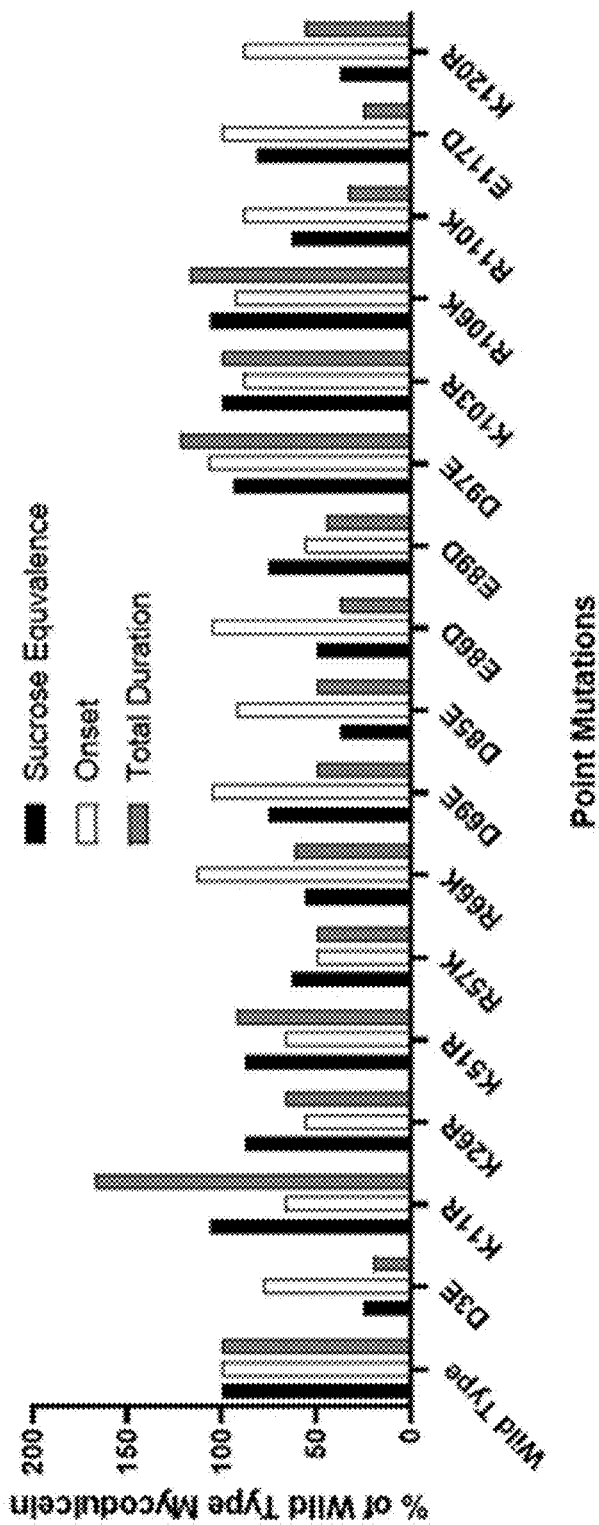
FIG. 6 shows results of mutant his-tagged mycodulcein compared with each other and with his-tagged non-mutant mycodulcein, equalized to equal protein concentration as measured by ELISA, for sweetness intensity, time of onset of sweetness perception, and for duration of sweetness perception.

Method to identify potential key residues in mycodulcein. Although sweet proteins have no primary sequence identity, the overall tertiary structures have a sweet finger motif (Tancredi, T., Pastore, A., Salvadori, S., Esposito, V. & Temussi, P. A. Interaction of sweet proteins with their receptor: A conformational study of peptides corresponding to loops of brazzein, monellin and thaumatin. *European Journal of Biochemistry* 271, (2004): 2231-2240). Sweet proteins have antiparallel beta-sheets with an alpha-helix perpendicular to the beta-sheets. The sweet proteins thaumatin, monellin, brazzein, and lysozyme tertiary structures were analyzed using PyMOL 2.0 (The PyMOL Molecular Graphics System, Version 2.0 Schrödinger, LLC) and compared to a model of mycodulcein generated with Phyre2 (Kelley L A et al. The Phyre2 web portal for protein modeling, prediction, and analysis Nature Protocols 10, (2015): 845-858) (FIG. 5A). Twenty-three conservative single point mutations of ionic amino acid residues were generated. The negatively charged glutamine and aspartic acids differ by an additional carbon in the aliphatic chain. Although substituting the positively charged lysine and arginine is considered a conservative substitution, the guanidinium of arginine can form additional interactions with amino acids, including hydrogen bonds, aromatic, and aliphatic contacts. The ionic amino acid mutations were lysine to arginine, arginine to lysine, aspartic acid to glutamic acid, and glutamic acid to aspartic acid. The relative positions of each mutant were modelled by PyMOL 2.0 and were categorized as N-terminus, 3 loop regions, 5 beta-sheets, 1 alpha-helix and, the C-terminus (see FIG. 5B.)

Specifically, the following single mutants were generated, and their predicted location is in Table 3. See also FIG. 5B, which shows a representation of SEQ ID NO:3 predicted secondary structure superimposed on putative secondary structure motifs and location of the Table 3 point mutations within each motif.

Cloning: Eco_0001 aka *E. coli* BL21 DE3 (*E. coli* str. B F⁻ ompT gal dcm lon hsdS$_B$(r$_B^-$m$_B^-$) λ(DE3 [lacI lacUV5-T7p07 ind1 sam7 nin5])[malB⁺]$_{K-12}$(λ$^S$)) (obtained from New England Biolabs # C2527I), was transformed with twenty-three plasmids (pMy_3018 to pMy_3040) using manufacturer protocols. In short, previously frozen competent cells were thawed and mixed with 1 pg-100 ng of plasmid DNA and held on ice for 30 minutes. A heat shock of 42° C. for 45 seconds was applied to this mixture. Immediately thereafter, the mixture was placed into an ice bath lasting for 10 minutes. 950 µL of pre-warmed LB media was added and then subjected to 1 hr of 225 rpm shaking at 37° C. Dilution of cells at 1:10 and 1:100 and plating 100 µL on the antibiotic plate was performed for each transformation reaction. An overnight growth at 37° C. allowed colonies to fully recover and become visible. This process yielded strains Z18CE to Z40CE containing the plasmids pMy_3018 to pMy_3040 sequentially. Shake flask-scale induced expression was used to confirm heterologous expression in the *E. coli* host. Post-transformational mutants were plated and maintained on LB+Ampicillin 100 µg/mL agar plates.

Plates were incubated for 16 hours at 37° C. Colony screen PCR was performed to confirm genotypes using colony screening primers designed to interrogate the flanking region along with the cDNA region of the plasmid. A successful transformation resulted in a DNA fragment of a certain size while a negative control and no template control result in no PCR band. Successful transformation was observed for all mutants.

Shake flask-scale induced expression was used to confirm heterologous expression in the *E. coli* host.

23 strains (Z38CE to Z60CE) were maintained on LB+ampicillin 100 µg/mL agar plates while the negative control (Eco_0001) was maintained on a LB agar plate. An overnight culture for each strain in 50 mL of LB liquid media in un-baffled 250 mL culture shake flask at 37° C. shaking 150 rpm overnight with appropriate antibiotics. Each overnight culture was subsequently seeded into 200 mL of TB liquid media the following day into baffled 1000 mL culture shake flask at 37° C. shaking at 200 rpm and adjusted to 0.1 OD600 with the appropriate antibiotic. Once the OD600 reached 0.8, supplement of IPTG was added into the media to a final concentration of 0.66 mM. Continued the shaking at 37° C. for an additional 5 hrs. Afterwards, cells were collected by centrifugation at 5000 g at 4° C. for 5 min. *E. coli* cells were washed once with cold dH$_2$O and centrifuged again at 5000 g at 4° C. for 10 minutes. For confirmation of successful expression, cell lysate was created using liquid nitrogen and a mortar and pestle. The cell pellet was resuspended in 10 mL of cold dH$_2$O and the crude lysate was spun at 20,000 g at 4° C. for 5 minutes. Finally, the supernatant was aspirated and filtered through 0.2 µm PES filter and run on SDS-PAGE protein electrophoresis. Crude lysates were tasted in order to identify sweet-tasting mutants. Table 3 shows results of the testing.

TABLE 3

Results of sweetness testing on single point mutations of mycodulcein

| Content | Sweetness? | PROTEIN SEQ ID NO: | AA Substitution | Hypothesized Location |
|---|---|---|---|---|
| Control-no mutation | Yes | 21 | N/A | N/A |
| Z38CE | Yes | 24 | D3E | N-terminus, exterior surface |
| Z39CE | Yes | 26 | K11R | Beta sheet 1 |
| Z40CE | No | 28 | R20K | Beta Sheet 1, exterior surface |
| Z41CE | Yes | 30 | K26R | Linker region between beta sheet 2 and beta sheet 3 |
| Z42CE | No | 32 | E35D | Linker region between beta sheet 2 and beta sheet 3 |
| Z43CE | No | 34 | K44R | Beta sheet 3 |
| Z44CE | No | 36 | D46E | Beta sheet 3 |
| Z45CE | Yes | 38 | K51R | Loop region 2 |
| Z46CE | No | 40 | D52E | Loop region 2 |
| Z47CE | Yes | 42 | R57K | Loop region 2 |
| Z48CE | Yes | 44 | R66K | Beta sheet 4 |
| Z49CE | Yes | 46 | D69E | Loop region 3 |
| Z50CE | No | 48 | R75K | Beta sheet 5 |
| Z51CE | Yes | 50 | D85E | Alpha helix |
| Z52CE | Yes | 52 | E86D | Alpha helix |
| Z53CE | Yes | 54 | E89D | Alpha helix |
| Z54CE | No | 56 | D94E | C-terminus |
| Z55CE | Yes | 58 | D97E | C-terminus |
| Z56CE | Yes | 60 | K103R | C-terminus |
| Z57CE | Yes | 62 | R106K | C-terminus |
| Z58CE | Yes | 64 | R110K | C-terminus |
| Z59CE | Yes | 66 | E117D | C-terminus |
| Z60CE | Yes | 68 | K120R | C-terminus |

16 of the variants (Z38CE, Z39CE, Z410E, Z45CE, Z47CE, Z48CE, Z49CE, Z510E, Z52CE, Z53CE, Z55CE, Z56CE, Z57CE, Z58CE, Z59CE, Z60CE) all of which had sweet taste were additionally re-expressed using 200 mL of media. After expression, the cells were centrifuged at 4000 g for 20 min after the 24-hour induction period. The supernatant was discarded, and pellet was suspended in ~20 mL of wash buffer (10 mM sodium phosphate buffer pH 7.0). Suspended cells were disrupted in a high-pressure homogenizer (C3 Emulsiflex, Avestin, Inc., Ottawa, ON, Canada) operated at a max of 2,000 bar. Disrupted cells were centrifuged at 13,000 g (30 min), the supernatant was collected, and the pellet was discarded. The supernatant containing solubilized protein was filtered through a 0.22 µm PES membrane unit (Millipore, Burlington, Mass., USA). The material was subsequently isolated through IMAC Purification as described in Example 4.

The purified samples were tasted by a trained sensory scientist. Mycodulcein stocks were diluted to equal protein concentration as measured by ELISA. Subjects followed a sip and spit protocol approved by an Institutional Review Board. 0.2 ml of each purified mutant was placed on the tongue and intensity of sweetness perception, time of onset of sweet perception, and duration of sweetness perception were noted. Results are shown in FIG. 6 and discussed hereinbelow.

Effects of Conservative Point Mutations on Mycodulcein Sweetness

To correlate the effects of conservative single point mutations on sweetness, published mutations of thaumatin, brazzein, monellin and lysozyme were compared to mycodulcein. Since the objective is to match mycodulcein time and intensity profile to sucrose's, we measured sucrose equivalence, onset, and total duration by sensory analysis. Sucrose has a fast onset, high intensity, and fast duration. Thus, mutations that reduce onset and duration are desirable as are mutations that match or improve sucrose equivalency. Mutations that increase onset and total duration are undesirable, as are mutations that decrease sucrose equivalency. See FIGS. 5B and 6.

N-Terminus-Exterior—D3E

The conservative change of a single mutation of D3E at the exterior N-terminus, resulted in the loss of sucrose equivalence and duration; however, the onset was only reduced by slightly. These results suggest that the charge, size, and polarity of sweet proteins N-terminus is important for sweet taste and protein stability.

Beta-Sheet 1—Exterior—K11R

The conservative change of a single mutation at K11R, resulted in a small increase in sucrose equivalence and a moderate reduction in onset; however, the duration of sweetness was dramatically increased. These results suggest that K11 is an important residue for the binding to the sweet taste receptor T1R2/T1R3 and may affect the off rate of mycodulcein from the receptor.

Region Between Beta Sheets 2 and 3—Exterior—K26R—Linker Region

The conservative mutation at K26 resulted in a slight decrease for sucrose equivalence, showing that this conservative mutation does not have a significant effect on protein functionality.

Loop 2 Region-Exterior—K51R

Molecular modelling showed that all putative loop region mutations were solvent exposed. Except for a moderated decrease in onset, only a small decrease in sucrose equivalence and total duration were observed in sensory studies, showing that this conservative mutation does not have a significant effect on protein functionality.

Loop 2 Region-Exterior—R57K

The mutation R57K has a significant inhibitory effect on onset, sucrose equivalence and total duration.

Beta Sheet 4—Exterior—R66K

Mutant R66K has a significant decrease on sucrose equivalence and total duration, while increasing onset slightly. The R66K mutation may be a key residue for affinity and off rate on the sweet taste receptor.

Loop 3 Region-Exterior—D69E

A mutation at D69E has a small decrease for sucrose equivalency, duration, and small increase in duration. It is predicted that this area in this region is relatively insensitive to conservative mutations.

Alpha-Helix Region—Exterior—D85E and D86E

Both D85E and D86E have similar effects on mycodulcein organoleptic properties. Sucrose equivalence and duration for D85E and D86E were reduced. Onset was similar to the control.

C-terminus-exterior-D97E, K103R, R106K, and E117D had minimal effects compared to the control suggesting that these areas are relatively insensitive to conservative mutations. However, R110K and K120R showed decreased sweetness and duration, but onset was similar.

As shown in Table 3, the conservative single point mutations at R20K, E35D, K44R, D46E, D52E, R75K, and D94E, resulted in the loss of protein expression. These data suggest that these residues may be involved in protein folding or expression within the *E. coli* host. The predicted tertiary structure model discussed above in this Example supports protein misfolding resulting from these changes, as all these residues are contained in the predicted beta-sheets.

REFERENCES

Korz, D. J Rinas, U., Hellmuth, K., Sanders, E. A. & Deckwer, W.-D. Simple fed-batch technique for high cell density cultivation of *Escherichia coli*. Journal of Biotechnology 39, 59-65 (1995).

Norsyahida, A., Rahmah, N. & Ahmad, R. M. Y. Effects of feeding and induction strategy on the production of BmR1 antigen in recombinant *E. coli*. Letters in Applied Microbiology 49, 544-550 (2009).

Example 9

Thermal Stability was performed on protein samples from the IMAC Purification of the 16 sweet mutants as described above in Example 8, normalized to 0.04 mg/mL, using the GloMelt™ Thermal Shift Protein Stability Kit (Biotium, Inc. Fremont, Calif.), using instructions provided by the manufacturer. In short, the individual reaction to measure thermal shift relies on mixing the following: mycodulcein, 36 μg/ml in 25 mM sodium phosphate buffer pH 7.4 with reagents provided in the kit per manufacturer's instructions. For the thermal shift measurement, Bio-Rad CFX96 Touch system using BR Clear plates, scan-mode SYBER/FAM only, 25° C. for 30 seconds, melt curve 25° C. to 95° C., increment 0.5° C. for 10 sec plus plate read was used. The Tm is determined based on the midpoint determined for a curve fitted to the experimental data with a five-parameter equation using the techniques as described in Schulz, M. N., Landström, J. & Hubbard, R. E. MTSA—A Matlab program to fit thermal shift data. *Analytical Biochemistry* 433, 43-47 (2013). Results (Table 4) show that thermal stability is minimally affected by the amino acid changes in the mutants tested.

TABLE 4

Results of thermal stability testing for mutants

| PROTEIN SEQ ID NO: | Mutant ID | Tm |
|---|---|---|
| 24 | Z38CE | 58.02135 |
| 26 | Z39CE | 58.9354 |
| 30 | Z41CE | 58.81657 |
| 38 | Z45CE | 60.66312 |
| 42 | Z47CE | 58.48098 |

TABLE 4-continued

Results of thermal stability testing for mutants

| PROTEIN SEQ ID NO: | Mutant ID | Tm |
|---|---|---|
| 44 | Z48CE | 58.99634 |
| 46 | Z49CE | 59.79641 |
| 50 | Z51CE | 59.99543 |
| 52 | Z52CE | 58.81274 |
| 54 | Z53CE | 57.96772 |
| 58 | Z55CE | 60.14034 |
| 60 | Z56CE | 59.29316 |
| 62 | Z57CE | 61.10271 |
| 64 | Z58CE | 57.92335 |
| 68 | Z60Ce | 60.168 |

Example 10 (Cloning and Heterologous Expression of Mycodulcein in *Saccharomyces cerevisiae*; Confirmation of Sweet Taste)

Based on the nucleotide sequence identified as SEQ ID NO:3, two expression vectors to express SEQ ID NO:21 (pMy_4003) (his-tagged) and SEQ ID NO:3 (pMy_4002) (native) mycodulcein were synthesized and cloned by Atum, Inc. (Newark, Calif.) into Atum vector non-secretory backbone pD1234 containing URA3 marker, and strong constitutive promoter GPD. The transformation procedure involves making electrocompetent cells and then introducing expression vectors through electroporation. In short, the electrocompetent cells are created by first growing the cells to between the early and mid-log phase with multiple washes to remove the salt from the growth medium. After mixing 1-5 μg of the expression vector, the sample is subjected to the following settings on a Gene Pulser II Electroporator (Charging Voltage: 1.5 kV, Capacitance: 25 μF, Resistance: 200Ω) 1 mL of prewarmed 30° C. YPD is added immediately, and the suspension is incubated for 1-2 h at 30° C. shaking at 200-250 rpm. Post-transformational mutants were plated and maintained on SC-ura agar plates. This process yielded strains Z19ES, Z20ES containing the plasmids pMy_4002 and pMy_4003 respectively. csPCR (colony screen PCR) was performed to interrogate the cDNA region of the plasmid. Thus, a successful transformation would result in the DNA fragment of 303 bp while a negative control and no template control would result in no PCR band and expression was confirmed.

The two strains (Z19ES, Z20ES) were maintained on SC-ura agar plates while the negative control was maintained on a SC agar plates. An overnight culture of was grown for each strain in 50 mL of SC-ura/SC liquid media in un-baffled 250 mL culture shake flask at 37° C. shaking 150 rpm overnight. Each overnight culture was inoculated into 200 mL of SC-ura/SC (O-RDL-R10_TB Media) liquid media in baffled 1000 mL culture shake flask at 30° C. shaking at 200 rpm and adjusted to 0.02 OD600. The shaking was continued at 30° C. for an additional 48 hrs. Afterwards, cells were collected by centrifugation at 5000 g at 4° C. for 5 min. Afterwards, *S. cerevisiae* cells were washed with cold dH2O and centrifuged again at 5000 g at 4° C. for 5 minutes. For confirmation of successful expression, cells were lysed using liquid nitrogen and a mortar and pestle. Cell pellets were resuspended in 10 mL of cold dH2O and lysate was spun at 20,000 g at 4° C. for 5 minutes. Supernatant was filtered with a 0.2 μm PES filter. The filtrate (both strains) was confirmed to taste sweet by methods described in Example 3.

Thermo Scientific™ HisPur™ Ni-NTA resin was used to purify the his-tagged protein SEQ ID NO:20 from *S. cerevisiae* using effective immobilized metal affinity chromatography (IMAC). SEQ ID NO:20 was purified using nickel-charged nitrilotriacetic acid (NTA) chelate immobilized onto 6% crosslinked agarose resin. Lysate was loaded onto prepared IMAC column, the column was washed three times with 0.02 M imidazole in PBS followed by eluting his-tagged mycodulcein four times with 0.3 M imidazole in PBS followed by ultrafiltration of eluted fractions using a 50 kDa MWCO filter followed by concentration and desalting with a 3 kDa MWCO filter.

Example 11 (Purification of Native Mycodulcein from Strain Z19ES (*S. cerevisiae*))

Three chromatographical techniques were assessed for effectiveness for purification of native mycodulcein (SEQ ID NO:3) expressed in *S. cerevisiae*: cation exchange (CIEX), hydrophobic interaction (HIC), and size exclusion chromatography (SEC).

Cation Exchange Assessment.

Figure 7A:
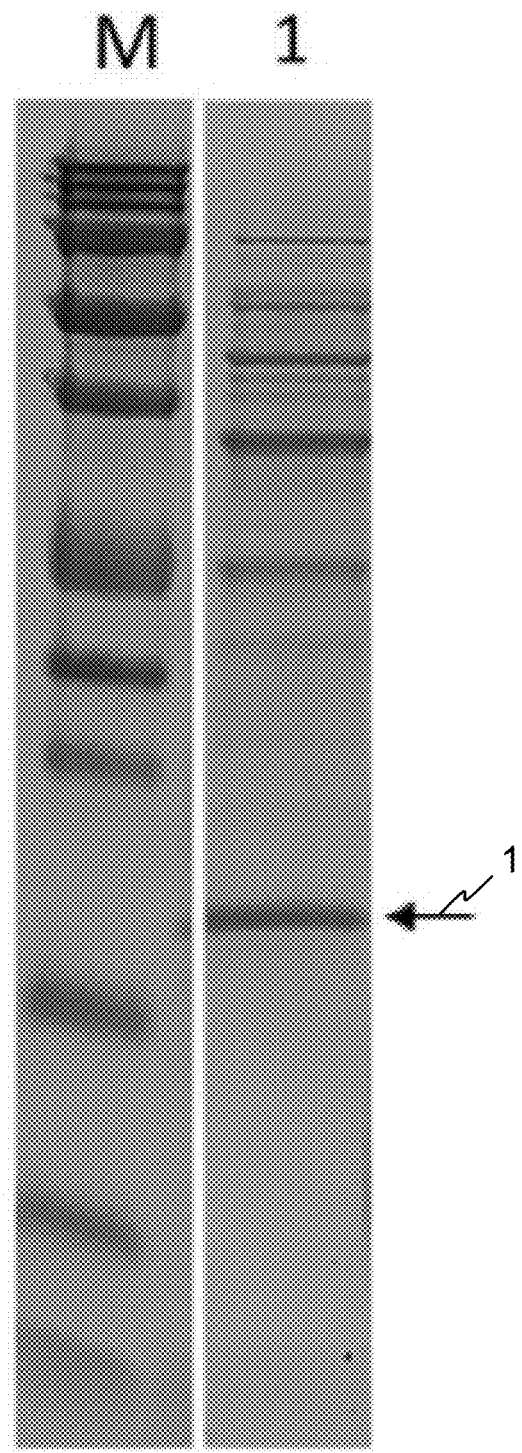
FIG. 7A shows SDS-PAGE analysis, Coomassie stain, of the eluted fraction from Capto MMC. M: protein marker; lane 1: eluted fraction, showing low purity after cation exchange. Arrow (1) indicates mycodulcein band.

The isoelectric point for the native mycodulcein was determined to be ~9.5 by isoelectric focusing, suggesting a cation exchange column might be successful in purifying mycodulcein. The clarified cell lysate prepared as described in Example 10 was mixed with 2× starting buffer to obtain a cell lysate in 50 mM sodium phosphate, 1M ammonium sulfate at pH 7.0, and it was stored at 4° C. for future use. The purification procedure was performed on ÄKTA Explorer 100 system (GE Healthcare, Sweden), and the eluted proteins were monitored at 280 nm and 215 nm on a UV detector UV-900 (GE Healthcare, Sweden). A PreDictor plate (GE Healthcare, Sweden) prefilled with CIEX resins was used to screen binding conditions of native mycodulcein. The prefilled plate contains three main resins: Capto S (strong CIEX), Capto MMC (Weak CIEX), and SP Sepharose Fast Flow (strong CIEX). Lysate was dialyzed into 20 mM sodium phosphate dibasic, and different pH values ranging from 4 to 9 were screened and the optimal conditions were then scaled up using HiScreen column. Equilibration was conducted using 25 mM sodium phosphate dibasic at pH 5 at flow rate of 3 mL/min. Binding proteins were eluted by an increasing sodium chloride gradient from 0 to 1 M using 25 mM sodium phosphate dibasic, 1M sodium chloride at pH 7. Different binding and eluting conditions were screened in which the weak cation exchanger Capto MMC showed the best binding capabilities at pH 5. However, due to low purity (25%) after this step, an alternative purification step was sought. FIG. 7A shows PAGE analysis of the eluted fraction from Capto MMC. M: protein marker; lane 1: eluted fraction, showing low purity after cation exchange. Arrow indicates mycodulcein band.

Hic Assessment.

Cell lysate was also subjected to hydrophobic interaction chromatography (HIC) using HiScreen CaptoButyl column (Cytiva, Sweden); equilibration was carried out using 5 column volumes of 50 mM sodium phosphate, 1M ammonium sulfate at pH 7.0. Cell lysate was then loaded into the column at flow rate of 3 mL/min. Elution of bound proteins was performed by a decreasing ammonium sulfate gradient from 1 to 0 M using 50 mM sodium phosphate at pH 7.0. All obtained fractions were analyzed by SDS-PAGE.

Figure 7B:
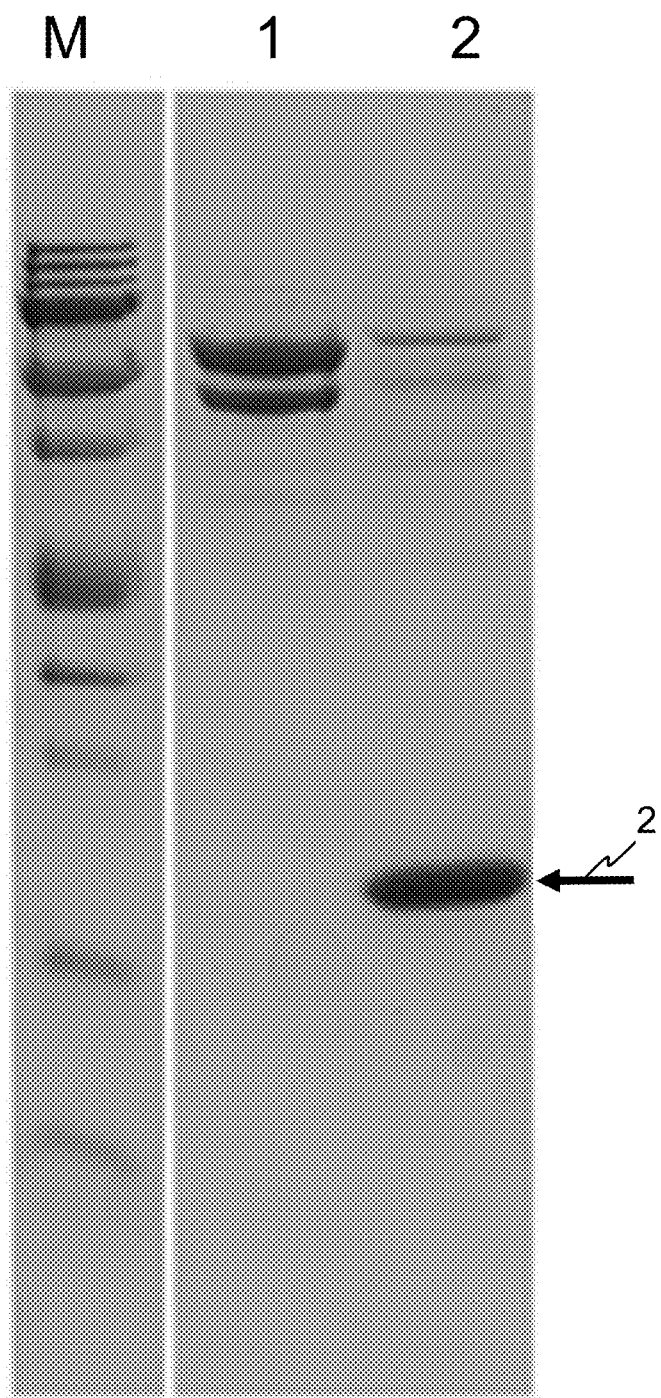
FIG. 7B shows SDS-PAGE analysis, Coomassie stain, two eluted fractions collected during the gradient elution from the HiScreen Capto Butyl column analyzed on SDS-PAGE. Lane 1 shows eluted fraction 1 not containing mycodulcein and Lane 2 shows eluted mycodulcein. The purity of the eluted fraction was determined by GelAnalyzer to be ~86%. Arrow (2) indicates mycodulcein band.

FIG. 7B shows two eluted fractions collected during the gradient elution from the HiScreen Capto Butyl column analyzed on SDS-PAGE. Lane 1 shows eluted fraction 1 not containing mycodulcein and Lane 2 shows eluted mycodulcein. The purity of the eluted fraction was determined by GelAnalyzer to be ~86%.

Sec Assessment.

The eluted fraction containing native mycodulcein was then further purified using size exclusion chromatography (SEC) HiPrep 26/60 Sephacryl S-200 HR column (Cytiva, Sweden), and eluted with buffer containing 50 mM sodium phosphate and 150 mM NaCl at pH 7.0. Fractions were collected and were then concentrated and desalted using 3 kDa molecular weight cut-offs (MWCO) centrifugal filters (Millipore-Sigma, Germany) and then analyzed by SDS-PAGE.

Summary: although native mycodulcein binds successfully to the weak cation exchanger Capto MMC, the relatively low purity of the eluted fraction made CIEX a less favorable capture/intermediate purification step. On the other hand, a higher purity fraction was obtained from the HIC, Capto Butyl column. As per the SDS-PAGE analysis, impurities seemed to have a relatively high molecular weight which made SEC a great candidate to obtain a high pure native mycodulcein.

Figure 7C:
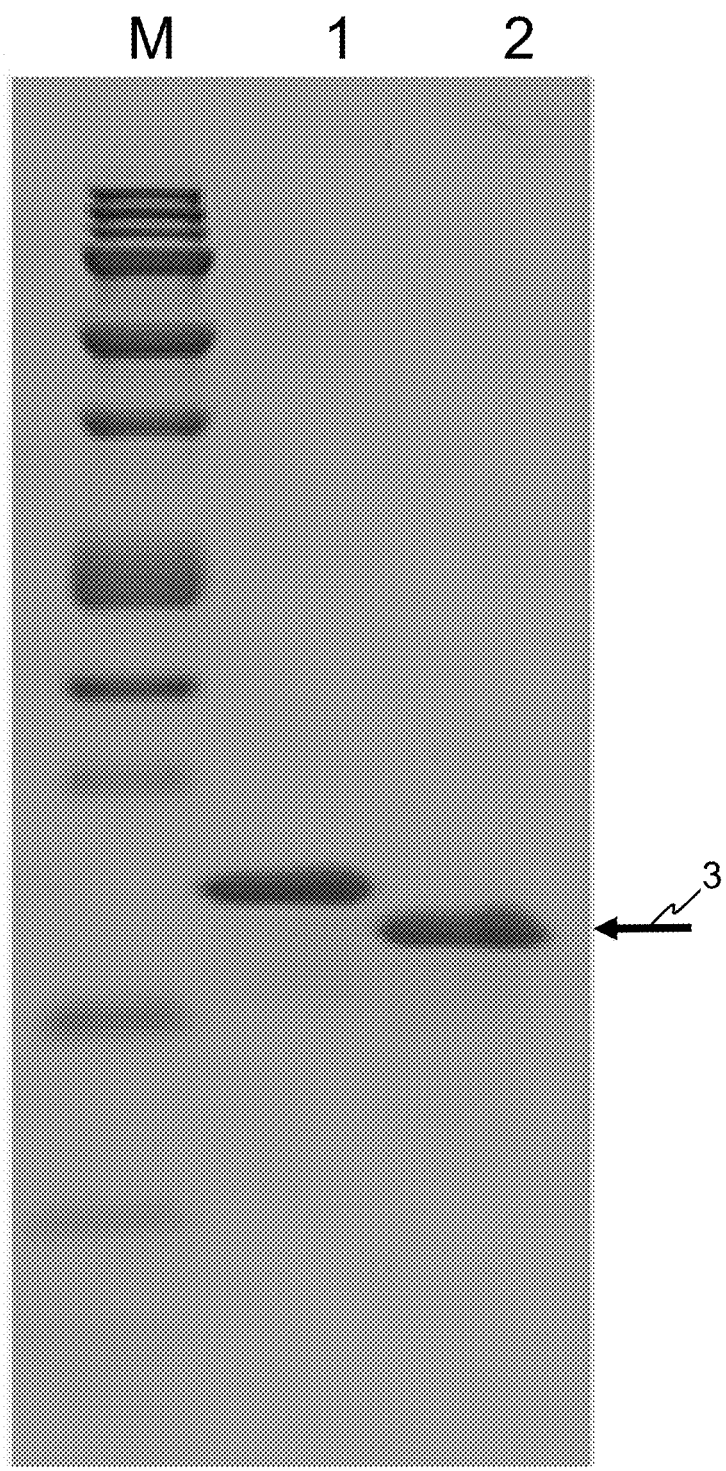
FIG. 7C shows SDS-PAGE analysis, Coomassie stain, the eluted protein from the HIC column after chromatographing on HiPrep 26/60 Sephacryl S-200. Lane 1 shows purified his-tag mycodulcein and Lane 2 shows purified native mycodulcein. The purity of the eluted fraction was determined by GelAnalyzer to be ~98%. Arrow (3) indicates mycodulcein band.

Purity after HIC/SEC is approximately 98% by GelAnalyzer of SDS-PAGE. FIG. 7C shows the eluted protein from the HIC column after chromatographing on HiPrep 26/60 Sephacryl S-200. Lane 1 shows purified his-tag mycodulcein and Lane 2 shows purified native mycodulcein.

The purified native protein purified from S. cerevisiae was tasted at 0.03 mg/ml by a trained sensory scientist (0.2 mL aliquot) and found to have a sweetness equivalent to 8° brix (approximately 8% sugar solution). The sweet taste was very noticeably sweet, with a "clean" sweetness (sugar-like taste) with no other flavors, with a slightly delayed onset and a sweet aftertaste.

Example 12 (Applications Data)

His-tagged mycodulcein prepared as in Example 5 and purified as described in Example 5 was tested in a yogurt base. The yogurt base had the following recipe (Table 5):

TABLE 5

| Ingredient | % |
| --- | --- |
| Water | 81.1200% |
| Pea Protein | 10.6000% |
| Sunflower lecithin | 0.0600% |
| Coconut Oil (AAK) | 5.1000% |
| Ticaloid YG LP (TIC GUMS) | 0.2000% |
| Citri-Fi Citrus Fiber | 0.6000% |
| Canola Oil | 1.0000% |
| Cane Sugar | 1.3000% |
| YoFLEX YF-LO2 Cultures (CHR-Hansen) | 0.0200% |
|  | 0.0000% |
| Total | 100.0000% |

The cane sugar is added as a carbon source for the yogurt cultures and is at least partially consumed by the cultures. Mycodulcein was added to approximate the sweetness from 8° to 10° Brix of sugar, final concentration in the yogurt base is 0.05 mg/ml. Taste testing was performed by a trained sensory scientist and the yogurt was found to have a sweetness equivalent to 8° brix (approximately 8% sugar solution). The sweet taste was very noticeably sweet, with a "clean" sweetness (sugar-like taste) with no other flavors, with a slightly delayed onset and a sweet aftertaste.

His-tagged mycodulcein prepared as in Example 5 and purified as described in Example 5 was tested in whole milk; non-dairy pea-based milk (water, 93.75%, pea protein, 4.2%, canola oil, 1.7%, TIC Gum Blend Pro 181 AG (Acacia+Gellan) 0.3%, sunflower lecithin 0.05%); cold coffee; and water (control) at a final concentration of 0.04 mg/ml, predicted to provide a sweet level of between 8° to 10° Brix of sugar. It was confirmed by taste testing that the sweet protein delivers a sweet level of between 8° to 10° Brix in all samples, and all samples had sweetness intensity, onset, and duration that was similar to the water control.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. The term "consisting of" is construed as a close-ended term (i.e., excluding components or steps other than those listed). The term "consisting essentially of" allows for the inclusion of components or steps that are not essential to the function or activity of the product or method and do not materially affect the function or activity.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An isolated polynucleotide encoding a non naturally occurring variant polypeptide having sweet-taste modulation activity, wherein the polynucleotide sequence encodes a polypeptide selected from the group consisting of:
   (a) a polypeptide having the polypeptide sequence of SEQ ID NO:71, SEQ ID NO:72, SEQ ID NO:73, SEQ ID NO:74, or SEQ ID NO:75;
   (b) a polypeptide having at least 80% sequence identity to the polypeptide sequence of SEQ ID NO:24, SEQ ID NO:26, SEQ ID NO:30, SEQ ID NO:38, SEQ ID NO:42, SEQ ID NO:44, SEQ ID NO:46, SEQ ID NO:50, SEQ ID NO:52, SEQ ID NO:54, SEQ ID NO:58, SEQ ID NO:60, SEQ ID NO:62, SEQ ID NO:64, SEQ ID NO:66, or SEQ ID NO:68; and
   (c) a polypeptide having a polypeptide sequence modified from the polypeptide sequence of SEQ ID NO:24, SEQ ID NO:26, SEQ ID NO:30, SEQ ID NO:38, SEQ ID NO:42, SEQ ID NO:44, SEQ ID NO:46, SEQ ID NO:50, SEQ ID NO:52, SEQ ID NO:54, SEQ ID NO:58, SEQ ID NO:60, SEQ ID NO:62, SEQ ID NO:64, or SEQ ID NO:66, SEQ ID NO:68, by deletion, insertion, substitution, or addition of no more than 24 amino acids,
   wherein the polypeptide having sweet-taste modulation activity is not the polypeptide of SEQ ID NO:3 and is not a naturally occurring Myd (mycodulcein) polypeptide of *Mattirolomyces terfezioides*.

2. The isolated polynucleotide of claim 1, wherein the polypeptide sequence of the polypeptide having sweet-taste modulation activity is SEQ ID NO:71, SEQ ID NO:72, SEQ ID NO:73, SEQ ID NO:74, or SEQ ID NO:75.

3. The isolated polynucleotide of claim 1, wherein the polypeptide sequence of the polypeptide having sweet-taste modulation activity is SEQ ID NO:24, SEQ ID NO:26, SEQ ID NO:30, SEQ ID NO:38, SEQ ID NO:42, SEQ ID NO:44, SEQ ID NO:46, SEQ ID NO:50, SEQ ID NO:52, SEQ ID NO:54, SEQ ID NO:58, SEQ ID NO:60, SEQ ID NO:62, SEQ ID NO:64, SEQ ID NO:66, or SEQ ID NO:68.

4. The isolated polynucleotide of claim 1, operably linked to a heterologous regulatory element.

5. The isolated polynucleotide of claim 1, wherein the polynucleotide sequence further encodes a protein tag.

6. An expression cassette comprising the isolated polynucleotide of claim 1.

7. A vector comprising the isolated polynucleotide of claim 1.

8. A host cell transformed with the vector of claim 7.

9. A method of producing a protein having sweet-taste modulation activity, comprising culturing the host cell of claim 8 in a medium under conditions that result in producing the protein having sweet-taste modulation activity.

10. A polypeptide comprising a polypeptide sequence selected from the group consisting of:
    (a) SEQ ID NO:71, SEQ ID NO:72, SEQ ID NO:73, SEQ ID NO:74, and SEQ ID NO:75;
    (b) a polypeptide sequence having at least 80% sequence identity to polypeptide sequence of SEQ ID NO:24, SEQ ID NO:26, SEQ ID NO:30, SEQ ID NO:38, SEQ ID NO:42, SEQ ID NO:44, SEQ ID NO:46, SEQ ID NO:50, SEQ ID NO:52, SEQ ID NO:54, SEQ ID NO:58, SEQ ID NO:60, SEQ ID NO:62, SEQ ID NO:64, SEQ ID NO:66, or SEQ ID NO:68; and
    (c) a polypeptide sequence modified from the polypeptide sequence SEQ ID NO:24, SEQ ID NO:26, SEQ ID NO:30, SEQ ID NO:38, SEQ ID NO:42, SEQ ID NO:44, SEQ ID NO:46, SEQ ID NO:50, SEQ ID NO:52, SEQ ID NO:54, SEQ ID NO:58, SEQ ID NO:60, SEQ ID NO:62, SEQ ID NO:64, SEQ ID NO:66, or SEQ ID NO:68 by deletion, insertion, substitution, or addition of no more than 24 amino acids;
    wherein the polypeptide is not the polypeptide of SEQ ID NO:3 and is not a naturally occurring Myd (mycodulcein) polypeptide of *Mattirolomyces terfezioides*; and
    wherein the polypeptide has sweet-taste modulation activity.

11. The polypeptide of claim 10, wherein the polypeptide sequence is that of SEQ ID NO:71, SEQ ID NO:72, SEQ ID NO:73, SEQ ID NO:74, or SEQ ID NO:75.

12. The polypeptide of claim 10, wherein the polypeptide sequence is that of SEQ ID NO:24, SEQ ID NO:26, SEQ ID NO:30, SEQ ID NO:38, SEQ ID NO:42, SEQ ID NO:44, SEQ ID NO:46, SEQ ID NO:50, SEQ ID NO:52, SEQ ID NO:54, SEQ ID NO:58, SEQ ID NO:60, SEQ ID NO:62, SEQ ID NO:64, SEQ ID NO:66, or SEQ ID NO:68.

13. The isolated polynucleotide of claim 1, wherein the polynucleotide comprises SEQ ID NO:23, SEQ ID NO:25, SEQ ID NO:29, SEQ ID NO:37, SEQ ID NO:41, SEQ ID NO:43, SEQ ID NO:45, SEQ ID NO:49, SEQ ID NO:51, SEQ ID NO:53, SEQ ID NO:57, SEQ ID NO:59, SEQ ID NO:61, SEQ ID NO:63, SEQ ID NO:65, SEQ ID NO:67 or any of the listed sequences without the sequence encoding the histidine tag.

14. The isolated polynucleotide of claim 1, wherein the polynucleotide sequence further encodes a histidine tag.

15. A composition, comprising a combination of:
    (a) a product for oral administration, wherein the product is not *Mattirolomyces terfezioides* truffle, and
    (b) a sweetening composition comprising an isolated polypeptide, wherein
    the polypeptide is the polypeptide of claim 10, and
    wherein the combination has enhanced sweet taste compared to the product for oral administration.

16. A method for modulating the taste of a product for oral administration, comprising:
    combining the product for oral administration with an effective amount of a sweetening composition comprising an isolated polypeptide, wherein
    the polypeptide is the polypeptide of claim 10,
    wherein the product for oral administration is not *Mattirolomyces terfezioides* truffle, and
    wherein the combination has enhanced sweet taste compared to the product for oral administration.

17. The composition of claim 15, wherein the product for oral administration is a food, a beverage, a dietary supplement composition, or a pharmaceutical composition.

18. The composition of claim 15, wherein the product for oral administration is a food product selected from the group consisting of baked goods; sweet bakery products, pre-made sweet bakery mixes for preparing sweet bakery products; pie fillings and other sweet fillings, gelatins and puddings; frozen desserts; yogurts; snack bars; bread products; pre-made bread mixes for preparing bread products; sauces, syrups and dressings; sweet spreads; confectionary products; and sweetened breakfast cereals.

19. The composition of claim 15, wherein the product for oral administration is a beverage product selected from the group consisting of carbonated beverages; non-carbonated beverages; and beverage concentrates.

20. The method of claim 16, wherein the product for oral administration is a food, a beverage, a dietary supplement composition, or a pharmaceutical composition.

21. The method of claim 16, wherein the product for oral administration is a food product selected from the group consisting of baked goods; sweet bakery products, pre-made sweet bakery mixes for preparing sweet bakery products; pie fillings and other sweet fillings, gelatins and puddings; frozen desserts; yogurts; snack bars; bread products; pre-made bread mixes for preparing bread products; sauces, syrups and dressings; sweet spreads; confectionary products; and sweetened breakfast cereals.

22. The method of claim 16, wherein the product for oral administration is a beverage product selected from the group consisting of carbonated beverages; non-carbonated beverages; and beverage concentrates.

23. A method for purifying a polypeptide having sweet-taste modulation activity comprising:
(a) obtaining a composition comprising the polypeptide,
(b) purifying the composition via hydrophobic interaction chromatography (HIC) followed by size exclusion chromatography (SEC),
wherein
the polypeptide is the polypeptide of claim 10.

24. The isolated polynucleotide of claim 1, wherein the polynucleotide sequence encodes a polypeptide having the polypeptide sequence of SEQ ID NO:75.

25. The isolated polynucleotide of claim 1, wherein the polynucleotide sequence encodes a polypeptide having at least 80% sequence identity to the polypeptide sequence of SEQ ID NO:26.

26. The isolated polynucleotide of claim 1, wherein the polynucleotide sequence encodes a polypeptide having at least 95% sequence identity to the polypeptide sequence of SEQ ID NO:26.

27. The isolated polynucleotide of claim 1, wherein the polynucleotide sequence encodes a polypeptide having the polypeptide sequence of SEQ ID NO:26.

28. The isolated polynucleotide of claim 1, wherein the polynucleotide sequence comprises the polynucleotide sequence of SEQ ID NO:25 with or without the sequence encoding the histidine tau.

29. The polypeptide of claim 10, which is the polypeptide of SEQ ID NO:26.

* * * * *

UNITED STATES PATENT AND TRADEMARK OFFICE
CERTIFICATE OF CORRECTION

| | | |
|---|---|---|
| PATENT NO. | : 12,016,356 B2 | Page 1 of 1 |
| APPLICATION NO. | : 17/680818 | |
| DATED | : June 25, 2024 | |
| INVENTOR(S) | : Marina Nadal et al. | |

It is certified that error appears in the above-identified patent and that said Letters Patent is hereby corrected as shown below:

On the Title Page

Under (72) Inventors: second line Please delete "Anthony J. CLARK, Aurora, OH (US);" and replace with -- Anthony J. CLARK, Aurora CO (US); --.

In the Claims

In Column 123, Line 62, in Claim 10, first line, after the second recitation of "a", please add the phrase -- non naturally occurring variant --.

In Column 126, Line 26, in Claim 28, last line of claim, please delete the word "tau" and replace with -- tag --.

Signed and Sealed this
Twentieth Day of August, 2024

*Katherine Kelly Vidal*

Katherine Kelly Vidal
*Director of the United States Patent and Trademark Office*

SEQUENCE LISTING

<160> NUMBER OF SEQ ID NOS: 75

<210> SEQ ID NO 1
<211> LENGTH: 1072
<212> TYPE: DNA
<213> ORGANISM: Mattirolomyces terfezioides

<400> SEQUENCE: 1

```
caagtcttta agtgttgatc gagcagtaga aatattaatc gcccaattaa ttgctcttac      60
tctaggaaat gtagtactca agttggccct ctaagtccct gattcagtgt cacttttttct   120
cctttgacag taggctagat tctagctctt gtgtccgttt cttaaaatcc tgatatggca    180
ccttagcgtc agagcagaat acctgttctc atacaccttg gctatgatcc gatatttaaa    240
tagagcaatc acccttctgg atatcttccc catagctccc attgacctca acatttttct    300
aatcccctat accagccata ttacttgtct aagcacttca cattcttcct cacaatacga    360
aacctcctaa aatgcctgat ctctcctcct tcattacgat aagaacaac tctaaccacg     420
tcttcactcg gacggcaatt tattctaagt atgccgctgt gcagtggagt cccgagccgc    480
aactctcaat ctctcccggc aaatgggatt tgtttatttt aaaggacatc ttgtctatcc    540
gtgggacttc gggatatgta caatatcggg ttggggatgg tcctggatgg gttagggtca    600
ccttttcttc tctagtcggg gccgatgaag tggcagagtg gagctcaggt gacctacctg    660
atggctttgt tctccaaaaa ccagttcgca ctgggtccag gcctttgcag gcaacgttcg    720
aggctacaaa acagtaaaga tcgatgatgc ctaatatgcc tccataacac tgacccgcgt    780
gcacatggcc gcatgaatga taaggggat atcgatgatg atgggattag ttattggaat     840
tttcacaatg gacgtcggct tggatttaca ataatcgttt catttgtatt caaatattcc    900
tatttccttg ggttttttgta tttatctcct tcatcacgcc ttctgaggcc gtgggaagat   960
gaatatgtaa tcaaaagaag ttaggatatg catcatgtac agaaagtgga ccgcaacccc   1020
ttcagcgaaa tgttataaag atgatatcta agacgccaaa gcacattctc ag           1072
```

<210> SEQ ID NO 2
<211> LENGTH: 366
<212> TYPE: DNA
<213> ORGANISM: Mattirolomyces terfezioides

<400> SEQUENCE: 2

```
atgcctgatc tctcctcctt cattacgatt aagaacaact ctaaccacgt cttcactcgg      60
acggcaattt attctaagta tgccgctgtg cagtggagtc ccgagccgca actctcaatc    120
tctcccggca aatgggattt gtttatttta aaggacatct tgtctatccg tgggacttcg    180
ggatatgtac aatatcgggt tggggatggt cctggatggg ttagggtcac cttttcttct    240
ctagtcgggg ccgatgaagt ggcagagtgg agctcaggtg acctacctga tggctttgtt    300
ctccaaaaac cagttcgcac tgggtccagg cctttgcagg caacgttcga ggctacaaaa    360
cagtaa                                                                366
```

<210> SEQ ID NO 3
<211> LENGTH: 121
<212> TYPE: PRT
<213> ORGANISM: Mattirolomyces terfezioides

<400> SEQUENCE: 3

```
Met Pro Asp Leu Ser Ser Phe Ile Thr Ile Lys Asn Asn Ser Asn His
1               5                   10                  15
```

Val Phe Thr Arg Thr Ala Ile Tyr Ser Lys Tyr Ala Ala Val Gln Trp
            20                  25                  30

Ser Pro Glu Pro Gln Leu Ser Ile Ser Pro Gly Lys Trp Asp Leu Phe
        35                  40                  45

Ile Leu Lys Asp Ile Leu Ser Ile Arg Gly Thr Ser Gly Tyr Val Gln
    50                  55                  60

Tyr Arg Val Gly Asp Gly Pro Gly Trp Val Arg Val Thr Phe Ser Ser
65                  70                  75                  80

Leu Val Gly Ala Asp Glu Val Ala Glu Trp Ser Ser Gly Asp Leu Pro
                85                  90                  95

Asp Gly Phe Val Leu Gln Lys Pro Val Arg Thr Gly Ser Arg Pro Leu
            100                 105                 110

Gln Ala Thr Phe Glu Ala Thr Lys Gln
        115                 120

<210> SEQ ID NO 4
<211> LENGTH: 20
<212> TYPE: PRT
<213> ORGANISM: Mattirolomyces terfezioides

<400> SEQUENCE: 4

Pro Asp Leu Ser Ser Phe Ile Thr Ile Lys Asn Asn Ser Asn His Val
1               5                   10                  15

Phe Thr Arg Thr
            20

<210> SEQ ID NO 5
<211> LENGTH: 873
<212> TYPE: DNA
<213> ORGANISM: Pisolithus tincturius

<400> SEQUENCE: 5
tcgtccgagc agataaacat cgacgggcag gatgtcattt ctactgaatg tctggaacgc      60
tgtccaggcc cgaggtacaa tcttcctatc aacgacgcag acgaggtaca atactgctgt     120
caatgctaca aaatcatgcc gggtcctgtg catggccgtc tgaggaggtt cttctggtag     180
aagtttaaaa ggtctctggg cgacgggtgt aacttgccaa tttcccctac atccgaacat     240
ggcagatgaa cagaaggaac tcgcaaccaa cgtagccgac catggtctta ctggccaact     300
tccctcatca aacgaaacca cggagggact cggagtcacg caagactgct cttgctacat     360
cacgctccac aatgggaccg accatgagct tgtgctcgtc tacgctcaag agaaacacgg     420
tgaatggaag acccgccctg cggaaaccgt gagccagaag agcaatatca agttttggct     480
caaagactta ttccttggtc ctggagcaga gggtatggtg aagtatcgaa tcggaagtac     540
cgagcacaag gtgcagatga acttcagctg tcctatgtct tctcccaact cggcgtcctg     600
gagtcaaggt gaacatgaga ttccaggcat ctggttgccc tgtccggaat acaataaatc     660
tgatgcgttg catgccgtgt ttgaagtaca acctgggaat taaggcgtcg gggcggggag     720
acgtactata ccccattgtc gatagcctct ggaagtgtca tcataatgac tgtttgtttt     780
gtcattgacc ggcgacttgt cattttgagt tcgtttccct tggcctgagg cgcacttacc     840
gggcatcgtc atagagctac tgcttaccac aaa                                  873

<210> SEQ ID NO 6
<211> LENGTH: 464
<212> TYPE: DNA
<213> ORGANISM: Pisolithus tincturius

<400> SEQUENCE: 6

```
atggcagatg aacagaagga actcgcaacc aacgtagccg accatggtct tactggccaa      60
cttccctcat caaacgaaac cacggaggga ctcggagtca cgcaagactg ctcttgctac     120
atcacgctcc acaatgggac cgaccatgag cttgtgctcg tctacgctca agagaaacac     180
ggtgaatgga agacccgccc tgcggaaacc gtgagccaga gagcaatat caagttttgg      240
ctcaaagact tattccttgg tcctggagca gagggtatgg tgaagtatcg aatcggaagt     300
accgagcaca aggtgcagat gaacttcagc tgtcctatgt cttctcccaa ctcggcgtcc     360
tggagtcaag gtgaacatga gattccaggc atctggttgc cctgtccgga atacaataaa     420
tctgatgcgt tgcatgccgt gtttgaagta caacctggga atta                      464
```

<210> SEQ ID NO 7
<211> LENGTH: 154
<212> TYPE: PRT
<213> ORGANISM: Pisolithus tincturius

<400> SEQUENCE: 7

```
Met Ala Asp Glu Gln Lys Glu Leu Ala Thr Asn Val Ala Asp His Gly
1               5                   10                  15
Leu Thr Gly Gln Leu Pro Ser Ser Asn Glu Thr Thr Glu Gly Leu Gly
            20                  25                  30
Val Thr Gln Asp Cys Ser Cys Tyr Ile Thr Leu His Asn Gly Thr Asp
        35                  40                  45
His Glu Leu Val Leu Val Tyr Ala Gln Glu Lys His Gly Glu Trp Lys
    50                  55                  60
Thr Arg Pro Ala Glu Thr Val Ser Gln Lys Ser Asn Ile Lys Phe Trp
65                  70                  75                  80
Leu Lys Asp Leu Phe Leu Gly Pro Gly Ala Glu Gly Met Val Lys Tyr
                85                  90                  95
Arg Ile Gly Ser Thr Glu His Lys Val Gln Met Asn Phe Ser Cys Pro
            100                 105                 110
Met Ser Ser Pro Asn Ser Ala Ser Trp Ser Gln Gly Glu His Glu Ile
        115                 120                 125
Pro Gly Ile Trp Leu Pro Cys Pro Glu Tyr Asn Lys Ser Asp Ala Leu
    130                 135                 140
His Ala Val Phe Glu Val Gln Pro Gly Asn
145                 150
```

<210> SEQ ID NO 8
<211> LENGTH: 121
<212> TYPE: PRT
<213> ORGANISM: Artificial Sequence
<220> FEATURE:
<223> OTHER INFORMATION: Mutated protein from Mattirolomyces
      terfezioides

<400> SEQUENCE: 8

```
Met Pro Asp Leu Ser Ser Phe Ile Thr Ile Lys His Asn Ser His His
1               5                   10                  15
Val Phe Thr Arg Thr Ala Ile Tyr Ser Lys Tyr Ala Ala Val Gln Trp
            20                  25                  30
Ser Gln Glu Pro His Leu Ser Ile Ser Pro Gly Lys Trp Asp Leu Phe
        35                  40                  45
Ile Leu Lys Asp Ile Leu Ser Ile Arg Gly Thr Ser Gly Tyr Val Gln
    50                  55                  60
```

```
Tyr Arg Val Gly Ala Ala Gln Gly Trp Val Arg Val Thr Phe Ser Ser
 65                  70                  75                  80

Leu Val Gly Ala Asp Glu Val Ala Glu Trp Ser Ser Gly Asp Leu Pro
                 85                  90                  95

Asp Gly Phe Val Trp His Gln Gln Val Thr Thr Gly Ser Arg Pro Leu
            100                 105                 110

Gln Ala Thr Phe Glu Ala Thr Lys Gln
        115                 120
```

<210> SEQ ID NO 9
<211> LENGTH: 121
<212> TYPE: PRT
<213> ORGANISM: Artificial Sequence
<220> FEATURE:
<223> OTHER INFORMATION: Mutated protein from Mattirolomyces
      terfezioides

<400> SEQUENCE: 9

```
Met Pro Asp Leu Ser Ser Phe Ile Thr Ile Lys Asn Asn Thr Asp His
 1               5                  10                  15

Val Phe Thr Arg Thr Ala Ile Tyr Ser Lys Tyr Ala Ala Val Gln Trp
                 20                  25                  30

Ser Pro Gln Pro Gln Leu Ser Ile Ser His Gly Lys Trp Asp Leu Phe
             35                  40                  45

Ile Leu Lys Asp Ile Leu Ser Ile Arg Gly Thr Ser Gly Tyr Val Gln
 50                  55                  60

Tyr Arg Val Gly His Gly Pro Asp Trp Val Arg Val Thr Phe Ser Ser
 65                  70                  75                  80

Leu Val Gly Ala Asp Glu Val Ala Glu Trp Ser Ser Gly Asp Leu Pro
                 85                  90                  95

Asp Gly Phe Val Trp His Glu His Val Pro Met Gly Ser Arg Pro Leu
            100                 105                 110

Gln Ala Thr Phe Glu Ala Thr Lys Gln
        115                 120
```

<210> SEQ ID NO 10
<211> LENGTH: 121
<212> TYPE: PRT
<213> ORGANISM: Artificial Sequence
<220> FEATURE:
<223> OTHER INFORMATION: Mutated protein from Mattirolomyces
      terfezioides

<400> SEQUENCE: 10

```
Met Pro Asp Leu Ser Ser Phe Ile Thr Ile Lys Asn Lys Pro Asn His
 1               5                  10                  15

Val Phe Thr Arg Thr Ala Ile Tyr Ser Lys Tyr Ala Ala Val Gln Trp
                 20                  25                  30

Ser Ser Glu Ser Gln Leu Ser Ile Pro Ser Gly Glu Trp Asp Leu Phe
             35                  40                  45

Ile Leu Lys Asp Ile Leu Ser Ile Arg Gly Thr Ser Gly Tyr Val Gln
 50                  55                  60

Tyr Arg Val Gly Val Gly Ser Cys Trp Val Arg Val Thr Phe Ser Ser
 65                  70                  75                  80

Leu Val Gly Ala Asp Glu Val Ala Glu Trp Ser Ser Gly Asp Leu Pro
                 85                  90                  95

Asp Gly Phe Val Leu Gln Lys Ser Val Gln Thr Gly Ser Arg Pro Leu
            100                 105                 110
```

Gln Ala Thr Phe Glu Ala Thr Lys Gln
        115                 120

<210> SEQ ID NO 11
<211> LENGTH: 121
<212> TYPE: PRT
<213> ORGANISM: Artificial Sequence
<220> FEATURE:
<223> OTHER INFORMATION: Mutated protein from Mattirolomyces
      terfezioides

<400> SEQUENCE: 11

Met Pro Asp Leu Ser Ser Phe Ile Thr Ile Lys Asn His Thr Asn Arg
1               5                   10                  15

Val Phe Thr Arg Thr Ala Ile Tyr Ser Lys Tyr Ala Ala Val Gln Trp
            20                  25                  30

Thr Pro Glu Ser Leu Met Ser Ile Ser Pro Gly Thr Trp Asp Leu Phe
        35                  40                  45

Ile Leu Lys Asp Ile Leu Ser Ile Arg Gly Thr Ser Gly Tyr Val Gln
    50                  55                  60

Tyr Arg Val Gly Asp Cys Pro Gly Trp Val Arg Val Thr Phe Ser Ser
65                  70                  75                  80

Leu Val Gly Ala Asp Glu Val Ala Glu Trp Ser Ser Gly Asp Leu Pro
                85                  90                  95

Asp Gly Phe Val Leu Gln Lys Pro Val Gln Met Gly Thr Arg Pro Leu
            100                 105                 110

Gln Ala Thr Phe Glu Ala Thr Lys Gln
        115                 120

<210> SEQ ID NO 12
<211> LENGTH: 121
<212> TYPE: PRT
<213> ORGANISM: Artificial Sequence
<220> FEATURE:
<223> OTHER INFORMATION: Mutated protein from Mattirolomyces
      terfezioides

<400> SEQUENCE: 12

Met Pro Asp Leu Ser Ser Phe Ile Thr Ile Lys Asp Asn Ser Asn Gln
1               5                   10                  15

Val Phe Thr Arg Thr Ala Ile Tyr Ser Lys Tyr Ala Ala Val Gln Trp
            20                  25                  30

Cys Pro Glu Leu Pro Arg Ser Ile Ser Leu Gly Lys Trp Asp Leu Phe
        35                  40                  45

Ile Leu Lys Asp Ile Leu Ser Ile Arg Gly Thr Ser Gly Tyr Val Gln
    50                  55                  60

Tyr Arg Val Gly Asp Ala Leu Ala Trp Val Arg Val Thr Phe Ser Ser
65                  70                  75                  80

Leu Val Gly Ala Asp Glu Val Ala Glu Trp Ser Ser Gly Asp Leu Pro
                85                  90                  95

Asp Gly Phe Val Leu Gln Lys Leu Val Arg Asn Gly Ser Arg Pro Leu
            100                 105                 110

Gln Ala Thr Phe Glu Ala Thr Lys Gln
        115                 120

<210> SEQ ID NO 13
<211> LENGTH: 121
<212> TYPE: PRT
<213> ORGANISM: Artificial Sequence
<220> FEATURE:

<223> OTHER INFORMATION: Mutated protein from Mattirolomyces terezoides

<400> SEQUENCE: 13

Met Pro Asp Leu Ser Ser Phe Ile Thr Ile Lys His Asn Ala His
1               5                   10                  15

Val Phe Thr Arg Thr Ala Ile Tyr Ser Lys Tyr Ala Ala Val Gln Trp
            20                  25                  30

Ser Gln Glu Gln Gln Leu Ser Ile Ala Pro Gly Thr Trp Asp Leu Phe
        35                  40                  45

Ile Leu Lys Asp Ile Leu Ser Ile Arg Gly Thr Ser Gly Tyr Val Gln
50                  55                  60

Tyr Arg Val Arg Asp Gly Pro Gly Trp Val Arg Val Thr Phe Ser Ser
65                  70                  75                  80

Leu Val Gly Ala Asp Glu Val Ala Glu Trp Ser Ser Gly Asp Leu Pro
                85                  90                  95

Asp Gly Phe Val Leu Gln Lys Gln Val Arg Lys Arg Ala Arg Pro Leu
            100                 105                 110

Gln Ala Thr Phe Glu Ala Thr Lys Gln
        115                 120

<210> SEQ ID NO 14
<211> LENGTH: 121
<212> TYPE: PRT
<213> ORGANISM: Artificial Sequence
<220> FEATURE:
<223> OTHER INFORMATION: Mutated protein from Mattirolomyces
      terfezioides

<400> SEQUENCE: 14

Met Pro Asp Leu Ser Ser Phe Ile Thr Ile Lys Asn His Ser Asn Asn
1               5                   10                  15

Val Phe Thr Arg Thr Ala Ile Tyr Ser Lys Tyr Ala Ala Val Gln Trp
            20                  25                  30

Pro Arg Gly Pro Leu Leu Ser Ile Ser Pro Arg Gln Trp Asp Leu Phe
        35                  40                  45

Ile Leu Lys Asp Ile Leu Ser Ile Arg Gly Thr Ser Gly Tyr Val Gln
50                  55                  60

Tyr Arg Val Gly Asp Gly Arg Gly Trp Val Arg Val Thr Phe Ser Ser
65                  70                  75                  80

Leu Val Gly Ala Asp Glu Val Ala Glu Trp Ser Ser Gly Asp Leu Pro
                85                  90                  95

Asp Gly Phe Val Leu Gln Lys Arg Val Gly Asn Gly Ser Arg Pro Leu
            100                 105                 110

Gln Ala Thr Phe Glu Ala Thr Lys Gln
        115                 120

<210> SEQ ID NO 15
<211> LENGTH: 121
<212> TYPE: PRT
<213> ORGANISM: Artificial Sequence
<220> FEATURE:
<223> OTHER INFORMATION: Mutated protein from Mattirolomyces
      terfezioides

<400> SEQUENCE: 15

Met Pro Asp Leu Ser Ser Phe Ile Thr Ile Lys Asn Asn

Ser His Gln Pro Arg Pro Ser Ile Trp Pro Asp Met Trp Asp Leu Phe
        35                  40                  45

Ile Leu Lys Asp Ile Leu Ser Ile Arg Gly Thr Ser Gly Tyr Val Gln
    50                  55                  60

Tyr Arg Val Gly Asp Asp Pro Gly Trp Val Arg Val Thr Phe Ser Ser
65                  70                  75                  80

Leu Val Gly Ala Asp Glu Val Ala Glu Trp Ser Ser Gly Asp Leu Pro
                85                  90                  95

Asp Gly Phe Val Leu Arg Met Pro Asp Pro Thr Gly Ser Arg Pro Leu
            100                 105                 110

Gln Ala Thr Phe Glu Ala Thr Lys Gln
        115                 120

<210> SEQ ID NO 16
<211> LENGTH: 121
<212> TYPE: PRT
<213> ORGANISM: Artificial Sequence
<220> FEATURE:
<223> OTHER INFORMATION: Mutated protein from Mattirolomyces
      terfezioides

<400> SEQUENCE: 16

Met Pro Asp Leu Ser Ser Phe Ile Thr Ile Lys Asp Pro Asn Gln
1               5                   10                  15

Val Phe Thr Arg Thr Ala Ile Tyr Ser Lys Tyr Ala Ala Val Gln Trp
                20                  25                  30

Ser Pro Glu His Gln Phe Ser Ile Ser Pro Gly Lys Trp Asp Leu Phe
        35                  40                  45

Ile Leu Lys Asp Ile Leu Ser Ile Arg Gly Thr Ser Gly Tyr Val Gln
    50                  55                  60

Tyr Arg Val Cys Asp Cys Pro Gly Trp Val Arg Val Thr Phe Ser Ser
65                  70                  75                  80

Leu Val Gly Ala Asp Glu Val Ala Glu Trp Ser Ser Gly Asp Leu Pro
                85                  90                  95

Asp Gly Phe Val Phe Gln Thr Pro Val Thr Thr Gly Pro Arg Pro Leu
            100                 105                 110

Gln Ala Thr Phe Glu Ala Thr Lys Gln
        115                 120

<210> SEQ ID NO 17
<211> LENGTH: 121
<212> TYPE: PRT
<213> ORGANISM: Artificial Sequence
<220> FEATURE:
<223> OTHER INFORMATION: Mutated protein from Mattirolomyces
      terfezioides

<400> SEQUENCE: 17

Met Pro Asp Leu Ser Ser Phe Ile Thr Ile Lys Asn Lys Thr Asn His
1               5                   10                  15

Val Phe Thr Arg Thr Ala Ile Tyr Ser Lys Tyr Ala Ala Val Gln Trp
                20                  25                  30

Thr Gln Gln Pro Gln Ile Ser Ile Thr Gln Gly Lys Trp Asp Leu Phe
        35                  40                  45

Ile Leu Lys Asp Ile Leu Ser Ile Arg Gly Thr Ser Gly Tyr Val Gln
    50                  55                  60

Tyr Arg Val Gly Asp Asp Pro Gly Trp Val Arg Val Thr Phe Ser Ser
65                  70                  75                  80

Leu Val Gly Ala Asp Glu Val Ala Glu Trp Ser Ser Gly Asp Leu Pro
            85                  90                  95

Asp Gly Phe Val Leu Arg Lys Pro Leu Arg Met Gly Ser Arg Pro Leu
            100                 105                 110

Gln Ala Thr Phe Glu Ala Thr Lys Gln
            115                 120

<210> SEQ ID NO 18
<211> LENGTH: 58
<212> TYPE: DNA
<213> ORGANISM: Artificial Sequence
<220> FEATURE:
<223> OTHER INFORMATION: Synthetic Adapter Sequence

<400> SEQUENCE: 18
aatgatacgg cgaccaccga gatctacact ctttccctac acgacgctct tccgatct         58

<210> SEQ ID NO 19
<211> LENGTH: 58
<212> TYPE: DNA
<213> ORGANISM: Artificial Sequence
<220> FEATURE:
<223> OTHER INFORMATION: Synthetic Adapter Sequence
<220> FEATURE:
<221> NAME/KEY: misc_feature
<222> LOCATION: (34)..(34)
<223> OTHER INFORMATION: insertion of i7 barcode

<400> SEQUENCE: 19
gatcggaaga gcacacgtct gaactccagt cacnatctcg tatgccgtct tctgcttg         58

<210> SEQ ID NO 20
<211> LENGTH: 384
<212> TYPE: DNA
<213> ORGANISM: Artificial Sequence
<220> FEATURE:
<223> OTHER INFORMATION: Modified coding sequence for E. coli expression
      for protein from Mattirolomyces terfezioides with His-Tag
<220> FEATURE:
<221> NAME/KEY: CDS
<222> LOCATION: (1)..(384)

<400> SEQUENCE: 20 atg ccg gat ttg agc tcg ttc att act att aag aat aac tct aac cat        48
Met Pro Asp Leu Ser Ser Phe Ile Thr Ile Lys Asn Asn Ser Asn His
1               5                   10                  15 gtt ttt acg cgt acc gca atc tat tcc aaa tat gcc gca gtc cag tgg        96
Val Phe Thr Arg Thr Ala Ile Tyr Ser Lys Tyr Ala Ala Val Gln Trp
                20                  25                  30 agc ccg gaa ccg cag ctg agc att agc cca ggt aaa tgg gac ctg ttc       144
Ser Pro Glu Pro Gln Leu Ser Ile Ser Pro Gly Lys Trp Asp Leu Phe
            35                  40                  45 atc ctg aaa gac atc ctg agc atc cgc ggt acg tcc ggc tac gtg cag       192
Ile Leu Lys Asp Ile Leu Ser Ile Arg Gly Thr Ser Gly Tyr Val Gln
        50                  55                  60 tac cgt gtc ggc gac ggt ccg ggc tgg gtg cgt gtt acc ttt agc agc       240
Tyr Arg Val Gly Asp Gly Pro Gly Trp Val Arg Val Thr Phe Ser Ser
65                  70                  75                  80 ctg gtg ggt gcg gac gaa gtt gct gag tgg agc agc ggt gat ctg ccg       288
Leu Val Gly Ala Asp Glu Val Ala Glu Trp Ser Ser Gly Asp Leu Pro
                85                  90                  95 gat ggc ttt gtt ctg caa aag cct gtc cgc acc ggt agc cgt ccg ctg       336
Asp Gly Phe Val Leu Gln Lys Pro Val Arg Thr Gly Ser Arg Pro Leu
                100                 105                 110

```
caa gcg acg ttc gag gcg acc aag caa cat cac cat cac cac cac taa      384
Gln Ala Thr Phe Glu Ala Thr Lys Gln His His His His His His
        115                 120                 125
```

<210> SEQ ID NO 21
<211> LENGTH: 127
<212> TYPE: PRT
<213> ORGANISM: Artificial Sequence
<220> FEATURE:
<223> OTHER INFORMATION: Synthetic Construct

<400> SEQUENCE: 21

```
Met Pro Asp Leu Ser Ser Phe Ile Thr Ile Lys Asn Asn Ser Asn His
1               5                   10                  15

Val Phe Thr Arg Thr Ala Ile Tyr Ser Lys Tyr Ala Ala Val Gln Trp
            20                  25                  30

Ser Pro Glu Pro Gln Leu Ser Ile Ser Pro Gly Lys Trp Asp Leu Phe
        35                  40                  45

Ile Leu Lys Asp Ile Leu Ser Ile Arg Gly Thr Ser Gly Tyr Val Gln
    50                  55                  60

Tyr Arg Val Gly Asp Gly Pro Gly Trp Val Arg Val Thr Phe Ser Ser
65                  70                  75                  80

Leu Val Gly Ala Asp Glu Val Ala Glu Trp Ser Ser Gly Asp Leu Pro
                85                  90                  95

Asp Gly Phe Val Leu Gln Lys Pro Val Arg Thr Gly Ser Arg Pro Leu
            100                 105                 110

Gln Ala Thr Phe Glu Ala Thr Lys Gln His His His His His
        115                 120                 125
```

<210> SEQ ID NO 22
<211> LENGTH: 366
<212> TYPE: DNA
<213> ORGANISM: Artificial Sequence
<220> FEATURE:
<223> OTHER INFORMATION: Modified coding sequence for Saccharomyces
      cerevisiae expression for protein from Mattirolomyces terfezioides
      with His-Tag

<400> SEQUENCE: 22

```
atgcctgatt tatcaagttt tatcaccatt aaaaataact ctaaccatgt ttttactaga      60
acagccatct actcaaagta cgcagccgtc caatggtccc cagaacctca gttgtctata     120
tctccaggta atgggatctt tttcatctta aaagatattc taagtattag aggcacttct     180
ggttacgtac agtatcgtgt tggtgatgga cctggttggg ttagagtaac attcagctca     240
ttggttgggg ctgacgaagt ggctgagtgg tcctcaggtg acctcccaga tggcttcgtg     300
ctgcaaaagc cagtcagaac tggatctaga ccattgcaag cgacattcga agcaacaaag     360
caatga                                                                366
```

<210> SEQ ID NO 23
<211> LENGTH: 384
<212> TYPE: DNA
<213> ORGANISM: Artificial Sequence
<220> FEATURE:
<223> OTHER INFORMATION: Coding Sequence for modfied protein from
      Mattirolomyces terfezioides including His-Tag

<400> SEQUENCE: 23

```
atgccggaat tgagctcgtt cattactatt aagaataact ctaaccatgt ttttacgcgt      60
accgcaatct attccaaata tgccgcagtc cagtggagcc cggaaccgca gctgagcatt     120
```

```
agcccaggta atgggaccct gttcatcctg aaagacatcc tgagcatccg cggtacgtcc    180
ggctacgtgc agtaccgtgt cggcgacggt ccgggctggg tgcgtgttac ctttagcagc    240
ctggtgggtg cggacgaagt tgctgagtgg agcagcggtg atctgccgga tggctttgtt    300
ctgcaaaagc ctgtccgcac cggtagccgt ccgctgcaag cgacgttcga ggcgaccaag    360
caacatcacc accaccacca ctaa                                          384
```

```
<210> SEQ ID NO 24
<211> LENGTH: 127
<212> TYPE: PRT
<213> ORGANISM: Artificial Sequence
<220> FEATURE:
<223> OTHER INFORMATION: Modified protein from Mattirolomyces
      terfezioides with optional His-Tag
<220> FEATURE:
<221> NAME/KEY: misc_feature
<222> LOCATION: (122)..(127)
<223> OTHER INFORMATION: Absent or Histidine

<400> SEQUENCE: 24
```

```
Met Pro Glu Leu Ser Ser Phe Ile Thr Ile Lys Asn Asn Ser Asn His
1               5                   10                  15

Val Phe Thr Arg Thr Ala Ile Tyr Ser Lys Tyr Ala Ala Val Gln Trp
            20                  25                  30

Ser Pro Glu Pro Gln Leu Ser Ile Ser Pro Gly Lys Trp Asp Leu Phe
        35                  40                  45

Ile Leu Lys Asp Ile Leu Ser Ile Arg Gly Thr Ser Gly Tyr Val Gln
    50                  55                  60

Tyr Arg Val Gly Asp Gly Pro Gly Trp Val Arg Val Thr Phe Ser Ser
65                  70                  75                  80

Leu Val Gly Ala Asp Glu Val Ala Glu Trp Ser Ser Gly Asp Leu Pro
                85                  90                  95

Asp Gly Phe Val Leu Gln Lys Pro Val Arg Thr Gly Ser Arg Pro Leu
            100                 105                 110

Gln Ala Thr Phe Glu Ala Thr Lys Gln Xaa Xaa Xaa Xaa Xaa Xaa
        115                 120                 125
```

```
<210> SEQ ID NO 25
<211> LENGTH: 384
<212> TYPE: DNA
<213> ORGANISM: Artificial Sequence
<220> FEATURE:
<223> OTHER INFORMATION: Coding Sequence of modified protein from
      Mattirolomyces terfezioides with His-Tag

<400> SEQUENCE: 25
```

```
atgccggatt tgagctcgtt cattactatt agaaataact ctaaccatgt ttttacgcgt     60
accgcaatct attccaaata tgccgcagtc cagtggagcc cggaaccgca gctgagcatt    120
agcccaggta atgggaccct gttcatcctg aaagacatcc tgagcatccg cggtacgtcc    180
ggctacgtgc agtaccgtgt cggcgacggt ccgggctggg tgcgtgttac ctttagcagc    240
ctggtgggtg cggacgaagt tgctgagtgg agcagcggtg atctgccgga tggctttgtt    300
ctgcaaaagc ctgtccgcac cggtagccgt ccgctgcaag cgacgttcga ggcgaccaag    360
caacatcacc accaccacca ctaa                                          384
```

```
<210> SEQ ID NO 26
<211> LENGTH: 127
<212> TYPE: PRT
```

<213> ORGANISM: Artificial Sequence
<220> FEATURE:
<223> OTHER INFORMATION: Modified protein from Mattirolomyces
      terfezioides with optional His-Tag
<220> FEATURE:
<221> NAME/KEY: misc_feature
<222> LOCATION: (122)..(127)
<223> OTHER INFORMATION: Absent or Histidine

<400> SEQUENCE: 26

Met Pro Asp Leu Ser Ser Phe Ile Thr Ile Arg Asn Asn Ser Asn His
1               5                   10                  15

Val Phe Thr Arg Thr Ala Ile Tyr Ser Lys Tyr Ala Ala Val Gln Trp
            20                  25                  30

Ser Pro Glu Pro Gln Leu Ser Ile Ser Pro Gly Lys Trp Asp Leu Phe
        35                  40                  45

Ile Leu Lys Asp Ile Leu Ser Ile Arg Gly Thr Ser Gly Tyr Val Gln
    50                  55                  60

Tyr Arg Val Gly Asp Gly Pro Gly Trp Val Arg Val Thr Phe Ser Ser
65                  70                  75                  80

Leu Val Gly Ala Asp Glu Val Ala Glu Trp Ser Ser Gly Asp Leu Pro
                85                  90                  95

Asp Gly Phe Val Leu Gln Lys Pro Val Arg Thr Gly Ser Arg Pro Leu
            100                 105                 110

Gln Ala Thr Phe Glu Ala Thr Lys Gln Xaa Xaa Xaa Xaa Xaa Xaa
        115                 120                 125

<210> SEQ ID NO 27
<211> LENGTH: 384
<212> TYPE: DNA
<213> ORGANISM: Artificial Sequence
<220> FEATURE:
<223> OTHER INFORMATION: Coding Sequence of modified protein from
      Mattirolomyces terfezioides with His-Tag

<400> SEQUENCE: 27
atgccggatt tgagctcgtt cattactatt aagaataact ctaaccatgt ttttacgaaa      60
accgcaatct attccaaata tgccgcagtc cagtggagcc cggaaccgca gctgagcatt     120
agcccaggta atgggaccct gttcatcctg aaagacatcc tgagcatccg cggtacgtcc     180
ggctacgtgc agtaccgtgt cggcgacggt ccgggctggg tgcgtgttac ctttagcagc     240
ctggtgggtg cggacgaagt tgctgagtgg agcagcggtg atctgccgga tggctttgtt     300
ctgcaaaagc ctgtccgcac cggtagccgt ccgctgcaag cgacgttcga ggcgaccaag     360
caacatcacc accaccacca ctaa                                             384

<210> SEQ ID NO 28
<211> LENGTH: 127
<212> TYPE: PRT
<213> ORGANISM: Artificial Sequence
<220> FEATURE:
<223> OTHER INFORMATION: Modified protein from Mattirolomyces
      terfezioides with optional His-Tag
<220> FEATURE:
<221> NAME/KEY: misc_feature
<222> LOCATION: (122)..(127)
<223> OTHER INFORMATION: Absent or Histidine

<400> SEQUENCE: 28

Met Pro Asp Leu Ser Ser Phe Ile Thr Ile Lys Asn Asn Ser Asn His
1               5                   10                  15

Val Phe Thr Lys Thr Ala Ile Tyr Ser Lys Tyr Ala Ala Val Gln Trp

```
            20                  25                  30

Ser Pro Glu Pro Gln Leu Ser Ile Ser Pro Gly Lys Trp Asp Leu Phe
            35                  40                  45

Ile Leu Lys Asp Ile Leu Ser Ile Arg Gly Thr Ser Gly Tyr Val Gln
        50                  55                  60

Tyr Arg Val Gly Asp Gly Pro Gly Trp Val Arg Val Thr Phe Ser Ser
65                  70                  75                  80

Leu Val Gly Ala Asp Glu Val Ala Glu Trp Ser Ser Gly Asp Leu Pro
                85                  90                  95

Asp Gly Phe Val Leu Gln Lys Pro Val Arg Thr Gly Ser Arg Pro Leu
            100                 105                 110

Gln Ala Thr Phe Glu Ala Thr Lys Gln Xaa Xaa Xaa Xaa Xaa Xaa
            115                 120                 125
```

<210> SEQ ID NO 29
<211> LENGTH: 384
<212> TYPE: DNA
<213> ORGANISM: Artificial Sequence
<220> FEATURE:
<223> OTHER INFORMATION: Coding Sequence of modified protein from
      Mattirolomyces terfezioides with His-Tag

<400> SEQUENCE: 29

```
atgccggatt tgagctcgtt cattactatt aagaataact ctaaccatgt ttttacgcgt    60
accgcaatct attcccgcta tgccgcagtc cagtggagcc cggaaccgca gctgagcatt   120
agcccaggta atgggaccct gttcatcctg aaagacatcc tgagcatccg cggtacgtcc   180
ggctacgtgc agtaccgtgt cggcgacggt ccgggctggg tgcgtgttac ctttagcagc   240
ctggtgggtg cggacgaagt tgctgagtgg agcagcggtg atctgccgga tggctttgtt   300
ctgcaaaagc ctgtccgcac cggtagccgt ccgctgcaag cgacgttcga ggcgaccaag   360
caacatcacc accaccacca ctaa                                         384
```

<210> SEQ ID NO 30
<211> LENGTH: 127
<212> TYPE: PRT
<213> ORGANISM: Artificial Sequence
<220> FEATURE:
<223> OTHER INFORMATION: Modified protein from Mattirolomyces
      terfezioides with optional His-Tag
<220> FEATURE:
<221> NAME/KEY: misc_feature
<222> LOCATION: (122)..(127)
<223> OTHER INFORMATION: Absent or Histidine

<400> SEQUENCE: 30

```
Met Pro Asp Leu Ser Ser Phe Ile Thr Ile Lys Asn Asn Ser Asn His
1               5                   10                  15

Val Phe Thr Arg Thr Ala Ile Tyr Ser Arg Tyr Ala Ala Val Gln Trp
            20                  25                  30

Ser Pro Glu Pro Gln Leu Ser Ile Ser Pro Gly Lys Trp Asp Leu Phe
            35                  40                  45

Ile Leu Lys Asp Ile Leu Ser Ile Arg Gly Thr Ser Gly Tyr Val Gln
        50                  55                  60

Tyr Arg Val Gly Asp Gly Pro Gly Trp Val Arg Val Thr Phe Ser Ser
65                  70                  75                  80

Leu Val Gly Ala Asp Glu Val Ala Glu Trp Ser Ser Gly Asp Leu Pro
                85                  90                  95

Asp Gly Phe Val Leu Gln Lys Pro Val Arg Thr Gly Ser Arg Pro Leu
```

```
                100               105               110
Gln Ala Thr Phe Glu Ala Thr Lys Gln Xaa Xaa Xaa Xaa Xaa
        115               120               125

<210> SEQ ID NO 31
<211> LENGTH: 384
<212> TYPE: DNA
<213> ORGANISM: Artificial Sequence
<220> FEATURE:
<223> OTHER INFORMATION: Coding Sequence of modified protein from
      Mattirolomyces terfezioides with His-Tag

<400> SEQUENCE: 31
atgccggatt tgagctcgtt cattactatt aagaataact ctaaccatgt ttttacgcgt     60
accgcaatct attccaaata tgccgcagtc cagtggagcc cggatccgca gctgagcatt   120
agcccaggta atgggacct  gttcatcctg aaagacatcc tgagcatccg cggtacgtcc   180
ggctacgtgc agtaccgtgt cggcgacggt ccgggctggg tcgtgttac  ctttagcagc   240 ctggtgggtg cggacgaagt tgctgagtgg agcagcggtg atctgccgga tggctttgtt   300
ctgcaaaagc ctgtccgcac cggtagccgt ccgctgcaag cgacgttcga ggcgaccaag   360
caacatcacc accaccacca ctaa                                          384

<210> SEQ ID NO 32
<211> LENGTH: 127
<212> TYPE: PRT
<213> ORGANISM: Artificial Sequence
<220> FEATURE:
<223> OTHER INFORMATION: Modified protein from Mattirolomyces
      terfezioides with optional His-Tag
<220> FEATURE:
<221> NAME/KEY: misc_feature
<222> LOCATION: (122)..(127)
<223> OTHER INFORMATION: Absent or Histidine

<400> SEQUENCE: 32

Met Pro Asp Leu Ser Ser Phe Ile Thr Ile Lys Asn Asn Ser Asn His
1               5                   10                  15

Val Phe Thr Arg Thr Ala Ile Tyr Ser Lys Tyr Ala Ala Val Gln Trp
            20                  25                  30

Ser Pro Asp Pro Gln Leu Ser Ile Ser Pro Gly Lys Trp Asp Leu Phe
        35                  40                  45

Ile Leu Lys Asp Ile Leu Ser Ile Arg Gly Thr Ser Gly Tyr Val Gln
    50                  55                  60

Tyr Arg Val Gly Asp Gly Pro Gly Trp Val Arg Val Thr Phe Ser Ser
65                  70                  75                  80

Leu Val Gly Ala Asp Glu Val Ala Glu Trp Ser Ser Gly Asp Leu Pro
                85                  90                  95

Asp Gly Phe Val Leu Gln Lys Pro Val Arg Thr Gly Ser Arg Pro Leu
            100                 105                 110

Gln Ala Thr Phe Glu Ala Thr Lys Gln Xaa Xaa Xaa Xaa Xaa
        115                 120                 125

<210> SEQ ID NO 33
<211> LENGTH: 384
<212> TYPE: DNA
<213> ORGANISM: Artificial Sequence
<220> FEATURE:
<223> OTHER INFORMATION: Coding Sequence of modified protein from
      Mattirolomyces terfezioides with His-Tag

<400> SEQUENCE: 33
```

```
atgccggatt tgagctcgtt cattactatt aagaataact ctaaccatgt ttttacgcgt    60
accgcaatct attccaaata tgccgcagtc cagtggagcc cggaaccgca gctgagcatt   120
agcccaggtc gctgggacct gttcatcctg aaagacatcc tgagcatccg cggtacgtcc   180
ggctacgtgc agtaccgtgt cggcgacggt ccgggctggg tgcgtgttac ctttagcagc   240
ctggtgggtg cggacgaagt tgctgagtgg agcagcggtg atctgccgga tggctttgtt   300
ctgcaaaagc ctgtccgcac cggtagccgt ccgctgcaag cgacgttcga ggcgaccaag   360
caacatcacc accaccacca ctaa                                           384
```

<210> SEQ ID NO 34
<211> LENGTH: 127
<212> TYPE: PRT
<213> ORGANISM: Artificial Sequence
<220> FEATURE:
<223> OTHER INFORMATION: Modified protein from Mattirolomyces
      terfezioides with optional His-Tag
<220> FEATURE:
<221> NAME/KEY: misc_feature
<222> LOCATION: (122)..(127)
<223> OTHER INFORMATION: Absent or Histidine

<400> SEQUENCE: 34

```
Met Pro Asp Leu Ser Ser Phe Ile Thr Ile Lys Asn Asn Ser Asn His
1               5                   10                  15

Val Phe Thr Arg Thr Ala Ile Tyr Ser Lys Tyr Ala Ala Val Gln Trp
            20                  25                  30

Ser Pro Glu Pro Gln Leu Ser Ile Ser Pro Gly Arg Trp Asp Leu Phe
        35                  40                  45

Ile Leu Lys Asp Ile Leu Ser Ile Arg Gly Thr Ser Gly Tyr Val Gln
    50                  55                  60

Tyr Arg Val Gly Asp Gly Pro Gly Trp Val Arg Val Thr Phe Ser Ser
65                  70                  75                  80

Leu Val Gly Ala Asp Glu Val Ala Glu Trp Ser Ser Gly Asp Leu Pro
                85                  90                  95

Asp Gly Phe Val Leu Gln Lys Pro Val Arg Thr Gly Ser Arg Pro Leu
            100                 105                 110

Gln Ala Thr Phe Glu Ala Thr Lys Gln Xaa Xaa Xaa Xaa Xaa Xaa
        115                 120                 125
```

<210> SEQ ID NO 35
<211> LENGTH: 384
<212> TYPE: DNA
<213> ORGANISM: Artificial Sequence
<220> FEATURE:
<223> OTHER INFORMATION: Coding Sequence of modified protein from
      Mattirolomyces terfezioides with His-Tag

<400> SEQUENCE: 35

```
atgccggatt tgagctcgtt cattactatt aagaataact ctaaccatgt ttttacgcgt    60
accgcaatct attccaaata tgccgcagtc cagtggagcc cggaaccgca gctgagcatt   120
agcccaggta atgggaact gttcatcctg aaagacatcc tgagcatccg cggtacgtcc   180
ggctacgtgc agtaccgtgt cggcgacggt ccgggctggg tgcgtgttac ctttagcagc   240
ctggtgggtg cggacgaagt tgctgagtgg agcagcggtg atctgccgga tggctttgtt   300
ctgcaaaagc ctgtccgcac cggtagccgt ccgctgcaag cgacgttcga ggcgaccaag   360
caacatcacc accaccacca ctaa                                           384
```

<210> SEQ ID NO 36
<211> LENGTH: 127
<212> TYPE: PRT
<213> ORGANISM: Artificial Sequence
<220> FEATURE:
<223> OTHER INFORMATION: Modified protein from Mattirolomyces
    terfezioides with optional His-Tag
<220> FEATURE:
<221> NAME/KEY: misc_feature
<222> LOCATION: (122)..(127)
<223> OTHER INFORMATION: Absent or Histidine

<400> SEQUENCE: 36

```
Met Pro Asp Leu Ser Ser Phe Ile Thr Ile Lys Asn Asn Ser Asn His
1               5                   10                  15

Val Phe Thr Arg Thr Ala Ile Tyr Ser Lys Tyr Ala Ala Val Gln Trp
            20                  25                  30

Ser Pro Glu Pro Gln Leu Ser Ile Ser Pro Gly Lys Trp Glu Leu Phe
        35                  40                  45

Ile Leu Lys Asp Ile Leu Ser Ile Arg Gly Thr Ser Gly Tyr Val Gln
    50                  55                  60

Tyr Arg Val Gly Asp Gly Pro Gly Trp Val Arg Val Thr Phe Ser Ser
65                  70                  75                  80

Leu Val Gly Ala Asp Glu Val Ala Glu Trp Ser Ser Gly Asp Leu Pro
                85                  90                  95

Asp Gly Phe Val Leu Gln Lys Pro Val Arg Thr Gly Ser Arg Pro Leu
            100                 105                 110

Gln Ala Thr Phe Glu Ala Thr Lys Gln Xaa Xaa Xaa Xaa Xaa Xaa
        115                 120                 125
```

<210> SEQ ID NO 37
<211> LENGTH: 384
<212> TYPE: DNA
<213> ORGANISM: Artificial Sequence
<220> FEATURE:
<223> OTHER INFORMATION: Coding Sequence of modified protein from
    Mattirolomyces terfezioides with His-Tag

<400> SEQUENCE: 37

```
atgccggatt tgagctcgtt cattactatt aagaataact ctaaccatgt ttttacgcgt    60
accgcaatct attccaaata tgccgcagtc cagtggagcc cggaaccgca gctgagcatt   120
agcccaggta atgggaccct gttcatcctg cgcgacatcc tgagcatccg cggtacgtcc   180
ggctacgtgc agtaccgtgt cggcgacggt ccgggctggg tgcgtgttac ctttagcagc   240
ctggtgggtg cggacgaagt tgctgagtgg agcagcggtg atctgccgga tggctttgtt   300
ctgcaaaagc ctgtccgcac cggtagccgt ccgctgcaag cgacgttcga ggcgaccaag   360
caacatcacc accaccacca ctaa                                          384
```

<210> SEQ ID NO 38
<211> LENGTH: 127
<212> TYPE: PRT
<213> ORGANISM: Artificial Sequence
<220> FEATURE:
<223> OTHER INFORMATION: Modified protein from Mattirolomyces
    terfezioides with optional His-Tag
<220> FEATURE:
<221> NAME/KEY: misc_feature
<222> LOCATION: (122)..(127)
<223> OTHER INFORMATION: Absent or Histidine

<400> SEQUENCE: 38

Met Pro Asp Leu Ser Ser Phe Ile Thr Ile Lys Asn Asn Ser Asn His
1               5                   10                  15

Val Phe Thr Arg Thr Ala Ile Tyr Ser Lys Tyr Ala Ala Val Gln Trp
                20                  25                  30

Ser Pro Glu Pro Gln Leu Ser Ile Ser Pro Gly Lys Trp Asp Leu Phe
            35                  40                  45

Ile Leu Arg Asp Ile Leu Ser Ile Arg Gly Thr Ser Gly Tyr Val Gln
    50                  55                  60

Tyr Arg Val Gly Asp Gly Pro Gly Trp Val Arg Val Thr Phe Ser Ser
65                  70                  75                  80

Leu Val Gly Ala Asp Glu Val Ala Glu Trp Ser Ser Gly Asp Leu Pro
                85                  90                  95

Asp Gly Phe Val Leu Gln Lys Pro Val Arg Thr Gly Ser Arg Pro Leu
            100                 105                 110

Gln Ala Thr Phe Glu Ala Thr Lys Gln Xaa Xaa Xaa Xaa Xaa
            115                 120                 125

<210> SEQ ID NO 39
<211> LENGTH: 384
<212> TYPE: DNA
<213> ORGANISM: Artificial Sequence
<220> FEATURE:
<223> OTHER INFORMATION: Coding Sequence of modified protein from
      Mattirolomyces terfezioides with His-Tag

<400> SEQUENCE: 39
atgccggatt tgagctcgtt cattactatt aagaataact ctaaccatgt ttttacgcgt      60
accgcaatct attccaaata tgccgcagtc cagtggagcc cggaaccgca gctgagcatt     120
agcccaggta atgggacctg ttcatcctga aagaaatcc tgagcatccg cggtacgtcc      180
ggctacgtgc agtaccgtgt cggcgacggt ccgggctggg tgcgtgttac ctttagcagc     240
ctggtgggtg cggacgaagt tgctgagtgg agcagcggtg atctgccgga tggctttgtt     300
ctgcaaaagc ctgtccgcac cggtagccgt ccgctgcaag cgacgttcga ggcgaccaag     360
caacatcacc accaccacca ctaa                                            384

<210> SEQ ID NO 40
<211> LENGTH: 127
<212> TYPE: PRT
<213> ORGANISM: Artificial Sequence
<220> FEATURE:
<223> OTHER INFORMATION: Modified protein from Mattirolomyces
      terfezioides with optional His-Tag
<220> FEATURE:
<221> NAME/KEY: misc_feature
<222> LOCATION: (122)..(127)
<223> OTHER INFORMATION: Absent or Histidine

<400> SEQUENCE: 40

Met Pro Asp Leu Ser Ser Phe Ile Thr Ile Lys Asn Asn Ser Asn His
1               5                   10                  15

Val Phe Thr Arg Thr Ala Ile Tyr Ser Lys Tyr Ala Ala Val Gln Trp
                20                  25                  30

Ser Pro Glu Pro Gln Leu Ser Ile Ser Pro Gly Lys Trp Asp Leu Phe
            35                  40                  45

Ile Leu Lys Glu Ile Leu Ser Ile Arg Gly Thr Ser Gly Tyr Val Gln
    50                  55                  60

Tyr Arg Val Gly Asp Gly Pro Gly Trp Val Arg Val Thr Phe Ser Ser
65                  70                  75                  80

```
Leu Val Gly Ala Asp Glu Val Ala Glu Trp Ser Ser Gly Asp Leu Pro
            85                  90                  95

Asp Gly Phe Val Leu Gln Lys Pro Val Arg Thr Gly Ser Arg Pro Leu
        100                 105                 110

Gln Ala Thr Phe Glu Ala Thr Lys Gln Xaa Xaa Xaa Xaa Xaa Xaa
    115                 120                 125
```

<210> SEQ ID NO 41
<211> LENGTH: 384
<212> TYPE: DNA
<213> ORGANISM: Artificial Sequence
<220> FEATURE:
<223> OTHER INFORMATION: Coding Sequence of modified protein from
      Mattirolomyces terfezioides with His-Tag

<400> SEQUENCE: 41

```
atgccggatt tgagctcgtt cattactatt aagaataact ctaaccatgt ttttacgcgt     60
accgcaatct attccaaata tgccgcagtc cagtggagcc cggaaccgca gctgagcatt    120
agcccaggta atgggacct gttcatcctg aaagacatcc tgagcatcaa aggtacgtcc    180
ggctacgtgc agtaccgtgt cggcgacggt ccgggctggg tgcgtgttac ctttagcagc    240
ctggtgggtg cggacgaagt tgctgagtgg agcagcggtg atctgccgga tggctttgtt    300
ctgcaaaagc ctgtccgcac cggtagccgt ccgctgcaag cgacgttcga ggcgaccaag    360
caacatcacc accaccacca ctaa                                           384
```

<210> SEQ ID NO 42
<211> LENGTH: 127
<212> TYPE: PRT
<213> ORGANISM: Artificial Sequence
<220> FEATURE:
<223> OTHER INFORMATION: Modified protein from Mattirolomyces
      terfezioides with optional His-Tag
<220> FEATURE:
<221> NAME/KEY: misc_feature
<222> LOCATION: (122)..(127)
<223> OTHER INFORMATION: Absent or Histidine

<400> SEQUENCE: 42

```
Met Pro Asp Leu Ser Ser Phe Ile Thr Ile Lys Asn Asn Ser Asn His
1               5                   10                  15

Val Phe Thr Arg Thr Ala Ile Tyr Ser Lys Tyr Ala Ala Val Gln Trp
            20                  25                  30

Ser Pro Glu Pro Gln Leu Ser Ile Ser Pro Gly Lys Trp Asp Leu Phe
        35                  40                  45

Ile Leu Lys Asp Ile Leu Ser Ile Lys Gly Thr Ser Gly Tyr Val Gln
    50                  55                  60

Tyr Arg Val Gly Asp Gly Pro Gly Trp Val Arg Val Thr Phe Ser Ser
65                  70                  75                  80

Leu Val Gly Ala Asp Glu Val Ala Glu Trp Ser Ser Gly Asp Leu Pro
            85                  90                  95

Asp Gly Phe Val Leu Gln Lys Pro Val Arg Thr Gly Ser Arg Pro Leu
        100                 105                 110

Gln Ala Thr Phe Glu Ala Thr Lys Gln Xaa Xaa Xaa Xaa Xaa Xaa
    115                 120                 125
```

<210> SEQ ID NO 43
<211> LENGTH: 384
<212> TYPE: DNA
<213> ORGANISM: Artificial Sequence
<220> FEATURE:

<223> OTHER INFORMATION: Coding Sequence of modified protein from
Mattirolomyces terfezioides with His-Tag

<400> SEQUENCE: 43

| | |
|---|---|
| atgccggatt tgagctcgtt cattactatt aagaataact ctaaccatgt ttttacgcgt | 60 |
| accgcaatct attccaaata tgccgcagtc cagtggagcc cggaaccgca gctgagcatt | 120 |
| agcccaggta atgggacct gttcatcctg aaagacatcc tgagcatccg cggtacgtcc | 180 |
| ggctacgtgc agtacaaagt cggcgacggt ccgggctggg tgcgtgttac ctttagcagc | 240 |
| ctggtgggtg cggacgaagt tgctgagtgg agcagcggtg atctgccgga tggctttgtt | 300 |
| ctgcaaaagc ctgtccgcac cggtagccgt ccgctgcaag cgacgttcga ggcgaccaag | 360 |
| caacatcacc accaccacca ctaa | 384 |

<210> SEQ ID NO 44
<211> LENGTH: 127
<212> TYPE: PRT
<213> ORGANISM: Artificial Sequence
<220> FEATURE:
<223> OTHER INFORMATION: Modified protein from Mattirolomyces
terfezioides with optional His-Tag
<220> FEATURE:
<221> NAME/KEY: misc_feature
<222> LOCATION: (122)..(127)
<223> OTHER INFORMATION: Absent or Histidine

<400> SEQUENCE: 44

Met Pro Asp Leu Ser Ser Phe Ile Thr Ile Lys Asn Asn Ser Asn His
1               5                   10                  15

Val Phe Thr Arg Thr Ala Ile Tyr Ser Lys Tyr Ala Ala Val Gln Trp
            20                  25                  30

Ser Pro Glu Pro Gln Leu Ser Ile Ser Pro Gly Lys Trp Asp Leu Phe
        35                  40                  45

Ile Leu Lys Asp Ile Leu Ser Ile Arg Gly Thr Ser Gly Tyr Val Gln
    50                  55                  60

Tyr Lys Val Gly Asp Gly Pro Gly Trp Val Arg Val Thr Phe Ser Ser
65                  70                  75                  80

Leu Val Gly Ala Asp Glu Val Ala Glu Trp Ser Ser Gly Asp Leu Pro
                85                  90                  95

Asp Gly Phe Val Leu Gln Lys Pro Val Arg Thr Gly Ser Arg Pro Leu
            100                 105                 110

Gln Ala Thr Phe Glu Ala Thr Lys Gln Xaa Xaa Xaa Xaa Xaa Xaa
        115                 120                 125

<210> SEQ ID NO 45
<211> LENGTH: 384
<212> TYPE: DNA
<213> ORGANISM: Artificial Sequence
<220> FEATURE:
<223> OTHER INFORMATION: Coding Sequence of modified protein from
Mattirolomyces terfezioides with His-Tag

<400> SEQUENCE: 45

| | |
|---|---|
| atgccggatt tgagctcgtt cattactatt aagaataact ctaaccatgt ttttacgcgt | 60 |
| accgcaatct attccaaata tgccgcagtc cagtggagcc cggaaccgca gctgagcatt | 120 |
| agcccaggta atgggacct gttcatcctg aaagacatcc tgagcatccg cggtacgtcc | 180 |
| ggctacgtgc agtaccgtgt cggcgagggt ccgggctggg tgcgtgttac ctttagcagc | 240 |
| ctggtgggtg cggacgaagt tgctgagtgg agcagcggtg atctgccgga tggctttgtt | 300 |

```
ctgcaaaagc tgtccgcac cggtagccgt ccgctgcaag cgacgttcga ggcgaccaag    360
caacatcacc accaccacca ctaa                                          384
```

```
<210> SEQ ID NO 46
<211> LENGTH: 127
<212> TYPE: PRT
<213> ORGANISM: Artificial Sequence
<220> FEATURE:
<223> OTHER INFORMATION: Modified protein from Mattirolomyces
      terfezioides with optional His-Tag
<220> FEATURE:
<221> NAME/KEY: misc_feature
<222> LOCATION: (122)..(127)
<223> OTHER INFORMATION: Absent or Histidine

<400> SEQUENCE: 46
```

Met Pro Asp Leu Ser Ser Phe Ile Thr Ile Lys Asn Asn Ser Asn His
1               5                   10                  15

Val Phe Thr Arg Thr Ala Ile Tyr Ser Lys Tyr Ala Ala Val Gln Trp
            20                  25                  30

Ser Pro Glu Pro Gln Leu Ser Ile Ser Pro Gly Lys Trp Asp Leu Phe
        35                  40                  45

Ile Leu Lys Asp Ile Leu Ser Ile Arg Gly Thr Ser Gly Tyr Val Gln
    50                  55                  60

Tyr Arg Val Gly Glu Gly Pro Gly Trp Val Arg Val Thr Phe Ser Ser
65                  70                  75                  80

Leu Val Gly Ala Asp Glu Val Ala Glu Trp Ser Ser Gly Asp Leu Pro
                85                  90                  95

Asp Gly Phe Val Leu Gln Lys Pro Val Arg Thr Gly Ser Arg Pro Leu
            100                 105                 110

Gln Ala Thr Phe Glu Ala Thr Lys Gln Xaa Xaa Xaa Xaa Xaa Xaa
        115                 120                 125

```
<210> SEQ ID NO 47
<211> LENGTH: 384
<212> TYPE: DNA
<213> ORGANISM: Artificial Sequence
<220> FEATURE:
<223> OTHER INFORMATION: Coding Sequence of modified protein from
      Mattirolomyces terfezioides with His-Tag

<400> SEQUENCE: 47
atgccggatt tgagctcgtt cattactatt aagaataact ctaaccatgt ttttacgcgt    60
accgcaatct attccaaata tgccgcagtc cagtggagcc cggaaccgca gctgagcatt   120
agcccaggta atgggaccct gttcatcctg aaagacatcc tgagcatccg cggtacgtcc   180
ggctacgtgc agtaccgtgt cggcgacggt ccgggctggg tgaaagttac ctttagcagc   240
ctggtgggtg cggacgaagt tgctgagtgg agcagcggtg atctgccgga tggctttgtt   300
ctgcaaaagc tgtccgcac cggtagccgt ccgctgcaag cgacgttcga ggcgaccaag    360
caacatcacc accaccacca ctaa                                          384
```

```
<210> SEQ ID NO 48
<211> LENGTH: 127
<212> TYPE: PRT
<213> ORGANISM: Artificial Sequence
<220> FEATURE:
<223> OTHER INFORMATION: Modified protein from Mattirolomyces
      terfezioides with optional His-Tag
<220> FEATURE:
<221> NAME/KEY: misc_feature
<222> LOCATION: (122)..(127)
```

<223> OTHER INFORMATION: Absent or Histidine

<400> SEQUENCE: 48

Met Pro Asp Leu Ser Ser Phe Ile Thr Ile Lys Asn Asn Ser Asn His
1               5                   10                  15

Val Phe Thr Arg Thr Ala Ile Tyr Ser Lys Tyr Ala Ala Val Gln Trp
            20                  25                  30

Ser Pro Glu Pro Gln Leu Ser Ile Ser Pro Gly Lys Trp Asp Leu Phe
        35                  40                  45

Ile Leu Lys Asp Ile Leu Ser Ile Arg Gly Thr Ser Gly Tyr Val Gln
    50                  55                  60

Tyr Arg Val Gly Asp Gly Pro Gly Trp Val Lys Val Thr Phe Ser Ser
65                  70                  75                  80

Leu Val Gly Ala Asp Glu Val Ala Glu Trp Ser Ser Gly Asp Leu Pro
                85                  90                  95

Asp Gly Phe Val Leu Gln Lys Pro Val Arg Thr Gly Ser Arg Pro Leu
            100                 105                 110

Gln Ala Thr Phe Glu Ala Thr Lys Gln Xaa Xaa Xaa Xaa Xaa
        115                 120                 125

<210> SEQ ID NO 49
<211> LENGTH: 384
<212> TYPE: DNA
<213> ORGANISM: Artificial Sequence
<220> FEATURE:
<223> OTHER INFORMATION: Coding Sequence of modified protein from
      Mattirolomyces terfezioides with His-Tag

<400> SEQUENCE: 49
atgccggatt tgagctcgtt cattactatt aagaataact ctaaccatgt ttttacgcgt      60
accgcaatct attccaaata tgccgcagtc cagtggagcc cggaaccgca gctgagcatt     120
agcccaggta atgggacct gttcatcctg aaagacatcc tgagcatccg cggtacgtcc     180
ggctacgtgc agtaccgtgt cggcgacggt ccgggctggg tgcgtgttac ctttagcagc     240
ctggtgggtg cggaagaagt tgctgagtgg agcagcggtg atctgccgga tggctttgtt     300
ctgcaaaagc ctgtccgcac cggtagccgt ccgctgcaag cgacgttcga ggcgaccaag     360
caacatcacc accaccacca ctaa                                            384

<210> SEQ ID NO 50
<211> LENGTH: 127
<212> TYPE: PRT
<213> ORGANISM: Artificial Sequence
<220> FEATURE:
<223> OTHER INFORMATION: Modified protein from Mattirolomyces
      terfezioides with optional His-Tag
<220> FEATURE:
<221> NAME/KEY: misc_feature
<222> LOCATION: (122)..(127)
<223> OTHER INFORMATION: Absent or Histidine

<400> SEQUENCE: 50

Met Pro Asp Leu Ser Ser Phe Ile Thr Ile Lys Asn Asn Ser Asn His
1               5                   10                  15

Val Phe Thr Arg Thr Ala Ile Tyr Ser Lys Tyr Ala Ala Val Gln Trp
            20                  25                  30

Ser Pro Glu Pro Gln Leu Ser Ile Ser Pro Gly Lys Trp Asp Leu Phe
        35                  40                  45

Ile Leu Lys Asp Ile Leu Ser Ile Arg Gly Thr Ser Gly Tyr Val Gln
    50                  55                  60

Tyr Arg Val Gly Asp Gly Pro Gly Trp Val Arg Val Thr Phe Ser Ser
65                  70                  75                  80

Leu Val Gly Ala Glu Glu Val Ala Glu Trp Ser Ser Gly Asp Leu Pro
                85                  90                  95

Asp Gly Phe Val Leu Gln Lys Pro Val Arg Thr Gly Ser Arg Pro Leu
            100                 105                 110

Gln Ala Thr Phe Glu Ala Thr Lys Gln Xaa Xaa Xaa Xaa Xaa Xaa
        115                 120                 125

<210> SEQ ID NO 51
<211> LENGTH: 384
<212> TYPE: DNA
<213> ORGANISM: Artificial Sequence
<220> FEATURE:
<223> OTHER INFORMATION: Coding Sequence of modified protein from
      Mattirolomyces terfezioides with His-Tag

<400> SEQUENCE: 51
atgccggatt tgagctcgtt cattactatt aagaataact ctaaccatgt ttttacgcgt      60
accgcaatct attccaaata tgccgcagtc cagtggagcc cggaaccgca gctgagcatt     120
agcccaggta atgggaccct gttcatcctg aaagacatcc tgagcatccg cggtacgtcc     180
ggctacgtgc agtaccgtgt cggcgacggt ccgggctggg tgcgtgttac ctttagcagc     240
ctggtgggtg cggacgatgt tgctgagtgg agcagcggtg atctgccgga tggctttgtt     300
ctgcaaaagc ctgtccgcac cggtagccgt ccgctgcaag cgacgttcga ggcgaccaag     360
caacatcacc accaccacca ctaa                                             384

<210> SEQ ID NO 52
<211> LENGTH: 127
<212> TYPE: PRT
<213> ORGANISM: Artificial Sequence
<220> FEATURE:
<223> OTHER INFORMATION: Modified protein from Mattirolomyces
      terfezioides with optional His-Tag
<220> FEATURE:
<221> NAME/KEY: misc_feature
<222> LOCATION: (122)..(127)
<223> OTHER INFORMATION: Absent or Histidine

<400> SEQUENCE: 52

Met Pro Asp Leu Ser Ser Phe Ile Thr Ile Lys Asn Asn Ser Asn His
1               5                   10                  15

Val Phe Thr Arg Thr Ala Ile Tyr Ser Lys Tyr Ala Ala Val Gln Trp
                20                  25                  30

Ser Pro Glu Pro Gln Leu Ser Ile Ser Pro Gly Lys Trp Asp Leu Phe
            35                  40                  45

Ile Leu Lys Asp Ile Leu Ser Ile Arg Gly Thr Ser Gly Tyr Val Gln
        50                  55                  60

Tyr Arg Val Gly Asp Gly Pro Gly Trp Val Arg Val Thr Phe Ser Ser
65                  70                  75                  80

Leu Val Gly Ala Asp Asp Val Ala Glu Trp Ser Ser Gly Asp Leu Pro
                85                  90                  95

Asp Gly Phe Val Leu Gln Lys Pro Val Arg Thr Gly Ser Arg Pro Leu
            100                 105                 110

Gln Ala Thr Phe Glu Ala Thr Lys Gln Xaa Xaa Xaa Xaa Xaa Xaa
        115                 120                 125

<210> SEQ ID NO 53

<211> LENGTH: 384
<212> TYPE: DNA
<213> ORGANISM: Artificial Sequence
<220> FEATURE:
<223> OTHER INFORMATION: Coding Sequence of modified protein from
    Mattirolomyces terfezioides with His-Tag

<400> SEQUENCE: 53

```
atgccggatt tgagctcgtt cattactatt aagaataact ctaaccatgt ttttacgcgt    60
accgcaatct attccaaata tgccgcagtc cagtggagcc cggaaccgca gctgagcatt   120
agcccaggta atgggacct gttcatcctg aaagacatcc tgagcatccg cggtacgtcc    180
ggctacgtgc agtaccgtgt cggcgacggt ccgggctggg tgcgtgttac ctttagcagc   240
ctggtgggtg cggacgaagt tgctgattgg agcagcggtg atctgccgga tggctttgtt   300
ctgcaaaagc ctgtccgcac cggtagccgt ccgctgcaag cgacgttcga ggcgaccaag   360
caacatcacc accaccacca ctaa                                          384
```

<210> SEQ ID NO 54
<211> LENGTH: 127
<212> TYPE: PRT
<213> ORGANISM: Artificial Sequence
<220> FEATURE:
<223> OTHER INFORMATION: Modified protein from Mattirolomyces
    terfezioides with optional His-Tag
<220> FEATURE:
<221> NAME/KEY: misc_feature
<222> LOCATION: (122)..(127)
<223> OTHER INFORMATION: Absent or Histidine

<400> SEQUENCE: 54

```
Met Pro Asp Leu Ser Ser Phe Ile Thr Ile Lys Asn Asn Ser Asn His
1               5                   10                  15
Val Phe Thr Arg Thr Ala Ile Tyr Ser Lys Tyr Ala Ala Val Gln Trp
            20                  25                  30
Ser Pro Glu Pro Gln Leu Ser Ile Ser Pro Gly Lys Trp Asp Leu Phe
        35                  40                  45
Ile Leu Lys Asp Ile Leu Ser Ile Arg Gly Thr Ser Gly Tyr Val Gln
    50                  55                  60
Tyr Arg Val Gly Asp Gly Pro Gly Trp Val Arg Val Thr Phe Ser Ser
65                  70                  75                  80
Leu Val Gly Ala Asp Glu Val Ala Asp Trp Ser Ser Gly Asp Leu Pro
                85                  90                  95
Asp Gly Phe Val Leu Gln Lys Pro Val Arg Thr Gly Ser Arg Pro Leu
            100                 105                 110
Gln Ala Thr Phe Glu Ala Thr Lys Gln Xaa Xaa Xaa Xaa Xaa Xaa
        115                 120                 125
```

<210> SEQ ID NO 55
<211> LENGTH: 384
<212> TYPE: DNA
<213> ORGANISM: Artificial Sequence
<220> FEATURE:
<223> OTHER INFORMATION: Coding Sequence of modified protein from
    Mattirolomyces terfezioides with His-Tag

<400> SEQUENCE: 55

```
atgccggatt tgagctcgtt cattactatt aagaataact ctaaccatgt ttttacgcgt    60
accgcaatct attccaaata tgccgcagtc cagtggagcc cggaaccgca gctgagcatt   120
agcccaggta atgggacct gttcatcctg aaagacatcc tgagcatccg cggtacgtcc    180
```

```
ggctacgtgc agtaccgtgt cggcgacggt ccgggctggg tgcgtgttac ctttagcagc    240
ctggtgggtg cggacgaagt tgctgagtgg agcagcggtg agctgccgga tggctttgtt    300
ctgcaaaagc ctgtccgcac cggtagccgt ccgctgcaag cgacgttcga ggcgaccaag    360
caacatcacc accaccacca ctaa                                          384
```

```
<210> SEQ ID NO 56
<211> LENGTH: 127
<212> TYPE: PRT
<213> ORGANISM: Artificial Sequence
<220> FEATURE:
<223> OTHER INFORMATION: Modified protein from Mattirolomyces
      terfezioides with optional His-Tag
<220> FEATURE:
<221> NAME/KEY: misc_feature
<222> LOCATION: (122)..(127)
<223> OTHER INFORMATION: Absent or Histidine

<400> SEQUENCE: 56

Met Pro Asp Leu Ser Ser Phe Ile Thr Ile Lys Asn Asn Ser Asn His
1               5                   10                  15

Val Phe Thr Arg Thr Ala Ile Tyr Ser Lys Tyr Ala Ala Val Gln Trp
            20                  25                  30

Ser Pro Glu Pro Gln Leu Ser Ile Ser Pro Gly Lys Trp Asp Leu Phe
        35                  40                  45

Ile Leu Lys Asp Ile Leu Ser Ile Arg Gly Thr Ser Gly Tyr Val Gln
    50                  55                  60

Tyr Arg Val Gly Asp Gly Pro Gly Trp Val Arg Val Thr Phe Ser Ser
65                  70                  75                  80

Leu Val Gly Ala Asp Glu Val Ala Glu Trp Ser Ser Gly Glu Leu Pro
                85                  90                  95

Asp Gly Phe Val Leu Gln Lys Pro Val Arg Thr Gly Ser Arg Pro Leu
            100                 105                 110

Gln Ala Thr Phe Glu Ala Thr Lys Gln Xaa Xaa Xaa Xaa Xaa Xaa
        115                 120                 125
```

```
<210> SEQ ID NO 57
<211> LENGTH: 384
<212> TYPE: DNA
<213> ORGANISM: Artificial Sequence
<220> FEATURE:
<223> OTHER INFORMATION: Coding Sequence of modified protein from
      Mattirolomyces terfezioides with His-Tag

<400> SEQUENCE: 57
atgccggatt tgagctcgtt cattactatt aagaataact ctaaccatgt ttttacgcgt     60
accgcaatct attccaaata tgccgcagtc cagtggagcc cggaaccgca gctgagcatt    120
agcccaggta atgggacct gttcatcctg aaagacatcc tgagcatccg cggtacgtcc    180
ggctacgtgc agtaccgtgt cggcgacggt ccgggctggg tgcgtgttac ctttagcagc    240
ctggtgggtg cggacgaagt tgctgagtgg agcagcggtg atctgccgga aggctttgtt    300
ctgcaaaagc ctgtccgcac cggtagccgt ccgctgcaag cgacgttcga ggcgaccaag    360
caacatcacc accaccacca ctaa                                          384
```

```
<210> SEQ ID NO 58
<211> LENGTH: 127
<212> TYPE: PRT
<213> ORGANISM: Artificial Sequence
<220> FEATURE:
<223> OTHER INFORMATION: Modified protein from Mattirolomyces
``` terfezioides with optional His-Tag
<220> FEATURE:
<221> NAME/KEY: misc_feature
<222> LOCATION: (122)..(127)
<223> OTHER INFORMATION: Absent or Histidine

<400> SEQUENCE: 58

Met Pro Asp Leu Ser Ser Phe Ile Thr Ile Lys Asn Asn Ser Asn His
1               5                   10                  15

Val Phe Thr Arg Thr Ala Ile Tyr Ser Lys Tyr Ala Ala Val Gln Trp
            20                  25                  30

Ser Pro Glu Pro Gln Leu Ser Ile Ser Pro Gly Lys Trp Asp Leu Phe
        35                  40                  45

Ile Leu Lys Asp Ile Leu Ser Ile Arg Gly Thr Ser Gly Tyr Val Gln
    50                  55                  60

Tyr Arg Val Gly Asp Gly Pro Gly Trp Val Arg Val Thr Phe Ser Ser
65                  70                  75                  80

Leu Val Gly Ala Asp Glu Val Ala Glu Trp Ser Ser Gly Asp Leu Pro
                85                  90                  95

Glu Gly Phe Val Leu Gln Lys Pro Val Arg Thr Gly Ser Arg Pro Leu
            100                 105                 110

Gln Ala Thr Phe Glu Ala Thr Lys Gln Xaa Xaa Xaa Xaa Xaa Xaa
        115                 120                 125

<210> SEQ ID NO 59
<211> LENGTH: 384
<212> TYPE: DNA
<213> ORGANISM: Artificial Sequence
<220> FEATURE:
<223> OTHER INFORMATION: Coding Sequence of modified protein from
      Mattirolomyces terfezioides with His-Tag

<400> SEQUENCE: 59
atgccggatt tgagctcgtt cattactatt aagaataact ctaaccatgt ttttacgcgt      60
accgcaatct attccaaata tgccgcagtc cagtggagcc cggaaccgca gctgagcatt     120
agcccaggta atgggacct gttcatcctg aaagacatcc tgagcatccg cggtacgtcc      180
ggctacgtgc agtaccgtgt cggcgacggt ccgggctggg tgcgtgttac ctttagcagc     240
ctggtgggtg cggacgaagt tgctgagtgg agcagcggtg atctgccgga tggctttgtt     300
ctgcaacgcc ctgtccgcac cggtagccgt ccgctgcaag cgacgttcga ggcgaccaag     360
caacatcacc accaccacca ctaa                                            384

<210> SEQ ID NO 60
<211> LENGTH: 127
<212> TYPE: PRT
<213> ORGANISM: Artificial Sequence
<220> FEATURE:
<223> OTHER INFORMATION: Modified protein from Mattirolomyces
      terfezioides with optional His-Tag
<220> FEATURE:
<221> NAME/KEY: misc_feature
<222> LOCATION: (122)..(127)
<223> OTHER INFORMATION: Absent or Histidine

<400> SEQUENCE: 60

Met Pro Asp Leu Ser Ser Phe Ile Thr Ile Lys Asn Asn Ser Asn His
1               5                   10                  15

Val Phe Thr Arg Thr Ala Ile Tyr Ser Lys Tyr Ala Ala Val Gln Trp
            20                  25                  30

Ser Pro Glu Pro Gln Leu Ser Ile Ser Pro Gly Lys Trp Asp Leu Phe

```
                35                  40                  45
Ile Leu Lys Asp Ile Leu Ser Ile Arg Gly Thr Ser Gly Tyr Val Gln
        50                  55                  60
Tyr Arg Val Gly Asp Gly Pro Gly Trp Val Arg Val Thr Phe Ser Ser
65                  70                  75                  80
Leu Val Gly Ala Asp Glu Val Ala Glu Trp Ser Ser Gly Asp Leu Pro
                85                  90                  95
Asp Gly Phe Val Leu Gln Arg Pro Val Arg Thr Gly Ser Arg Pro Leu
            100                 105                 110
Gln Ala Thr Phe Glu Ala Thr Lys Gln Xaa Xaa Xaa Xaa Xaa Xaa
        115                 120                 125
```

<210> SEQ ID NO 61
<211> LENGTH: 384
<212> TYPE: DNA
<213> ORGANISM: Artificial Sequence
<220> FEATURE:
<223> OTHER INFORMATION: Coding Sequence of modified protein from
      Mattirolomyces terfezioides with His-Tag

<400> SEQUENCE: 61

```
atgccggatt tgagctcgtt cattactatt aagaataact ctaaccatgt ttttacgcgt      60
accgcaatct attccaaata tgccgcagtc cagtggagcc cggaaccgca gctgagcatt     120
agcccaggta atgggacct gttcatcctg aaagacatcc tgagcatccg cggtacgtcc      180
ggctacgtgc agtaccgtgt cggcgacggt ccgggctggg tgcgtgttac ctttagcagc     240
ctggtgggtg cggacgaagt tgctgagtgg agcagcggtg atctgccgga tggctttgtt     300
ctgcaaaagc ctgtcaaaac cggtagccgt ccgctgcaag cgacgttcga ggcgaccaag     360
caacatcacc accaccacca ctaa                                            384
```

<210> SEQ ID NO 62
<211> LENGTH: 127
<212> TYPE: PRT
<213> ORGANISM: Artificial Sequence
<220> FEATURE:
<223> OTHER INFORMATION: Modified protein from Mattirolomyces
      terfezioides with optional His-Tag
<220> FEATURE:
<221> NAME/KEY: misc_feature
<222> LOCATION: (122)..(127)
<223> OTHER INFORMATION: Absent or Histidine

<400> SEQUENCE: 62

```
Met Pro Asp Leu Ser Ser Phe Ile Thr Ile Lys Asn Asn Ser Asn His
1               5                   10                  15
Val Phe Thr Arg Thr Ala Ile Tyr Ser Lys Tyr Ala Ala Val Gln Trp
            20                  25                  30
Ser Pro Glu Pro Gln Leu Ser Ile Ser Pro Gly Lys Trp Asp Leu Phe
        35                  40                  45
Ile Leu Lys Asp Ile Leu Ser Ile Arg Gly Thr Ser Gly Tyr Val Gln
    50                  55                  60
Tyr Arg Val Gly Asp Gly Pro Gly Trp Val Arg Val Thr Phe Ser Ser
65                  70                  75                  80
Leu Val Gly Ala Asp Glu Val Ala Glu Trp Ser Ser Gly Asp Leu Pro
                85                  90                  95
Asp Gly Phe Val Leu Gln Lys Pro Val Lys Thr Gly Ser Arg Pro Leu
            100                 105                 110
Gln Ala Thr Phe Glu Ala Thr Lys Gln Xaa Xaa Xaa Xaa Xaa Xaa
```

<210> SEQ ID NO 63
<211> LENGTH: 384
<212> TYPE: DNA
<213> ORGANISM: Artificial Sequence
<220> FEATURE:
<223> OTHER INFORMATION: Coding Sequence of modified protein from
      Mattirolomyces terfezioides with His-Tag

<400> SEQUENCE: 63

```
atgccggatt tgagctcgtt cattactatt aagaataact ctaaccatgt ttttacgcgt    60
accgcaatct attccaaata tgccgcagtc cagtggagcc cggaaccgca gctgagcatt   120
agcccaggta atgggacct gttcatcctg aaagacatcc tgagcatccg cggtacgtcc    180
ggctacgtgc agtaccgtgt cggcgacggt ccgggctggg tcgtgttac ctttagcagc    240
ctggtgggtg cggacgaagt tgctgagtgg agcagcggtg atctgccgga tggctttgtt   300
ctgcaaaagc ctgtccgcac cggtagcaaa ccgctgcaag cgacgttcga ggcgaccaag   360
caacatcacc accaccacca ctaa                                          384
```

<210> SEQ ID NO 64
<211> LENGTH: 127
<212> TYPE: PRT
<213> ORGANISM: Artificial Sequence
<220> FEATURE:
<223> OTHER INFORMATION: Modified protein from Mattirolomyces
      terfezioides with optional His-Tag
<220> FEATURE:
<221> NAME/KEY: misc_feature
<222> LOCATION: (122)..(127)
<223> OTHER INFORMATION: Absent or Histidine

<400> SEQUENCE: 64

```
Met Pro Asp Leu Ser Ser Phe Ile Thr Ile Lys Asn Asn Ser Asn His
1               5                  10                  15

Val Phe Thr Arg Thr Ala Ile Tyr Ser Lys Tyr Ala Ala Val Gln Trp
            20                  25                  30

Ser Pro Glu Pro Gln Leu Ser Ile Ser Pro Gly Lys Trp Asp Leu Phe
        35                  40                  45

Ile Leu Lys Asp Ile Leu Ser Ile Arg Gly Thr Ser Gly Tyr Val Gln
    50                  55                  60

Tyr Arg Val Gly Asp Gly Pro Gly Trp Val Arg Val Thr Phe Ser Ser
65                  70                  75                  80

Leu Val Gly Ala Asp Glu Val Ala Glu Trp Ser Ser Gly Asp Leu Pro
                85                  90                  95

Asp Gly Phe Val Leu Gln Lys Pro Val Arg Thr Gly Ser Lys Pro Leu
            100                 105                 110

Gln Ala Thr Phe Glu Ala Thr Lys Gln Xaa Xaa Xaa Xaa Xaa Xaa
        115                 120                 125
```

<210> SEQ ID NO 65
<211> LENGTH: 384
<212> TYPE: DNA
<213> ORGANISM: Artificial Sequence
<220> FEATURE:
<223> OTHER INFORMATION: Coding Sequence of modified protein from
      Mattirolomyces terfezioides with His-Tag

<400> SEQUENCE: 65

```
atgccggatt tgagctcgtt cattactatt aagaataact ctaaccatgt ttttacgcgt    60
```

-continued

```
accgcaatct attccaaata tgccgcagtc cagtggagcc cggaaccgca gctgagcatt    120
agcccaggta aatgggacct gttcatcctg aaagacatcc tgagcatccg cggtacgtcc    180
ggctacgtgc agtaccgtgt cggcgacggt ccgggctggg tgcgtgttac ctttagcagc    240
ctggtgggtg cggacgaagt tgctgagtgg agcagcggtg atctgccgga tggctttgtt    300
ctgcaaaagc ctgtccgcac cggtagccgt ccgctgcaag cgacgttcga tgcgaccaag    360
caacatcacc accaccacca ctaa                                           384
```

```
<210> SEQ ID NO 66
<211> LENGTH: 127
<212> TYPE: PRT
<213> ORGANISM: Artificial Sequence
<220> FEATURE:
<223> OTHER INFORMATION: Modified protein from Mattirolomyces
      terfezioides with optional His-Tag
<220> FEATURE:
<221> NAME/KEY: misc_feature
<222> LOCATION: (122)..(127)
<223> OTHER INFORMATION: Absent or Histidine

<400> SEQUENCE: 66

Met Pro Asp Leu Ser Ser Phe Ile Thr Ile Lys Asn Asn Ser Asn His
1               5                   10                  15

Val Phe Thr Arg Thr Ala Ile Tyr Ser Lys Tyr Ala Ala Val Gln Trp
            20                  25                  30

Ser Pro Glu Pro Gln Leu Ser Ile Ser Pro Gly Lys Trp Asp Leu Phe
        35                  40                  45

Ile Leu Lys Asp Ile Leu Ser Ile Arg Gly Thr Ser Gly Tyr Val Gln
    50                  55                  60

Tyr Arg Val Gly Asp Gly Pro Gly Trp Val Arg Val Thr Phe Ser Ser
65                  70                  75                  80

Leu Val Gly Ala Asp Glu Val Ala Glu Trp Ser Ser Gly Asp Leu Pro
                85                  90                  95

Asp Gly Phe Val Leu Gln Lys Pro Val Arg Thr Gly Ser Arg Pro Leu
            100                 105                 110

Gln Ala Thr Phe Asp Ala Thr Lys Gln Xaa Xaa Xaa Xaa Xaa Xaa
        115                 120                 125
```

```
<210> SEQ ID NO 67
<211> LENGTH: 384
<212> TYPE: DNA
<213> ORGANISM: Artificial Sequence
<220> FEATURE:
<223> OTHER INFORMATION: Coding Sequence of modified protein from
      Mattirolomyces terfezioides with His-Tag

<400> SEQUENCE: 67
atgccggatt tgagctcgtt cattactatt aagaataact ctaaccatgt ttttacgcgt     60
accgcaatct attccaaata tgccgcagtc cagtggagcc cggaaccgca gctgagcatt    120
agcccaggta aatgggacct gttcatcctg aaagacatcc tgagcatccg cggtacgtcc    180
ggctacgtgc agtaccgtgt cggcgacggt ccgggctggg tgcgtgttac ctttagcagc    240
ctggtgggtg cggacgaagt tgctgagtgg agcagcggtg atctgccgga tggctttgtt    300
ctgcaaaagc ctgtccgcac cggtagccgt ccgctgcaag cgacgttcga ggcgacccgc    360
caacatcacc accaccacca ctaa                                           384
```

```
<210> SEQ ID NO 68
<211> LENGTH: 127
```

```
<212> TYPE: PRT
<213> ORGANISM: Artificial Sequence
<220> FEATURE:
<223> OTHER INFORMATION: Modified protein from Mattirolomyces
      terfezioides with optional His-Tag
<220> FEATURE:
<221> NAME/KEY: misc_feature
<222> LOCATION: (122)..(127)
<223> OTHER INFORMATION: Absent or Histidine

<400> SEQUENCE: 68

Met Pro Asp Leu Ser Ser Phe Ile Thr Ile Lys Asn Asn Ser Asn His
1               5                   10                  15

Val Phe Thr Arg Thr Ala Ile Tyr Ser Lys Tyr Ala Ala Val Gln Trp
            20                  25                  30

Ser Pro Glu Pro Gln Leu Ser Ile Ser Pro Gly Lys Trp Asp Leu Phe
        35                  40                  45

Ile Leu Lys Asp Ile Leu Ser Ile Arg Gly Thr Ser Gly Tyr Val Gln
    50                  55                  60

Tyr Arg Val Gly Asp Gly Pro Gly Trp Val Arg Val Thr Phe Ser Ser
65                  70                  75                  80

Leu Val Gly Ala Asp Glu Val Ala Glu Trp Ser Ser Gly Asp Leu Pro
                85                  90                  95

Asp Gly Phe Val Leu Gln Lys Pro Val Arg Thr Gly Ser Arg Pro Leu
            100                 105                 110

Gln Ala Thr Phe Glu Ala Thr Arg Gln Xaa Xaa Xaa Xaa Xaa Xaa
        115                 120                 125

<210> SEQ ID NO 69
<211> LENGTH: 5
<212> TYPE: PRT
<213> ORGANISM: Artificial Sequence
<220> FEATURE:
<223> OTHER INFORMATION: Amino Acid Linker
<220> FEATURE:
<221> NAME/KEY: REPEAT
<222> LOCATION: (1)..(5)
<223> OTHER INFORMATION: May be repeated n times, where n is any integer

<400> SEQUENCE: 69

Gly Gly Gly Gly Ser
1               5

<210> SEQ ID NO 70
<211> LENGTH: 5
<212> TYPE: PRT
<213> ORGANISM: Artificial Sequence
<220> FEATURE:
<223> OTHER INFORMATION: Amino Acid Linker
<220> FEATURE:
<221> NAME/KEY: REPEAT
<222> LOCATION: (1)..(5)
<223> OTHER INFORMATION: May be repeated n times, where n is any integer

<400> SEQUENCE: 70

Glu Ala Ala Ala Lys
1               5

<210> SEQ ID NO 71
<211> LENGTH: 121
<212> TYPE: PRT
<213> ORGANISM: Artificial Sequence
<220> FEATURE:
<223> OTHER INFORMATION: Consensus Sequence 1
<220> FEATURE:
<221> NAME/KEY: misc_feature
```

```
<222> LOCATION: (3)..(3)
<223> OTHER INFORMATION: Xaa is any amino acid
<220> FEATURE:
<221> NAME/KEY: misc_feature
<222> LOCATION: (11)..(16)
<223> OTHER INFORMATION: Xaa is any amino acid
<220> FEATURE:
<221> NAME/KEY: misc_feature
<222> LOCATION: (26)..(26)
<223> OTHER INFORMATION: Xaa is any amino acid
<220> FEATURE:
<221> NAME/KEY: misc_feature
<222> LOCATION: (33)..(34)
<223> OTHER INFORMATION: Xaa is any amino acid
<220> FEATURE:
<221> NAME/KEY: misc_feature
<222> LOCATION: (36)..(38)
<223> OTHER INFORMATION: Xaa is any amino acid
<220> FEATURE:
<221> NAME/KEY: misc_feature
<222> LOCATION: (41)..(43)
<223> OTHER INFORMATION: Xaa is any amino acid
<220> FEATURE:
<221> NAME/KEY: misc_feature
<222> LOCATION: (51)..(51)
<223> OTHER INFORMATION: Xaa is any amino acid
<220> FEATURE:
<221> NAME/KEY: misc_feature
<222> LOCATION: (57)..(57)
<223> OTHER INFORMATION: Xaa is any amino acid
<220> FEATURE:
<221> NAME/KEY: misc_feature
<222> LOCATION: (66)..(66)
<223> OTHER INFORMATION: Xaa is any amino acid
<220> FEATURE:
<221> NAME/KEY: misc_feature
<222> LOCATION: (68)..(72)
<223> OTHER INFORMATION: Xaa is any amino acid
<220> FEATURE:
<221> NAME/KEY: misc_feature
<222> LOCATION: (85)..(86)
<223> OTHER INFORMATION: Xaa is any amino acid
<220> FEATURE:
<221> NAME/KEY: misc_feature
<222> LOCATION: (89)..(89)
<223> OTHER INFORMATION: Xaa is any amino acid
<220> FEATURE:
<221> NAME/KEY: misc_feature
<222> LOCATION: (97)..(97)
<223> OTHER INFORMATION: Xaa can be any naturally occurring amino acid
<220> FEATURE:
<221> NAME/KEY: misc_feature
<222> LOCATION: (101)..(110)
<223> OTHER INFORMATION: Xaa is any amino acid
<220> FEATURE:
<221> NAME/KEY: misc_feature
<222> LOCATION: (117)..(117)
<223> OTHER INFORMATION: Xaa is any amino acid
<220> FEATURE:
<221> NAME/KEY: misc_feature
<222> LOCATION: (120)..(120)
<223> OTHER INFORMATION: Xaa is any amino acid

<400> SEQUENCE: 71

Met Pro Xaa Leu Ser Ser Phe Ile Thr Ile Xaa Xaa Xaa Xaa Xaa Xaa
 1               5                  10                  15

Val Phe Thr Arg Thr Ala Ile Tyr Ser Xaa Tyr Ala Ala Val Gln Trp
             20                  25                  30

Xaa Xaa Glu Xaa Xaa Xaa Ser Ile Xaa Xaa Xaa Lys Trp Asp Leu Phe
         35                  40                  45

Ile Leu Xaa Asp Ile Leu Ser Ile Xaa Gly Thr Ser Gly Tyr Val Gln
     50                  55                  60

Tyr Xaa Val Xaa Xaa Xaa Xaa Xaa Trp Val Arg Val Thr Phe Ser Ser
65                  70                  75                  80
```

Leu Val Gly Ala Xaa Xaa Val Ala Xaa Trp Ser Ser Gly Asp Leu Pro
                85                  90                  95

Xaa Gly Phe Val Xaa Xaa Xaa Xaa Xaa Xaa Xaa Xaa Xaa Pro Leu
                100                 105                 110

Gln Ala Thr Phe Xaa Ala Thr Xaa Gln
            115             120

<210> SEQ ID NO 72
<211> LENGTH: 121
<212> TYPE: PRT
<213> ORGANISM: Artificial Sequence
<220> FEATURE:
<223> OTHER INFORMATION: Consensus sequence 2
<220> FEATURE:
<221> NAME/KEY: misc_feature
<222> LOCATION: (3)..(3)
<223> OTHER INFORMATION: Xaa is any amino acid
<220> FEATURE:
<221> NAME/KEY: misc_feature
<222> LOCATION: (11)..(16)
<223> OTHER INFORMATION: Xaa is any amino acid
<220> FEATURE:
<221> NAME/KEY: misc_feature
<222> LOCATION: (26)..(26)
<223> OTHER INFORMATION: Xaa is any amino acid
<220> FEATURE:
<221> NAME/KEY: misc_feature
<222> LOCATION: (33)..(33)
<223> OTHER INFORMATION: Xaa is any amino acid
<220> FEATURE:
<221> NAME/KEY: misc_feature
<222> LOCATION: (37)..(38)
<223> OTHER INFORMATION: Xaa is any amino acid
<220> FEATURE:
<221> NAME/KEY: misc_feature
<222> LOCATION: (41)..(41)
<223> OTHER INFORMATION: Xaa is any amino acid
<220> FEATURE:
<221> NAME/KEY: misc_feature
<222> LOCATION: (43)..(43)
<223> OTHER INFORMATION: Xaa is any amino acid
<220> FEATURE:
<221> NAME/KEY: misc_feature
<222> LOCATION: (51)..(51)
<223> OTHER INFORMATION: Xaa is any amino acid
<220> FEATURE:
<221> NAME/KEY: misc_feature
<222> LOCATION: (57)..(57)
<223> OTHER INFORMATION: Xaa is any amino acid
<220> FEATURE:
<221> NAME/KEY: misc_feature
<222> LOCATION: (66)..(66)
<223> OTHER INFORMATION: Xaa is any amino acid
<220> FEATURE:
<221> NAME/KEY: misc_feature
<222> LOCATION: (68)..(70)
<223> OTHER INFORMATION: Xaa is any amino acid
<220> FEATURE:
<221> NAME/KEY: misc_feature
<222> LOCATION: (72)..(72)
<223> OTHER INFORMATION: Xaa is any amino acid
<220> FEATURE:
<221> NAME/KEY: misc_feature
<222> LOCATION: (85)..(86)
<223> OTHER INFORMATION: Xaa is any amino acid
<220> FEATURE:
<221> NAME/KEY: misc_feature
<222> LOCATION: (89)..(89)
<223> OTHER INFORMATION: Xaa is any amino acid
<220> FEATURE:
<221> NAME/KEY: misc_feature
<222> LOCATION: (97)..(97)
<223> OTHER INFORMATION: Xaa is any amino acid
<220> FEATURE:
<221> NAME/KEY: misc_feature

```
<222> LOCATION: (101)..(103)
<223> OTHER INFORMATION: Xaa is any amino acid
<220> FEATURE:
<221> NAME/KEY: misc_feature
<222> LOCATION: (105)..(110)
<223> OTHER INFORMATION: Xaa is any amino acid
<220> FEATURE:
<221> NAME/KEY: misc_feature
<222> LOCATION: (117)..(117)
<223> OTHER INFORMATION: Xaa is any amino acid
<220> FEATURE:
<221> NAME/KEY: misc_feature
<222> LOCATION: (120)..(120)
<223> OTHER INFORMATION: Xaa is any amino acid

<400> SEQUENCE: 72

Met Pro Xaa Leu Ser Ser Phe Ile Thr Ile Xaa Xaa Xaa Xaa Xaa Xaa
1               5                   10                  15

Val Phe Thr Arg Thr Ala Ile Tyr Ser Xaa Tyr Ala Ala Val Gln Trp
            20                  25                  30

Xaa Pro Glu Pro Xaa Xaa Ser Ile Xaa Pro Xaa Lys Trp Asp Leu Phe
        35                  40                  45

Ile Leu Xaa Asp Ile Leu Ser Ile Xaa Gly Thr Ser Gly Tyr Val Gln
    50                  55                  60

Tyr Xaa Val Xaa Xaa Xaa Pro Xaa Trp Val Arg Val Thr Phe Ser Ser
65              70                  75                  80

Leu Val Gly Ala Xaa Xaa Val Ala Xaa Trp Ser Ser Gly Asp Leu Pro
                85                  90                  95

Xaa Gly Phe Val Xaa Xaa Xaa Pro Xaa Xaa Xaa Xaa Xaa Xaa Pro Leu
            100                 105                 110

Gln Ala Thr Phe Xaa Ala Thr Xaa Gln
            115                 120

<210> SEQ ID NO 73
<211> LENGTH: 121
<212> TYPE: PRT
<213> ORGANISM: Artificial Sequence
<220> FEATURE:
<223> OTHER INFORMATION: Consensus Sequence 3
<220> FEATURE:
<221> NAME/KEY: misc_feature
<222> LOCATION: (3)..(3)
<223> OTHER INFORMATION: Xaa is Asp, Glu, Asn or Gln
<220> FEATURE:
<221> NAME/KEY: misc_feature
<222> LOCATION: (11)..(11)
<223> OTHER INFORMATION: Xaa is Lys, Arg, or His
<220> FEATURE:
<221> NAME/KEY: misc_feature
<222> LOCATION: (12)..(13)
<223> OTHER INFORMATION: Xaa is Asp, Glu, Asn or Gln
<220> FEATURE:
<221> NAME/KEY: misc_feature
<222> LOCATION: (14)..(14)
<223> OTHER INFORMATION: Xaa is Ser, Cys, Thr. or Met
<220> FEATURE:
<221> NAME/KEY: misc_feature
<222> LOCATION: (15)..(15)
<223> OTHER INFORMATION: Xaa is Asp, Glu, Asn or Gln
<220> FEATURE:
<221> NAME/KEY: misc_feature
<222> LOCATION: (16)..(16)
<223> OTHER INFORMATION: Xaa is Val, Gly, Ala, Leu.or Ile
<220> FEATURE:
<221> NAME/KEY: misc_feature
<222> LOCATION: (26)..(26)
<223> OTHER INFORMATION: Xaa is Lys, Arg, or His
<220> FEATURE:
<221> NAME/KEY: misc_feature
<222> LOCATION: (33)..(33)
```

```
<223> OTHER INFORMATION: Xaa is Ser, Cys, Thr. or Met
<220> FEATURE:
<221> NAME/KEY: misc_feature
<222> LOCATION: (37)..(37)
<223> OTHER INFORMATION: Xaa is Asp, Glu, Asn or Gln
<220> FEATURE:
<221> NAME/KEY: misc_feature
<222> LOCATION: (38)..(38)
<223> OTHER INFORMATION: Xaa is Val, Gly, Ala, Leu.or Ile
<220> FEATURE:
<221> NAME/KEY: misc_feature
<222> LOCATION: (41)..(41)
<223> OTHER INFORMATION: Xaa is Ser, Cys, Thr. or Met
<220> FEATURE:
<221> NAME/KEY: misc_feature
<222> LOCATION: (43)..(43)
<223> OTHER INFORMATION: Xaa is Val, Gly, Ala, Leu.or Ile
<220> FEATURE:
<221> NAME/KEY: misc_feature
<222> LOCATION: (51)..(51)
<223> OTHER INFORMATION: Xaa is Lys, Arg, or His
<220> FEATURE:
<221> NAME/KEY: misc_feature
<222> LOCATION: (57)..(57)
<223> OTHER INFORMATION: Xaa is Lys, Arg, or His
<220> FEATURE:
<221> NAME/KEY: misc_feature
<222> LOCATION: (66)..(66)
<223> OTHER INFORMATION: Xaa is Lys, Arg, or His
<220> FEATURE:
<221> NAME/KEY: misc_feature
<222> LOCATION: (68)..(68)
<223> OTHER INFORMATION: Xaa is Val, Gly, Ala, Leu.or Ile
<220> FEATURE:
<221> NAME/KEY: misc_feature
<222> LOCATION: (69)..(69)
<223> OTHER INFORMATION: Xaa is Asp, Glu, Asn or Gln
<220> FEATURE:
<221> NAME/KEY: misc_feature
<222> LOCATION: (70)..(70)
<223> OTHER INFORMATION: Xaa is Val, Gly, Ala, Leu.or Ile
<220> FEATURE:
<221> NAME/KEY: misc_feature
<222> LOCATION: (72)..(72)
<223> OTHER INFORMATION: Xaa is Val, Gly, Ala, Leu.or Ile
<220> FEATURE:
<221> NAME/KEY: misc_feature
<222> LOCATION: (85)..(86)
<223> OTHER INFORMATION: Xaa is Asp, Glu, Asn or Gln
<220> FEATURE:
<221> NAME/KEY: misc_feature
<222> LOCATION: (89)..(89)
<223> OTHER INFORMATION: Xaa is Asp, Glu, Asn or Gln
<220> FEATURE:
<221> NAME/KEY: misc_feature
<222> LOCATION: (97)..(97)
<223> OTHER INFORMATION: Xaa is Asp, Glu, Asn or Gln
<220> FEATURE:
<221> NAME/KEY: misc_feature
<222> LOCATION: (101)..(101)
<223> OTHER INFORMATION: Xaa is Val, Gly, Ala, Leu.or Ile
<220> FEATURE:
<221> NAME/KEY: misc_feature
<222> LOCATION: (102)..(102)
<223> OTHER INFORMATION: Xaa is Asp, Glu, Asn or Gln
<220> FEATURE:
<221> NAME/KEY: misc_feature
<222> LOCATION: (103)..(103)
<223> OTHER INFORMATION: Xaa is Lys, Arg, or His
<220> FEATURE:
<221> NAME/KEY: misc_feature
<222> LOCATION: (105)..(105)
<223> OTHER INFORMATION: Xaa is Val, Gly, Ala, Leu.or Ile
<220> FEATURE:
<221> NAME/KEY: misc_feature
<222> LOCATION: (106)..(106)
<223> OTHER INFORMATION: Xaa is Lys, Arg, or His
<220> FEATURE:
<221> NAME/KEY: misc_feature
```

```
<222> LOCATION: (107)..(107)
<223> OTHER INFORMATION: Xaa is Ser, Cys, Thr. or Met
<220> FEATURE:
<221> NAME/KEY: misc_feature
<222> LOCATION: (108)..(108)
<223> OTHER INFORMATION: Xaa is Val, Gly, Ala, Leu.or Ile
<220> FEATURE:
<221> NAME/KEY: misc_feature
<222> LOCATION: (108)..(108)
<223> OTHER INFORMATION: Xaa is Val, Gly, Ala, Leu, or Ile
<220> FEATURE:
<221> NAME/KEY: misc_feature
<222> LOCATION: (109)..(109)
<223> OTHER INFORMATION: Xaa is Ser, Cys, Thr. or Met
<220> FEATURE:
<221> NAME/KEY: misc_feature
<222> LOCATION: (110)..(110)
<223> OTHER INFORMATION: Xaa is Lys, Arg, or His
<220> FEATURE:
<221> NAME/KEY: misc_feature
<222> LOCATION: (117)..(117)
<223> OTHER INFORMATION: Xaa is Asp, Glu, Asn or Gln
<220> FEATURE:
<221> NAME/KEY: misc_feature
<222> LOCATION: (120)..(120)
<223> OTHER INFORMATION: Xaa is Lys, Arg, or His

<400> SEQUENCE: 73

Met Pro Xaa Leu Ser Ser Phe Ile Thr Ile Xaa Xaa Xaa Xaa Xaa Xaa
1               5                   10                  15

Val Phe Thr Arg Thr Ala Ile Tyr Ser Xaa Tyr Ala Ala Val Gln Trp
            20                  25                  30

Xaa Pro Glu Pro Xaa Xaa Ser Ile Xaa Pro Xaa Lys Trp Asp Leu Phe
        35                  40                  45

Ile Leu Xaa Asp Ile Leu Ser Ile Xaa Gly Thr Ser Gly Tyr Val Gln
    50                  55                  60

Tyr Xaa Val Xaa Xaa Xaa Pro Xaa Trp Val Arg Val Thr Phe Ser Ser
65                  70                  75                  80

Leu Val Gly Ala Xaa Xaa Val Ala Xaa Trp Ser Ser Gly Asp Leu Pro
                85                  90                  95

Xaa Gly Phe Val Xaa Xaa Xaa Pro Xaa Xaa Xaa Xaa Xaa Xaa Pro Leu
            100                 105                 110

Gln Ala Thr Phe Xaa Ala Thr Xaa Gln
            115                 120

<210> SEQ ID NO 74
<211> LENGTH: 121
<212> TYPE: PRT
<213> ORGANISM: Artificial Sequence
<220> FEATURE:
<223> OTHER INFORMATION: Consensus Sequence 4
<220> FEATURE:
<221> NAME/KEY: misc_feature
<222> LOCATION: (3)..(3)
<223> OTHER INFORMATION: Xaa is Asp or Glu
<220> FEATURE:
<221> NAME/KEY: misc_feature
<222> LOCATION: (11)..(11)
<223> OTHER INFORMATION: Xaa is Lys or Arg
<220> FEATURE:
<221> NAME/KEY: misc_feature
<222> LOCATION: (12)..(13)
<223> OTHER INFORMATION: Xaa is Asn or Gln
<220> FEATURE:
<221> NAME/KEY: misc_feature
<222> LOCATION: (14)..(14)
<223> OTHER INFORMATION: Xaa is Ser or Thr
<220> FEATURE:
<221> NAME/KEY: misc_feature
<222> LOCATION: (15)..(15)
```

```
<223> OTHER INFORMATION: Xaa is Asn or Gln
<220> FEATURE:
<221> NAME/KEY: misc_feature
<222> LOCATION: (16)..(16)
<223> OTHER INFORMATION: Xaa is Leu, Val, or Ile
<220> FEATURE:
<221> NAME/KEY: misc_feature
<222> LOCATION: (26)..(26)
<223> OTHER INFORMATION: Xaa is Lys or Arg
<220> FEATURE:
<221> NAME/KEY: misc_feature
<222> LOCATION: (33)..(33)
<223> OTHER INFORMATION: Xaa is Ser or Thr
<220> FEATURE:
<221> NAME/KEY: misc_feature
<222> LOCATION: (37)..(37)
<223> OTHER INFORMATION: Xaa is Asn or Gln
<220> FEATURE:
<221> NAME/KEY: misc_feature
<222> LOCATION: (38)..(38)
<223> OTHER INFORMATION: Xaa is Leu, Val, or Ile
<220> FEATURE:
<221> NAME/KEY: misc_feature
<222> LOCATION: (41)..(41)
<223> OTHER INFORMATION: Xaa is Ser or Thr
<220> FEATURE:
<221> NAME/KEY: misc_feature
<222> LOCATION: (43)..(43)
<223> OTHER INFORMATION: Xaa is Gly or Ala
<220> FEATURE:
<221> NAME/KEY: misc_feature
<222> LOCATION: (51)..(51)
<223> OTHER INFORMATION: Xaa is Lys or Arg
<220> FEATURE:
<221> NAME/KEY: misc_feature
<222> LOCATION: (57)..(57)
<223> OTHER INFORMATION: Xaa is Lys or Arg
<220> FEATURE:
<221> NAME/KEY: misc_feature
<222> LOCATION: (66)..(66)
<223> OTHER INFORMATION: Xaa is Lys or Arg
<220> FEATURE:
<221> NAME/KEY: misc_feature
<222> LOCATION: (68)..(68)
<223> OTHER INFORMATION: Xaa is Gly or Ala
<220> FEATURE:
<221> NAME/KEY: misc_feature
<222> LOCATION: (69)..(69)
<223> OTHER INFORMATION: Xaa is Asp or Glu
<220> FEATURE:
<221> NAME/KEY: misc_feature
<222> LOCATION: (70)..(70)
<223> OTHER INFORMATION: Xaa is Gly or Ala
<220> FEATURE:
<221> NAME/KEY: misc_feature
<222> LOCATION: (72)..(72)
<223> OTHER INFORMATION: Xaa is Gly or Ala
<220> FEATURE:
<221> NAME/KEY: misc_feature
<222> LOCATION: (85)..(86)
<223> OTHER INFORMATION: Xaa is Asp or Glu
<220> FEATURE:
<221> NAME/KEY: misc_feature
<222> LOCATION: (89)..(89)
<223> OTHER INFORMATION: Xaa is Asp or Glu
<220> FEATURE:
<221> NAME/KEY: misc_feature
<222> LOCATION: (97)..(97)
<223> OTHER INFORMATION: Xaa is Asp or Glu
<220> FEATURE:
<221> NAME/KEY: misc_feature
<222> LOCATION: (101)..(101)
<223> OTHER INFORMATION: Xaa is Leu, Val, or Ile
<220> FEATURE:
<221> NAME/KEY: misc_feature
<222> LOCATION: (102)..(102)
<223> OTHER INFORMATION: Xaa is Asn or Gln
<220> FEATURE:
<221> NAME/KEY: misc_feature
```

```
<222> LOCATION: (103)..(103)
<223> OTHER INFORMATION: Xaa is Lys or Arg
<220> FEATURE:
<221> NAME/KEY: misc_feature
<222> LOCATION: (105)..(105)
<223> OTHER INFORMATION: Xaa is Leu, Val, or Ile
<220> FEATURE:
<221> NAME/KEY: misc_feature
<222> LOCATION: (106)..(106)
<223> OTHER INFORMATION: Xaa is Lys or Arg
<220> FEATURE:
<221> NAME/KEY: misc_feature
<222> LOCATION: (107)..(107)
<223> OTHER INFORMATION: Xaa is Ser or Thr
<220> FEATURE:
<221> NAME/KEY: misc_feature
<222> LOCATION: (108)..(108)
<223> OTHER INFORMATION: Xaa is Gly or Ala
<220> FEATURE:
<221> NAME/KEY: misc_feature
<222> LOCATION: (109)..(109)
<223> OTHER INFORMATION: Xaa is Ser or Thr
<220> FEATURE:
<221> NAME/KEY: misc_feature
<222> LOCATION: (110)..(110)
<223> OTHER INFORMATION: Xaa is Lys or Arg
<220> FEATURE:
<221> NAME/KEY: misc_feature
<222> LOCATION: (117)..(117)
<223> OTHER INFORMATION: Xaa is Asp or Glu
<220> FEATURE:
<221> NAME/KEY: misc_feature
<222> LOCATION: (120)..(120)
<223> OTHER INFORMATION: Xaa is Lys or Arg

<400> SEQUENCE: 74

Met Pro Xaa Leu Ser Ser Phe Ile Thr Ile Xaa Xaa Xaa Xaa Xaa Xaa
 1               5                  10                  15

Val Phe Thr Arg Thr Ala Ile Tyr Ser Xaa Tyr Ala Ala Val Gln Trp
             20                  25                  30

Xaa Pro Glu Pro Xaa Xaa Ser Ile Xaa Pro Xaa Lys Trp Asp Leu Phe
         35                  40                  45

Ile Leu Xaa Asp Ile Leu Ser Ile Xaa Gly Thr Ser Gly Tyr Val Gln
     50                  55                  60

Tyr Xaa Val Xaa Xaa Xaa Pro Xaa Trp Val Arg Val Thr Phe Ser Ser
 65                  70                  75                  80

Leu Val Gly Ala Xaa Xaa Val Ala Xaa Trp Ser Ser Gly Asp Leu Pro
                 85                  90                  95

Xaa Gly Phe Val Xaa Xaa Xaa Pro Xaa Xaa Xaa Xaa Xaa Xaa Pro Leu
            100                 105                 110

Gln Ala Thr Phe Xaa Ala Thr Xaa Gln
            115                 120

<210> SEQ ID NO 75
<211> LENGTH: 121
<212> TYPE: PRT
<213> ORGANISM: Artificial Sequence
<220> FEATURE:
<223> OTHER INFORMATION: Consensus Sequence 5
<220> FEATURE:
<221> NAME/KEY: misc_feature
<222> LOCATION: (3)..(3)
<223> OTHER INFORMATION: Xaa is Asp or Glu
<220> FEATURE:
<221> NAME/KEY: misc_feature
<222> LOCATION: (11)..(11)
<223> OTHER INFORMATION: Xaa is Lys or Arg
<220> FEATURE:
<221> NAME/KEY: misc_feature
<222> LOCATION: (26)..(26)
```

```
<223> OTHER INFORMATION: Xaa is Lys or Arg
<220> FEATURE:
<221> NAME/KEY: misc_feature
<222> LOCATION: (51)..(51)
<223> OTHER INFORMATION: Xaa is Lys or Arg
<220> FEATURE:
<221> NAME/KEY: misc_feature
<222> LOCATION: (57)..(57)
<223> OTHER INFORMATION: Xaa is Lys or Arg
<220> FEATURE:
<221> NAME/KEY: misc_feature
<222> LOCATION: (66)..(66)
<223> OTHER INFORMATION: Xaa is Lys or Arg
<220> FEATURE:
<221> NAME/KEY: misc_feature
<222> LOCATION: (69)..(69)
<223> OTHER INFORMATION: Xaa is Asp or Glu
<220> FEATURE:
<221> NAME/KEY: misc_feature
<222> LOCATION: (85)..(85)
<223> OTHER INFORMATION: Xaa is Asp or Glu
<220> FEATURE:
<221> NAME/KEY: misc_feature
<222> LOCATION: (86)..(86)
<223> OTHER INFORMATION: Xaa is Asp or Glu
<220> FEATURE:
<221> NAME/KEY: misc_feature
<222> LOCATION: (89)..(89)
<223> OTHER INFORMATION: Xaa is Asp or Glu
<220> FEATURE:
<221> NAME/KEY: misc_feature
<222> LOCATION: (97)..(97)
<223> OTHER INFORMATION: Xaa is Asp or Glu
<220> FEATURE:
<221> NAME/KEY: misc_feature
<222> LOCATION: (103)..(103)
<223> OTHER INFORMATION: Xaa is Lys or Arg
<220> FEATURE:
<221> NAME/KEY: misc_feature
<222> LOCATION: (106)..(106)
<223> OTHER INFORMATION: Xaa is Lys or Arg
<220> FEATURE:
<221> NAME/KEY: misc_feature
<222> LOCATION: (110)..(110)
<223> OTHER INFORMATION: Xaa is Lys or Arg
<220> FEATURE:
<221> NAME/KEY: misc_feature
<222> LOCATION: (117)..(117)
<223> OTHER INFORMATION: Xaa is Asp or Glu
<220> FEATURE:
<221> NAME/KEY: misc_feature
<222> LOCATION: (120)..(120)
<223> OTHER INFORMATION: Xaa is Lys or Arg

<400> SEQUENCE: 75

Met Pro Xaa Leu Ser Ser Phe Ile Thr Ile Xaa Asn Asn Ser Asn His
1               5                   10                  15

Val Phe Thr Arg Thr Ala Ile Tyr Ser Xaa Tyr Ala Ala Val Gln Trp
            20                  25                  30

Ser Pro Glu Pro Gln Leu Ser Ile Ser Pro Gly Lys Trp Asp Leu Phe
        35                  40                  45

Ile Leu Xaa Asp Ile Leu Ser Ile Xaa Gly Thr Ser Gly Tyr Val Gln
    50                  55                  60

Tyr Xaa Val Gly Xaa Gly Pro Gly Trp Val Arg Val Thr Phe Ser Ser
65                  70                  75                  80

Leu Val Gly Ala Xaa Xaa Val Ala Xaa Trp Ser Ser Gly Asp Leu Pro
                85                  90                  95
```

```
Xaa Gly Phe Val Leu Gln Xaa Pro Val Xaa Thr Gly Ser Xaa Pro Leu
            100                 105                 110

Gln Ala Thr Phe Xaa Ala Thr Xaa Gln
        115             120
```